US008288120B2

(12) United States Patent
Deutsch

(10) Patent No.: US 8,288,120 B2
(45) Date of Patent: Oct. 16, 2012

(54) METHOD FOR STUDYING FLOATING, LIVING CELLS

(75) Inventor: Mordechai Deutsch, Moshav Olesh Doar-Na Lev HaSharon (IL)

(73) Assignee: Seng Enterprises Ltd., Larnaca (CY)

( * ) Notice: Subject to any disclaimer, the term of this patent is extended or adjusted under 35 U.S.C. 154(b) by 323 days.

(21) Appl. No.: 12/084,462

(22) PCT Filed: Apr. 20, 2006

(86) PCT No.: PCT/IL2006/000483
§ 371 (c)(1),
(2), (4) Date: May 1, 2008

(87) PCT Pub. No.: WO2007/052245
PCT Pub. Date: May 10, 2007

(65) Prior Publication Data
US 2009/0111141 A1    Apr. 30, 2009

Related U.S. Application Data

(60) Provisional application No. 60/734,287, filed on Nov. 8, 2005, provisional application No. 60/734,286, filed on Nov. 8, 2005, provisional application No. 60/732,827, filed on Nov. 3, 2005.

(51) Int. Cl.
*C12Q 1/24* (2006.01)
(52) U.S. Cl. .................. 435/30; 435/307.1; 382/133
(58) Field of Classification Search ............ 435/30, 435/307.1; 382/133
See application file for complete search history.

(56) References Cited

U.S. PATENT DOCUMENTS

| | | | |
|---|---|---|---|
| 3,558,387 A | 1/1971 | Bassemir et al. |
| 4,072,578 A | 2/1978 | Cady et al. |
| 4,207,554 A | 6/1980 | Resnick et al. |
| 4,308,351 A | 12/1981 | Leighton et al. |
| 4,684,538 A | 8/1987 | Klemarczyk |
| 4,716,101 A | 12/1987 | Thompson et al. |
| 4,729,949 A | 3/1988 | Weinreb et al. |
| 4,894,343 A | 1/1990 | Tanaka et al. |
| 4,895,805 A | 1/1990 | Sato et al. |
| 5,043,082 A | 8/1991 | Hermann, Jr. et al. |
| 5,059,266 A | 10/1991 | Yamane et al. |
| 5,204,055 A | 4/1993 | Sachs et al. |
| 5,272,081 A | 12/1993 | Weinreb |
| 5,324,591 A | 6/1994 | Georger et al. |
| 5,395,588 A | 3/1995 | North, Jr. et al. |
| 5,428,451 A | 6/1995 | Lea et al. |
| 5,506,141 A | 4/1996 | Weinreb et al. |
| 5,525,800 A | 6/1996 | Sanghera et al. |
| 5,612,184 A | 3/1997 | Rosson |
| 5,627,045 A | 5/1997 | Bochner et al. |
| 5,650,323 A | 7/1997 | Root et al. |
| 5,707,869 A | 1/1998 | Wolf et al. |
| 5,854,684 A | 12/1998 | Stabile et al. |
| 5,905,031 A | 5/1999 | Kuylen et al. |
| 5,910,287 A | 6/1999 | Cassin et al. |
| 6,025,129 A | 2/2000 | Nova et al. |
| 6,027,695 A | 2/2000 | Oldenburg et al. |
| 6,046,426 A | 4/2000 | Jeantette et al. |
| 6,066,285 A | 5/2000 | Kumar |
| 6,103,479 A | 8/2000 | Taylor |
| 6,117,612 A | 9/2000 | Halloran et al. |
| 6,206,672 B1 | 3/2001 | Grenda |
| 6,228,437 B1 | 5/2001 | Schmidt |
| 6,238,614 B1 | 5/2001 | Yang et al. |
| 6,315,940 B1 | 11/2001 | Nisch et al. |
| 6,329,195 B1 | 12/2001 | Pfaller |
| 6,333,192 B1 | 12/2001 | Petitte et al. |
| 6,338,964 B1 | 1/2002 | Matanguihan et al. |
| 6,342,384 B1 | 1/2002 | Chung et al. |
| 6,344,354 B1 | 2/2002 | Webster et al. |
| 6,345,115 B1 | 2/2002 | Ramm et al. |
| 6,372,494 B1 | 4/2002 | Naughton et al. |
| 6,376,148 B1 | 4/2002 | Liu et al. |
| 6,377,721 B1 | 4/2002 | Walt et al. |
| 6,378,527 B1 | 4/2002 | Hungerford et al. |
| 6,383,810 B2 | 5/2002 | Fike et al. |
| 6,403,369 B1 | 6/2002 | Wood |
| 6,410,309 B1 | 6/2002 | Barbera-Guillem et al. |
| 6,413,680 B1 | 7/2002 | Watanabe et al. |
| 6,413,744 B1 | 7/2002 | Morris et al. |

(Continued)

FOREIGN PATENT DOCUMENTS

DE    4132379    4/1993

(Continued)

OTHER PUBLICATIONS

Communication Pursuant to Article 94(3) EPC Dated Nov. 16, 2011 From the European Patent Office Re. Application No. 04744911.1.
Communication Pursuant to Rules 70(2) and 70a(2) EPC and Reference to Rule 39(1) EPC Dated Sep. 5, 2011 From the European Patent Office Re. Application No. 10183774.8.
Official Action Dated Oct. 18, 2011 From the US Patent and Trademark Office Re.: U.S. Appl. No. 11/631,737.
Official Action Dated Oct. 19, 2011 From the US Patent and Trademark Office Re. U.S. Appl. No. 12/155,643.
Partial European Search Report Dated Oct. 27, 2011 From the European Patent Office Re. Application No. 11170000.1.
Response Dated Nov. 1, 2011 to Official Action of Oct. 19, 2011 From the US Patent and Trademark Office Re. U.S. Appl. No. 12/155,643.
Response Dated Nov. 21, 2011 to Communication Pursuant to Article 94(3) EPC of Aug. 4, 2011 From the European Patent Office Re. Application No. 08865081.7.
Communication Pursuant to Article 94(3) EPC Dated Dec. 2, 2011 From the European Patent Office Re.: Application No. 04714873.9.
Office Action Dated Apr. 12, 2011 From the Israel Patent Office Re.: Application No. 173170 and Its Translation Into English.

(Continued)

*Primary Examiner* — Ralph Gitomer

(57) ABSTRACT

Disclosed is a method of studying floating living cell by confining the cells floating in an aqueous medium in picowells located on a bottom surface of a top wall of a chamber. Disclosed is also a picowell-bearing device for the study of cells comprising a chamber having at least one picowell on a bottom surface of the chamber. Also disclosed is a picowell-bearing device for the study of cells comprising a chamber having at least one picowell on an internal surface and at least one moveable wall, a force applicator configured to removeably apply a substantially uniformly distributed force around the periphery of the moveable wall in a direction to retain the moveable wall secured to the chamber.

24 Claims, 27 Drawing Sheets

U.S. PATENT DOCUMENTS

| | | |
|---|---|---|
| 6,413,746 B1 | 7/2002 | Field |
| 6,455,310 B1 | 9/2002 | Barbera-Guillem et al. |
| 6,465,000 B1 | 10/2002 | Kim |
| 6,465,205 B2 | 10/2002 | Hicks, Jr. |
| 6,468,788 B1 | 10/2002 | Marotzki |
| 6,479,252 B1 | 11/2002 | Barbera-Guillem et al. |
| 6,485,690 B1 | 11/2002 | Pfost et al. |
| 6,489,144 B1 | 12/2002 | Lau |
| 6,492,148 B1 | 12/2002 | van Loon et al. |
| 6,492,163 B1 | 12/2002 | Yoo et al. |
| 6,495,340 B2 | 12/2002 | Huberman et al. |
| 6,506,598 B1 | 1/2003 | Andersen et al. |
| 6,511,430 B1 | 1/2003 | Sherar et al. |
| 6,528,286 B1 | 3/2003 | Ryll |
| 6,544,788 B2 | 4/2003 | Singh |
| 6,555,365 B2 | 4/2003 | Barbera-Guillem et al. |
| 6,569,422 B1 | 5/2003 | van Loon et al. |
| 6,588,586 B2 | 7/2003 | Abasolo et al. |
| 6,589,765 B1 | 7/2003 | Choi et al. |
| 6,593,101 B2 | 7/2003 | Richards-Kortum et al. |
| 6,593,140 B1 | 7/2003 | Field |
| 6,610,516 B1 | 8/2003 | Andersen et al. |
| 6,627,426 B2 | 9/2003 | Biddle et al. |
| 6,632,619 B1 | 10/2003 | Harrison et al. |
| 6,635,448 B2 | 10/2003 | Bucciarelli et al. |
| 6,642,050 B1 | 11/2003 | Goto et al. |
| 6,645,757 B1 | 11/2003 | Okandan et al. |
| 6,649,408 B2 | 11/2003 | Bailey et al. |
| 6,653,124 B1 | 11/2003 | Freeman |
| 6,660,501 B2 | 12/2003 | Field |
| 6,667,034 B2 | 12/2003 | Palsson et al. |
| 6,670,180 B2 | 12/2003 | Block |
| 6,670,184 B2 | 12/2003 | Chiarello et al. |
| 6,673,591 B2 | 1/2004 | Lau |
| 6,686,190 B2 | 2/2004 | Lau |
| 6,689,594 B1 | 2/2004 | Hänni et al. |
| 6,692,961 B1 | 2/2004 | Battista et al. |
| 6,699,665 B1 | 3/2004 | Kim et al. |
| 6,706,519 B1 | 3/2004 | Kellogg et al. |
| 7,118,910 B2 | 10/2006 | Unger et al. |
| 7,139,415 B2 | 11/2006 | Finkbeiner |
| 7,169,578 B2 | 1/2007 | Wang et al. |
| 7,285,412 B2 | 10/2007 | Casagrande et al. |
| 7,323,305 B2 | 1/2008 | Leamon et al. |
| 7,354,733 B2 | 4/2008 | Bukshpan et al. |
| 7,403,647 B2 | 7/2008 | Deutsch et al. |
| 7,405,071 B2 | 7/2008 | Deutsch |
| 7,888,110 B2 * | 2/2011 | Deutsch et al. ............ 435/288.5 |
| 2002/0001856 A1 | 1/2002 | Chow et al. |
| 2002/0052003 A1 | 5/2002 | Alberte et al. |
| 2002/0064885 A1 | 5/2002 | Bedingham et al. |
| 2002/0106715 A1 | 8/2002 | Huberman et al. |
| 2002/0127604 A1 | 9/2002 | Allbritton et al. |
| 2002/0150909 A1 | 10/2002 | Stuelpnagel et al. |
| 2002/0173033 A1 | 11/2002 | Hammerick et al. |
| 2002/0182627 A1 | 12/2002 | Wang et al. |
| 2002/0187074 A1 | 12/2002 | O'Connor et al. |
| 2002/0189374 A1 | 12/2002 | DeSilets et al. |
| 2003/0017079 A1 | 1/2003 | Hahn et al. |
| 2003/0030184 A1 | 2/2003 | Kim et al. |
| 2003/0032204 A1 | 2/2003 | Walt et al. |
| 2003/0036188 A1 | 2/2003 | Kim et al. |
| 2003/0059764 A1 | 3/2003 | Ravkin et al. |
| 2003/0082632 A1 | 5/2003 | Shumate |
| 2003/0082818 A1 | 5/2003 | Bahnson et al. |
| 2003/0104494 A1 | 6/2003 | Ravkin et al. |
| 2003/0113833 A1 | 6/2003 | Oka et al. |
| 2003/0124716 A1 | 7/2003 | Hess et al. |
| 2003/0189850 A1 | 10/2003 | Sasaki et al. |
| 2003/0211458 A1 | 11/2003 | Sunray et al. |
| 2004/0053354 A1 | 3/2004 | Ikawa et al. |
| 2004/0091397 A1 | 5/2004 | Picard |
| 2004/0118757 A1 | 6/2004 | Terstappen et al. |
| 2004/0216835 A1 | 11/2004 | Tanner et al. |
| 2004/0235143 A1 | 11/2004 | Sasaki et al. |
| 2004/0241783 A1 | 12/2004 | Papkovsky et al. |
| 2004/0262210 A1 | 12/2004 | Westervelt et al. |
| 2005/0014201 A1 | 1/2005 | Deuthsch |
| 2005/0026299 A1 | 2/2005 | Bhattacharjee et al. |
| 2005/0064524 A1 | 3/2005 | Deutsch et al. |
| 2005/0170498 A1 | 8/2005 | Dolley et al. |
| 2005/0277125 A1 | 12/2005 | Benn et al. |
| 2006/0041384 A1 | 2/2006 | Kermani et al. |
| 2006/0057557 A1 | 3/2006 | Deutsch et al. |
| 2006/0154233 A1 | 7/2006 | Deutsch |
| 2006/0240548 A1 | 10/2006 | Deutsch et al. |
| 2007/0105089 A1 | 5/2007 | Deutsch |
| 2007/0141555 A1 | 6/2007 | Deutsch |
| 2007/0154357 A1 | 7/2007 | Szlosek |
| 2007/0178607 A1 | 8/2007 | Prober et al. |
| 2007/0292837 A1 | 12/2007 | Deutsch et al. |
| 2008/0003142 A1 | 1/2008 | Link et al. |
| 2008/0009051 A1 | 1/2008 | Deutsch et al. |
| 2008/0063251 A1 | 3/2008 | Deutsch |
| 2008/0063572 A1 | 3/2008 | Deutsch et al. |
| 2008/0241874 A1 | 10/2008 | Deutsch |
| 2009/0105095 A1 | 4/2009 | Deutsch |
| 2009/0111141 A1 | 4/2009 | Deutsch |
| 2011/0014688 A1 | 1/2011 | Deutsch et al. |

FOREIGN PATENT DOCUMENTS

| | | |
|---|---|---|
| EP | 0059297 | 9/1982 |
| EP | 0094193 | 11/1983 |
| EP | 0602416 | 6/1994 |
| EP | 1262764 | 12/2002 |
| EP | 1566635 | 8/2005 |
| EP | 1691196 | 8/2006 |
| JP | 62-171687 | 7/1987 |
| JP | 06-221988 | 8/1994 |
| JP | 06-237753 | 8/1994 |
| JP | 10-276763 | 10/1998 |
| JP | 11-507724 | 7/1999 |
| JP | 2005-102628 | 4/2005 |
| WO | WO 96/31548 | 10/1996 |
| WO | WO 96/41153 | 12/1996 |
| WO | WO 98/15356 | 4/1998 |
| WO | WO 98/35223 | 8/1998 |
| WO | WO 99/45357 | 9/1999 |
| WO | WO 99/47922 | 9/1999 |
| WO | WO 99/66329 | 12/1999 |
| WO | WO 00/20554 | 4/2000 |
| WO | WO 01/02539 | 1/2001 |
| WO | WO 01/35071 | 5/2001 |
| WO | WO 01/49824 | 7/2001 |
| WO | WO 01/88176 | 11/2001 |
| WO | WO 01/88185 | 11/2001 |
| WO | WO 02/08748 | 1/2002 |
| WO | WO 02/26114 | 4/2002 |
| WO | WO 02/48676 | 6/2002 |
| WO | WO 02/055653 | 7/2002 |
| WO | WO 02/058847 | 8/2002 |
| WO | WO 02/063034 | 8/2002 |
| WO | WO 02/064728 | 8/2002 |
| WO | WO 02/081662 | 10/2002 |
| WO | WO 02/097398 | 12/2002 |
| WO | WO 03/011451 | 2/2003 |
| WO | WO 03/035824 | 5/2003 |
| WO | WO 03/046508 | 6/2003 |
| WO | WO 03/052375 | 6/2003 |
| WO | WO 03/056330 | 7/2003 |
| WO | WO 03/056345 | 7/2003 |
| WO | WO 2004/077009 | 9/2004 |
| WO | WO 2004/113492 * | 12/2004 |
| WO | WO 2004/113492 A1 * | 12/2004 |
| WO | WO 2005/007796 | 1/2005 |
| WO | WO 2005/007796 A2 * | 1/2005 |
| WO | WO 2005/069001 | 7/2005 |
| WO | WO 2005/103691 | 11/2005 |
| WO | WO 2006/003664 | 1/2006 |
| WO | WO 2006/021959 | 3/2006 |
| WO | WO 2006/043267 | 4/2006 |
| WO | WO 2006/080000 | 8/2006 |
| WO | WO 2007/052245 | 5/2007 |
| WO | WO 2007/074449 | 7/2007 |
| WO | WO 2009/063462 | 5/2009 |
| WO | WO 2009/081409 | 7/2009 |

OTHER PUBLICATIONS

Official Action Dated Dec. 19, 2011 From the US Patent and Trademark Office Re.: U.S. Appl. No. 10/492,531.
Official Action Dated Nov. 22, 2011 From the US Patent and Trademark Office Re.: U.S. Appl. No. 11/646,317.
Official Action Dated Dec. 23, 2011 From the US Patent and Trademark Office Re. U.S. Appl. No. 10/565,240.
Official Action Dated Nov. 23, 2011 From the US Patent and Trademark Office Re.: U.S. Appl. No. 10/561,839.
Response Dated May 19, 2011 to Invitation Pursuant to Article 94(3) and Rule 71(1) EPC of Apr. 8, 2011 From the European Patent Office Re. Application No. 01982673.4. Response Dated Jun. 29, 2011 to Official Action of Mar. 31, 2011 From the US Patent and Trademark Office Re.: U.S. Appl. No. 10/492,531.
Restriction Official Action Dated Dec. 9, 2011 From the US Patent and Trademark Office Re. U.S. Appl. No. 12/742,730.
Restriction Official Action Dated Dec. 12, 2011 From the US Patent and Trademark Office Re. U.S. Appl. No. 13/184,631.
Restriction Official Action Dated Jan. 19, 2012 From the US Patent and Trademark Office Re. U.S. Appl. No. 13/019,320.
Ducree "Polymer Prototyping von mikrofluidischen Strukturen. Projekt", Insitut f?r Mikrosystemtechnik, Albert-Ludwigs-Universit?t Freiburg i. Br., IMTEK, 4 P., 2004. Retrieved From the Internet: http://images.google.com/imgres?imgurl=http://www.imtek.de/anwendungen/content/upload/vorlesung/133/133-03-14_prototyping_hydrophobic. jpg&imgrefurl-http://www.imtek.de/content/projekte.php%3F1s%3D3%26nr%3D133&h-299&w-429&.
Suehiro et al. "The Dielectrophoretic Movement and Positioning of a Biological Cell Using a Three-Dimensional Grid Electrode System", Journal of Physics D: Applied Physics, 31: 3298-3305, 1998.
Communication Pursuant to Article 94(3) EPC Dated May 22, 2012 From the European Patent Office Re.: Application No. 04714873.9.
European Search Report and the European Search Opinion Dated Mar. 13, 2012 From the European Patent Office Re. Application No. 11170000.1.
Communication Pursuant to Article 94(3) EPC Dated Apr. 11, 2012 From the European Patent Office Re. Application No. 10183774.8.
Communication Pursuant to Rules 70(2) and 70a(2) EPC and Reference to Rule 39(1) EPC Dated Apr. 16, 2012 From the European Patent Office Re. Application No. 11170000.1.
Official Action Dated Mar. 6, 2012 From the US Patent and Trademark Office Re. U.S. Appl. No. 12/155,643.
Office Action Dated Feb. 2, 2012 From the Israel Patent Office Re.: Application No. 173170 and Its Translation Into English.
Aplin et al. "Protein-Derivatised Glass Coverslips for the Study of Cell-to-Substratum Adhesion", Analytical Biochemistry, 113: 144-148, 1981.
Arikawa et al. "Microbial Biosensors Based on Respiratory Inhibition", Methos in Biotechnology, 6(Chap.16): 225-235, 1998.
Baruch et al. "Enzyme Activity—It's All About Image", Trends in Cell Biology, 14(1): 29-35, 2004.
Bedner et al. "Enzyme Kinetic Reactions and Fluorochrome Uptake Rates Measured in Individual Cells by Laser Scanning Cytometry", Cytometry, 33(1): 1-9, 1998. Abstract, p. 2, col. 1, §4-col. 2, §1, p. 8, col. 2, §2.
Burlage et al. "Living Biosensors for the Management and Manipulation of Microbial Consortia", Annual Reviews in Microbiology, 48: 291-309, 1994.
Darzynkiewicz et al. "Laser-Scanning Cytometry: A New Instrumentation With Many Applications", Experimental Cell Research, 249(1): 1-12, 1999. Abstract, p. 2, col. 2, §4-p. 4, col. 2, §2, p. 8, col. 1, §1-col. 2, §2.
Deutsch et al. "Apparatus for High-Precision Repetitive Sequential Optical Measurement of Living Cells", Cytometry, 16: 214-226, 1994.
Dive et al. "Improved Methodology for Intracellular Enzyme Reaction and Inhibition Kinetics by Flow Cytometry", Cytometry Journal of Society for Analytical Cytology, 8(6): 552-561, 1987.
Dolbeare "Fluorescent Staining of Enzymes for Flow Cytometry", Methods in Cell Biology, 33(Chap.8): 81-88, 1990.
Eisenthal et al. "Infection of K562 Cells With Influenza A Virus Increases Their Susceptibility to Natural Killer Lysis", Pathobiology, 65: 331-340, 1997.
Hestbjerg Hansen et al. "Quantification of Bioavailable Chlortetracycline in Pig Feces Using a Bacterial Whole-Cell Biosensor", Veterinary Microbiology, 87: 51-57, 2002.
Kiguchi et al. "Induction of Urokinase-Type Plasminogen Activator by the Anthracycline Antibiotic in Human RC-K8 Lymphoma and H69 Lung-Carcinoma Cells", International Journal of Cancer, 93: 792-797, 2001.
Klingel et al. "Flow Cytometric Determination of Serine Proteinase Activities in Living Cells With Rhodamine 110 Substrates", Methods in Cell Biology, 41(Chap.29): 449-460, 1994.
Koh et al. "Poly(Ethylene Glycol) Hydrogel Microstructures Encapsulating Living Cells", Langmuir, 18(7): 2459-2462, 2002. p. 2459-2462, Fig.3.
Kovacic et al. "Mechanisms of Carcinogenesis: Focus on Oxidative Stress and Electron Transfer", Current Medicinal Chemistry 8: 773-796, 2001.
Lansing Taylor et al. "Real-Time Molecular and Cellular Analysis: the New Frontier of Drug Discovery", Current Opinion in Biotechnology, 12: 75-81, 2001.
Malin-Berdel et al. "Flow Cytometric Determination of Esterase and Phosphatase Activities and Kinetics in Hematopoietic Cells With Fluorogenic Substrates", Cytometry, 1(3): 222-228, 1980.
Mrksich et al. "Using Self-Assembled Monolayers to Understand the Interactions of Man-Made Surfaces With Proteins and Cells", Annual Reviews in Biophysics and Biomolecular Structure, 25: 55-78, 1996.
Nooter et al. "On-Line Flow Cytometry. A Versatile Method for Kinetic Measurement", Methods in Cell Biology, 41(Chap.32): 509-526, 1994.
Riedel et al. "Arxula Adeninivorans Based Sensor for the Estimation of Bod", Analytical Letters, 31(1): 1-12, 1998.
Schroeder et al. "Coordination of Cell Growth in Cocultures by a Genetic Proliferation Control System", Biotechnology and Bioengineering, 78(3): 346-352, 2002.
Simonian et al. "Microbial Biosensors Based on Potentiometric Detection", Methods in Biotechnology, 6(Chap.17): 237-248, 1998.
Singhvi et al. "Engineering Cell Shape and Function", Science, 264: 696-698, 1994.
Suehiro et al. "The Dielectrophoretic Movement and Positioning of a Biological Cell Using a Three-Dimensional Grid Electrode System", J. Phys. D. Appl. Phys, vol. 31 p. 3298-3305, 1998.
Sunray et al. "Cell Activation Influences Cell Staining Kinetics", Spectrochimica Part A, 53: 1645-1653, 1997.
Sunray et al. "Determination of Individual Cell Michaelis-Menten Constants", Cytometry, 47(1): 8-16, 2002.
Sunray et al. "Determination of the Michaelis-Menten Constant (Km) of Intracellular Enzymatic Reaction for Individual Live Lymphocytes", Cytometry Supplement, 10: 68-69, & The XX Congress of the International Society for Analytical Cytology, Montpellier, F, 2000.
Sunray et al. "The Trace and Subgrouping of Lymphocyte Activation by Dynamic Fluorescence Intensity and Polarization Measurements", Biochemical and Biophysical Research Communications, 261(3): 712-719, 1999. Abstract, p. 713, col. 1, §5, col. 2, §7-p. 714, col. 2, §1.
Turek et al. "Leucine Aminopeptidase Activity by Flow Cytometry", Methods in Cell Biology, 41(Chap.30): 461-468 1994.
Watson et al. "Enzyme Kinetics", Methods in Cell Biology, 41: 469-508, 1994.
Yamamura et al. "Single-Cell Microarray for Analyzing Cellular Response", Analytical Chemistry, 77(24): 8050-8056, 2005.
Craighead et al. Textured Surfaces: Optical Storage and Other Applications,Journal of Vacuum Science and Technology 20 (3): 316, 1982. Abstract.
Official Action Dated Feb. 5, 2007 From the US Patent and Trademark Office Re.: U.S. Appl. No. 10/916,380.
Official Action Dated Feb. 19, 2008 From the US Patent and Trademark Office Re.: U.S. Appl. No. 10/492,531.
Official Action Dated Sep. 20, 2007 From the US Patent and Trademark Office Re.: U.S. Appl. No. 10/492,531.

Official Action Dated Jan. 25, 2007 From the US Patent and Trademark Office Re.: U.S. Appl. No. 10/492,531.
Communication Pursuant to Article 94(3) EPC Dated Feb. 13, 2009 From the European Patent Office Re.: Application No. 05763452.9.
Communication Pursuant to Article 94(3) EPC Dated Jun. 16, 2009 From the European Patent Office Re.: Application No. 04714873.9.
Communication Pursuant to Article 94(3) EPC Dated Feb. 29, 2008 From the European Patent Office Re.: 05763452.9.
Communication Relating to the Results of the Partial International Search Dated May 20, 2009 From the International Searching Authority Re.: Application No. PCT/IL2008/001678.
International Preliminary Report on Patentability Dated Feb. 2, 2006 From the International Bureau of WIPO Re.: Application No. PCT/IL2004/000661.
International Preliminary Report on Patentability Dated May 3, 2007From the International Bureau of WIPO Re.: Application No. PCT/IL2005/001078.
International Preliminary Report on Patentability Dated Mar. 8, 2007 From the International Bureau of WIPO Re.: Application No. PCT/IL2005/000914.
International Preliminary Report on Patentability Dated Jul. 10, 2008 From the International Bureau of WIPO Re.: Application No. PCT/IL2006/001487.
International Preliminary Report on Patentability Dated Jan. 18, 2007 From the International Bureau of WIPO Re.: Application No. PCT/IL2005/000719.
International Preliminary Report on Patentability Dated Nov. 28, 2007 From the International Bureau of WIPO Re.: Application No. PCT/IL2006/000483.
International Preliminary Report on Patentability Dated Aug. 9, 2007 From the International Bureau of WIPO Re.: Application No. PCT/IL2005/000801.
International Search Report Dated May 13, 2009 From the International Searching Authority Re.: Application No. PCT/IL08/01492.
Invitation to Pay Additional Fees Dated Mar. 3, 2009 From the International Searching Authority Re.: Application No. PCT/IL 08/01492.
Notice of Allowance Dated Mar. 4, 2008 From the US Patent and Trademark Office Re.: U.S. Appl. No. 10/546,784.
Notice of Allowance Dated Jan. 7, 2008 From the US.Patent and Trademark Office Re.: U.S. Appl. No. 10/938,951.
Office Action Dated Apr. 12, 2007 From the Israeli Patent Office Re.: Application No. 138314.
Office Action Dated Jul. 14, 2009 From the Israeli Patent Office Re.: Application No. 172724 and Its Translation Into English.
Office Action Dated Mar. 22, 2009 From the Israeli Patent Office Re.: Application No. 170492 and Its Translation Into English.
Official Action Dated Jul. 13, 2009 From the US Patent and Trademark Office Re.: U.S. Appl. No. 11/660,783.
Official Action Dated Dec. 14, 2007 From the US Patent and Trademark Office Re.: U.S. Appl. No. 10/916,380.
Official Action Dated Nov. 14, 2008 From the US Patent and Trademark Office Re.: U.S. Appl. No. 10/492,531.
Official Action Dated Oct. 16, 2006 From the US Patent and Trademark Office Re.: U.S. Appl. No. 10/492,531.
Official Action Dated Dec. 18, 2006 From the US Patent and Trademark Office Re.: U.S. Appl. No. 10/276,080.
Official Action Dated Mar. 23, 2005 From the US Patent and Trademark Office Re.: U.S. Appl. No. 10/276,080.
Official Action Dated Aug. 25, 2006 From the US Patent and Trademark Office Re.: U.S. Appl. No. 10/276,080.
Official Action Dated Aug. 28, 2007 From the US Patent and Trademark Office Re.: U.S. Appl. No. 10/916,380.
Official Action Dated Jun. 29, 2009 From the US Patent and Trademark Office Re.: U.S. Appl. No. 10/492,531.
Response Dated Apr. 29, 2005 to Communication Pursuant to Article 96(2) EPC of Dec. 23, 2004 From the European Patent Office Re.: Application No. 01934272.4.
Supplementary Partial European Search Report Dated Feb. 20, 2006 From the European Patent Office Re.: Application No. 04714873.9.
Translation of Notice of Reason for Rejection Dated Nov. 27, 2007 From Japanese Patent Office Re.: Application No. 2003-538325.
Written Opinion Dated May 13, 2009 From the International Searching Authority Re.: Application No. PCT/IL08/01492.
Ducrée "Polymer Prototyping von mikrofluidischen Strukturen. Projekt", Insitut fur Mikrosystemtechnik, Albert-Ludwigs-Universitat Freiburg i. Br., IMTEK, 4 P., 2004. Retrieved From the Internet.
Stevens et al. "Quorum Sensing in Vibrio Fischeri: Essential Elements for Activation of the Luminescence Genes", Journal of Bacteriology, 179(2): 557-562, Jan. 1997.
Official Action Dated Sep. 2, 2010 From the US Patent and Trademark Office Re. U.S. Appl. No. 10/565,240.
Official Action Dated Sep. 29, 2010 From the US Patent and Trademark Office Re.: U.S. Appl. No. 11/883,028.
Official Action Dated Oct. 27, 2010 From the US Patent and Trademark Office Re.: U.S. Appl. No. 12/890,668.
Communication Pursuant to Article 94(3) EPC Dated Aug. 5, 2010 From the European Patent Office Re. Application No. 05757567.2.
Communication Pursuant to Article 94(3) EPC Dated Aug. 6, 2010 From the European Patent Office Re.: Application No. 04714873.9.
Communication Pursuant to Article 94(3) EPC Dated Aug. 9, 2010 From the European Patent Office Re. Application No. 01982673.4.
Communication Pursuant to Rules 161(1) and 162 EPC Dated Aug. 25, 2010 From the European Patent Office Re. Application No. 08865081.7.
International Preliminary Report on Patentability Dated May 27, 2010 From the International Bureau of WIPO Re.: Application No. PCT/IL2008/001492.
International Preliminary Report on Patentability Dated May 27, 2010 From the International Preliminary Examining Authority Re.: Application No. PCT/IL2008/001678.
International Search Report Dated Mar. 2, 2005 From the International Searching Authority Re.: Application No. PCT/IL04/00661.
International Search Report Dated Feb. 7, 2006 From the International Searching Authority Re.: Application No. PCT/IL2005/001078.
International Search Report Dated Nov. 7, 2005 From the International Searching Authority Re.: PCT/IL2005/000801.
International Search Report Dated Nov. 9, 2004 From the International Searching Authority Re.: Application No. PCT/IL04/00571.
International Search Report Dated Sep. 10, 2009 From the International Searching Authority Re.: Application No. PCT/IL2008/001678.
International Search Report Dated Sep. 11, 2006 From the International Seaching Authority Re.: Application No. PCT/IL2006/000483.
International Search Report Dated Nov. 15, 2005 From the International Searching Authority Re.: PCT/IL2005/000719.
International Search Report Dated Feb. 16, 2005 From the International Searching Authority Re.: PCT/IL04/00194.
International Search Report Dated Jan. 17, 2003 From the International Searching Authority Re.: Application No. PCT/IL01/00992.
International Search Report Dated Feb. 21, 2006 From the International Searching Authority Re.: Application No. PCT/IL2005/000914.
International Search Report Dated Sep. 21, 2007 From the International Searching Authority Re.: PCT/IL2006/001487.
International Search Report Dated Dec. 27, 2001 From the International Searching Authority Re.: Application No. PCT/IL01/00443.
Notice of Allowance Dated Jun. 15, 2010 From the US Patent and Trademark Office Re. U.S. Appl. No. 11/940,996.
Office Action Dated Jul. 1, 2010 From the Israeli Patent Office Re.: Application No. 172724 and Its Translation Into English.
Office Action Dated Mar. 8, 2006 From the Israeli Patent Office Re.: Application No. 138314.
Office Action Dated May 15, 2008 From the Israeli Patent Office Re.: U.S. Appl. No. 10/916,380.
Office Action Dated Jul. 19, 2006 From the Israeli Patent Office Re.: Application No. 138314.
Office Action Dated Sep. 29, 2003 From the Israeli Patent Office Re.: Application No. 136232.
Official Action Dated Mar. 5, 2010 From the US Patent and Trademark Office Re.: U.S. Appl. No. 10/561,839.

Official Action Dated Sep. 10, 2010 From the US Patent and Trademark Office Re.: U.S. Appl. No. 11/646,317.
Official Action Dated Sep. 14, 2010 From the US Patent and Trademark Office Re.: U.S. Appl. No. 11/631,737.
Official Action Dated Aug. 17, 2010 From the US Patent and Trademark Office Re.: U.S. Appl. No. 10/561,839.
Official Action Dated Oct. 22, 2007 From the US Patent and Trademark Office Re.: U.S. Appl. No. 11/492,531.
Official Action Dated Jan. 28, 2010 From the US Patent and Trademark Office Re.: U.S. Appl. No. 10/492,531.
Response Dated Jun. 7, 2010 to Official Action of Mar. 5, 2010 From the US Patent and Trademark Office Re.: U.S. Appl. No. 10/561,839.
Response Dated Dec. 14, 2009 to Office Action of Jul. 14, 2009 From the Israel Patent Office Re.: Application No. 172724.
Response Dated Jun. 15, 2010 to Notice of Reason for Rejection of Mar. 30, 2010 From the Japanese Patent Office Re. Application No. 2006-502647.
Response Dated Sep. 21, 2010 to Communication Pursuant to Rules 161(1) and 162 EPC of Aug. 25, 2010 From the European Patent Office Re. Application No. 08865081.7.
Response Dated May 25, 2010 to Official Action of Jan. 28, 2010 From the US Patent and Trademark Office Re.: U.S. Appl. No. 10/492,531.
Response Dated Dec. 29, 2009 to Office Action of Sep. 2, 2009 From the Israel Patent Office Re.: Application No. 200559.
Response Dated Aug. 30, 2010 to Official Action of Jul. 13, 2009 From the US Patent and Trademark Office Re.: U.S. Appl. No. 11/660,783.
Supplementary European Search Report Dated Feb. 20, 2006 From the European Patent Office Re.: Application No. 04714873.9.
Supplementary European Search Report Dated Oct. 22, 2009 From the European Patent Office Re.: Application No. 04744911.1.
Supplementary European Search Report Dated Oct. 22, 2009 From the European Patent Office Re.: Application No. 04745001.0.
Supplementary European Search Report Dated Oct. 26, 2004 From the European Patent Office Re.: Application No. EP 01934272.
Translation of Notice of Reason for Rejection Dated Jul. 23, 2010 From the Japanese Patent Office Re.: Application No. 2006-502647.
Translation of Notice of Reason for Rejection Dated Nov. 27, 2007 From Japanes Patent Office Re.: Application No. 2003-538325.
Translation of Notice of Reason for Rejection Dated Mar. 30, 2010 From the Japanese Patent Office Re.: Application No. 2006-502647.
Written Opinion Dated Sep. 10, 2009 From the International Searching Authority Re.: Application No. PCT/IL2008/001678.
Written Opinion Dated Nov. 15, 2005 From the International Searching Authority Re.: Application No. PCT/IL2005/000719.
Darzynkiewicz et al. "Laser-Scanning Cytometry: A New Instrumentation With Many Applications", Experimental Cell Research, 249(1): 1-12, 1999. Abstract, p. 2, col. 2, §4-p. 4, col. 2, §2, p. 8, col. 1, §1-col. 2, §2.
Deutsch et al. "Microplate Cell-Retaining Methodology for High-Content Analysis of Individual Non-Adherent Unanchored Cells in a Population", Biomedical Microdevices, 8: 361-374, 2006.
Ducrée "Polymer Prototyping von mikrofluidischen Strukturen. Projekt", Insitut fur Mikrosystemtechnik, Albert-Ludwigs-Universitat Freiburg i. Br., IMTEK, 4 P., 2004. Retrieved From the Internet: http://images.google.com/imgres?imgurl=http://www.imtek.de/anwendungen/content/upload/vorlesung/133/133-03-14_prototyping_hydrophobic.jpg&imgrefurl=http://www.imtek.de/content/projekte.php%3Fls%3D3%26nr%3D133&h=299&w=429&.
Seahorse Bioscience "Designed for Scientists by Scientists. How the XF24 Extracellular Flux Analyzer Works", Product Description, Seahorse Bioscience, 4 P., 2008.
Seahorse Bioscience "XF24 Extracellular Flux Analyzer", Product Description, Seahorse Bioscience, 3 P., 2008.
Tixier et al. Catching and Attaching Cells Using an Array of Microholes, Abstract of the 2nd Conference of the Society for Chemistry and Micro Systems, p. 60, 2000.
Official Action Dated Dec. 22, 2010 From the US Patent and Trademark Office Re.: U.S. Appl. No. 11/883,028.

Proceeding Further With the European Patent Application Pursuant to Rule 70(2) EPC Dated Nov. 10, 2009 From the European Patent Office Re. Application No. 04745001.0.
Response Dated Jan. 2, 2011 to Proceeding Further With the European Patent Application Pursuant to Rule 70(2) EPC of Nov. 10, 2009 From the European Patent Office Re. Application No. 04745001.0.
Communication Pursuant to Rule 58 EPC or Rule 159 EPC Dated Nov. 24, 2010 From the European Patent Office Re. Application No. 10183774.8.
Response Dated Jan. 3, 2011 to Communication Pursuant to Rule 58 EPC or Rule 159 EPC of Nov. 24, 2010 From the European Patent Office Re. Application No. 10183774.8.
Official Action Dated Jan. 19, 2011 From the US Patent and Trademark Office Re.: U.S. Appl. No. 11/646,317.
Response Dated Jan. 24, 2011 to Official Action of Sep. 23, 2010 From the US Patent and Trademark Office Re.: U.S. Appl. No. 11/646,294.
Response Dated Jan. 12, 2011 to Office Action of Oct. 5, 2010 From the Israel Patent Office Re. Application No. 184818.
Official Action Dated Feb. 1, 2011 From the US Patent and Trademark Office Re.: U.S. Appl. No. 11/631,737.
Interview Summary Dated Feb. 11, 2011 From the US Patent and Trademark Office Re.: U.S. Appl. No. 11/883,028.
Response Dated Jan. 20, 2011 to Official Action of Oct. 27, 2010 From the US Patent and Trademark Office Re.: U.S. Appl. No. 12/890,668.
Response Dated Feb. 7, 2011 to Communication Pursuant to Article 94(3) EPC of Aug. 6, 2010 From the European Patent Office Re.: Application No. 04714873.9.
Office Action Dated Feb. 28, 2011 From the Israel Patent Office Re. Application No. 180568 and Its Translation Into English.
Official Action Dated Mar. 9, 2011 From the US Patent and Trademark Office Re.: U.S. Appl. No. 11/660,783.
Response Dated Mar. 22, 2011 to Official Action of Dec. 22, 2010 From the US Patent and Trademark Office Re.: U.S. Appl. No. 11/883,028.
Official Action Dated Mar. 16, 2011 From the US Patent and Trademark Office Re. U.S. Appl. No. 10/561,839.
Response Dated Feb. 17, 2011 to Communication Pursuant to Article 94(3) EPC of Aug. 9, 2010 From the European Patent Office Re. Application No. 01982673.4.
Cornell University "All About Birds: Optical Quality", Cornell University, 2 P., Oct. 3, 2010.
Office Action Dated Oct. 5, 2010 From the Israel Patent Office Re. Application No. 184818 and Its Translation Into English.
Official Action Dated Nov. 1, 2010 From the US Patent and Trademark Office Re.: U.S. Appl. No. 11/883,028.
Official Action Dated Dec. 9, 2010 From the US Patent and Trademark Office Re. U.S. Appl. No. 10/565,240.
Official Action Dated Sep. 23, 2010 From the US Patent and Trademark Office Re.: U.S. Appl. No. 10/492,531.
Official Action Dated Sep. 23, 2010 From the US Patent and Trademark Office Re.: U.S. Appl. No. 11/646,294.
Response Dated Oct. 4, 2010 to Official Action of Sep. 2, 2010 From the US Patent and Trademark Office Re. U.S. Appl. No. 10/565,240.
Response Dated Nov. 8, 2010 to Official Action of Sep. 10, 2010 From the US Patent and Trademark Office Re.: U.S. Appl. No. 11/646,317.
Response Dated Oct. 10, 2010 to Notice of Reason for Rejection of Jul. 23, 2010 From the Japanese Patent Office Re.: Application No. 2006-502647.
Response Dated Nov. 15, 2010 to Official Action of Nov. 1, 2010 From the US Patent and Trademark Office Re.: U.S. Appl. No. 11/883,028.
Response Dated Dec. 16, 2010 to Official Action of Aug. 17, 2010 From the US Patent and Trademark Office Re.: U.S. Appl. No. 10/561,839.
Response Dated Dec. 20, 2010 to Official Action of Sep. 23, 2010 From the US Patent and Trademark Office Re.: U.S. Appl. No. 10/492,531.
Response Dated Nov. 30, 2010 to Communication Pursuant to Article 94(3) EPC of Aug. 5, 2010 From the European Patent Office Re. Application No. 05757567.2.

Ducrée "Polymer Prototyping von mikrofluidischen Strukturen. Projekt", Insitut fur Mikrosystemtechnik, Albert-Ludwigs-Universität Freiburg i. Br., IMTEK, 4 P., 2004. Retrieved From the Internet: http://images.google.com/imgres?imgurl=http://www.imtek.de/anwendungen/content/upload/vorlesung/133/133-03-14_prototyping_hydrophobic.jpg&imgrefurl=http://www.imtek.de/content/projekte. php%3Fls%3D3%26nr%3D133&h=299 & w=429&.

Response Dated Feb. 23, 2011 to Official Action of Jan. 19, 2011 From the US Patent and Trademark Office Re.: U.S. Appl. No. 11/646,317.

Invitation Pursuant to Article 94(3) and Rule 71(1) EPC Dated Apr. 8, 2011 From the European Patent Office Re. Application No. 01982673.4.

Notice of Allowance Dated Mar. 31, 2011 From the US Patent and Trademark Office Re.: U.S. Appl. No. 12/890,668.

Official Action Dated Mar. 31, 2011 From the US Patent and Trademark Office Re.: U.S. Appl. No. 10/492,531.

Invitation Pursuant to Rule 63(1) EPC Dated May 3, 2011 From the European Patent Office Re. Application No. 10183774.8.

Official Action Dated Apr. 22, 2011 From the US Patent and Trademark Office Re.: U.S. Appl. No. 11/646,294.

Notification of European Publication Number and Information on the Applicaiton of Article 67(3) EPC Dated May 18, 2011 From the European Patent Office Re. Application No. 10183774.8.

Official Action Dated May 23, 2011 From the US Patent and Trademark Office Re.: U.S. Appl. No. 11/646,317.

Response Dated May 31, 2011 to Invitation Pursuant to Article 94(3) and Rule 71(1) EPC of Apr. 8, 2011 From the European Patent Office Re. Application No. 01982673.4.

Notice of Allowance Dated Jun. 9, 2011 From the US Patent and Trademark Office Re.: U.S. Appl. No. 11/883,028.

Response Dated Jun. 1, 2011 to Official Action of Feb. 1, 2011 From the US Patent and Trademark Office Re.: U.S. Appl. No. 11/631,737.

Response Dated Jun. 9, 2011 to Official Action of Mar. 9, 2011 From the US Patent and Trademark Office Re.: U.S. Appl. No. 11/660,783.

Response Dated Jun. 9, 2011 to Official Action of Dec. 9, 2010 From the US Patent and Trademark Office Re. U.S. Appl. No. 10/565,240.

Response Dated Jun. 29, 2011 to Official Action of Mar. 31, 2011 From the US Patent and Trademark Office Re.: U.S. Appl. No. 10/492,531.

Response Dated Jul. 12, 2011 to Official Action of Mar. 16, 2011 From the US Patent and Trademark Office Re. U.S. Appl. No. 10/561,839.

Response Dated Jun. 28, 2011 to Invitation Pursuant to Rule 63(1) EPC of May 3, 2011 From the European Patent Office Re. Application No. 10183774.8.

European Search Report and the European Search Opinion Dated Aug. 1, 2011 From the European Patent Office Re. Application No. 10183774.8.

Gonzalez et al. "Cell-Based Assays and Instrumentation for Screening Ion-Channels Targets", Drug Discovery Today, DDT, XP001026838, 4(9): 431-439, Sep. 1, 1999.

Communication Pursuant to Article 94(3) EPC Dated Aug. 4, 2011 From the European Patent Office Re. Application No. 08865081.7.

Official Action Dated Jul. 21, 2011 From the US Patent and Trademark Office Re. U.S. Appl. No. 12/712,232.

Notice of Non-Compliant Amendment Dated Aug. 24, 2011 From the US Patent and Trademark Office Re. U.S. Appl. No. 10/565,240.

Response Dated Aug. 4, 2011 to Official Action of May 23, 2011 From the US Patent and Trademark Office Re.: U.S. Appl. No. 11/646,317.

Response Dated Aug. 17, 2011 to Office Action of Apr. 12, 2011 From the Israel Patent Office Re.: Application No. 173170.

Response Dated Aug. 22, 2011 to Official Action of Apr. 22, 2011 From the US Patent and Trademark Office Re.: U.S. Appl. No. 11/646,294.

Response Dated Sep. 6, 2011 to Notice of Non-Compliant Amendment of Aug. 24, 2011 From the US Patent and Trademark Office Re. U.S. Appl. No. 10/565,240.

Official Action Dated Sep. 22, 2011 From the US Patent and Trademark Office Re.: U.S. Appl. No. 11/646,294.

Official Action Dated Aug. 31, 2011 From the US Patent and Trademark Office Re.: U.S. Appl. No. 11/660,783.

Communication Pursuant to Article 94(3) EPC Dated Aug. 29, 2011 From the European Patent Office Re. Application No. 04745001.0.

* cited by examiner

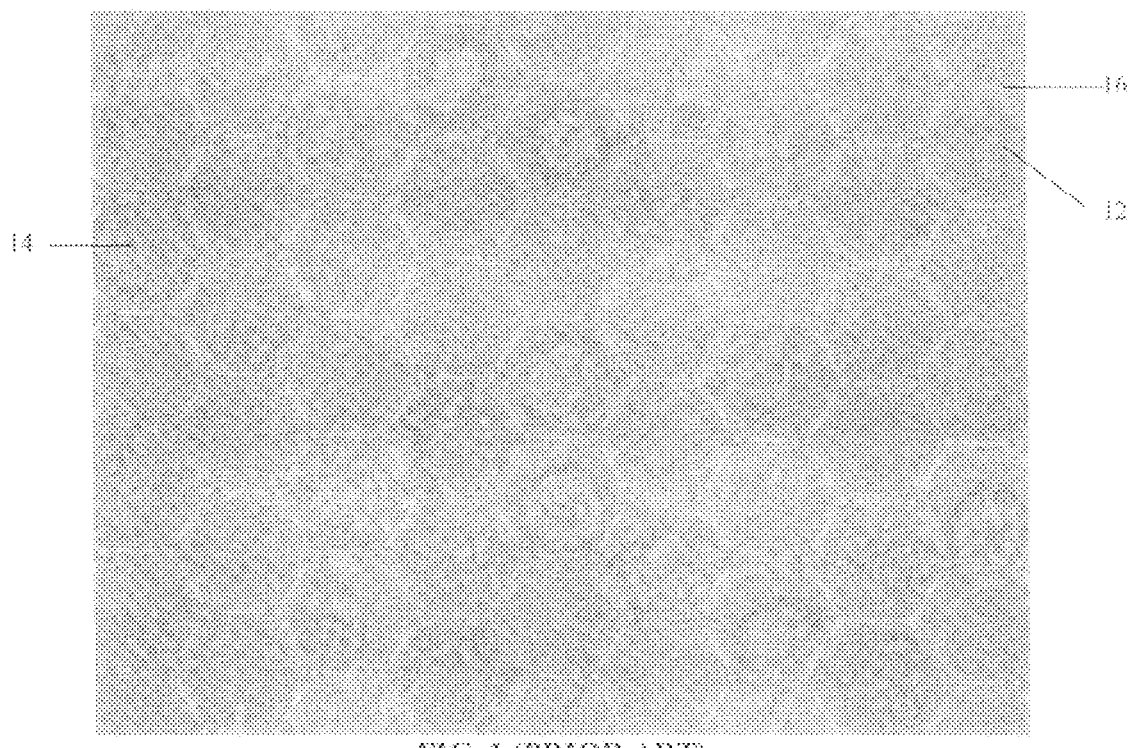
FIG. 1 (PRIOR ART)

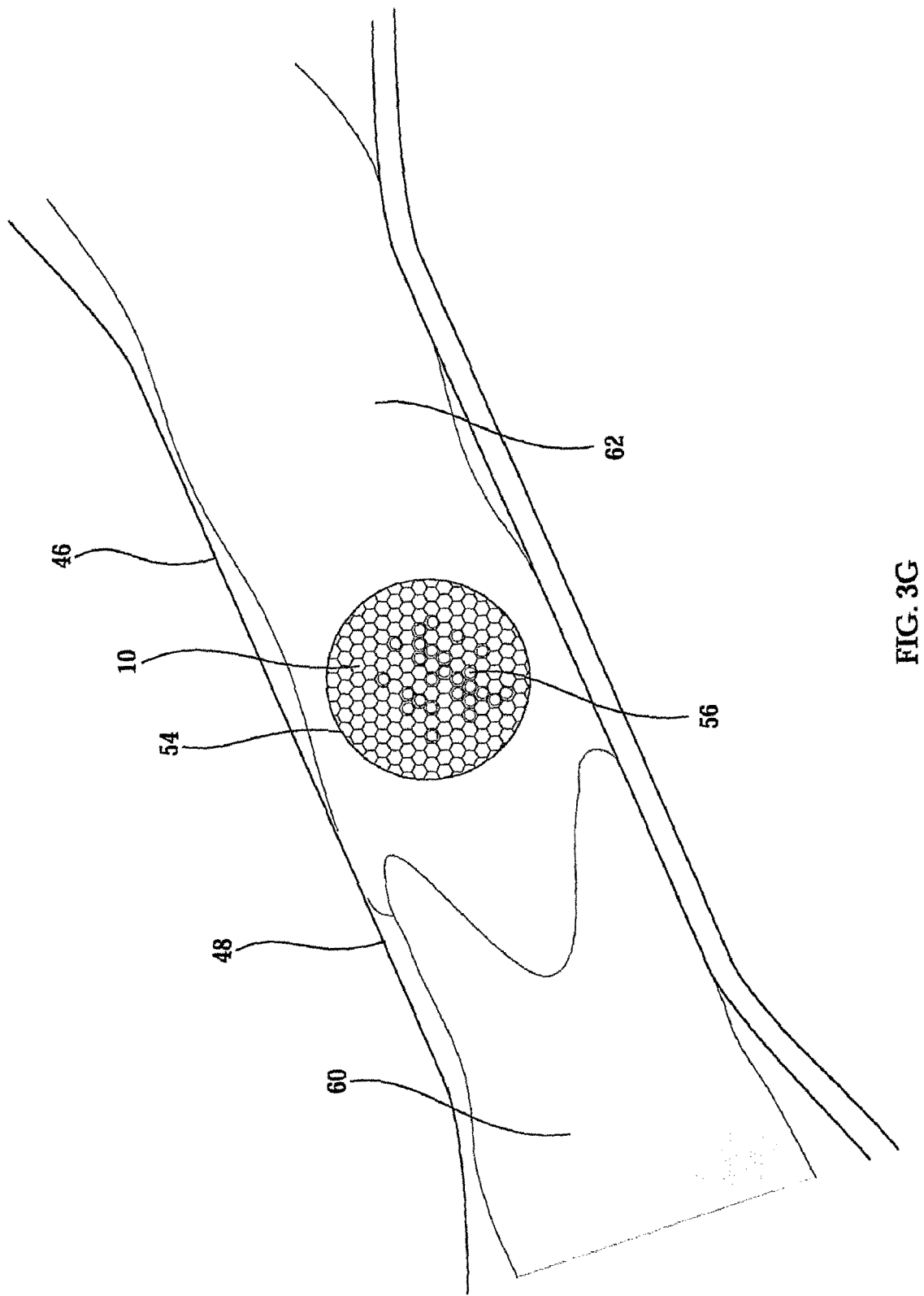

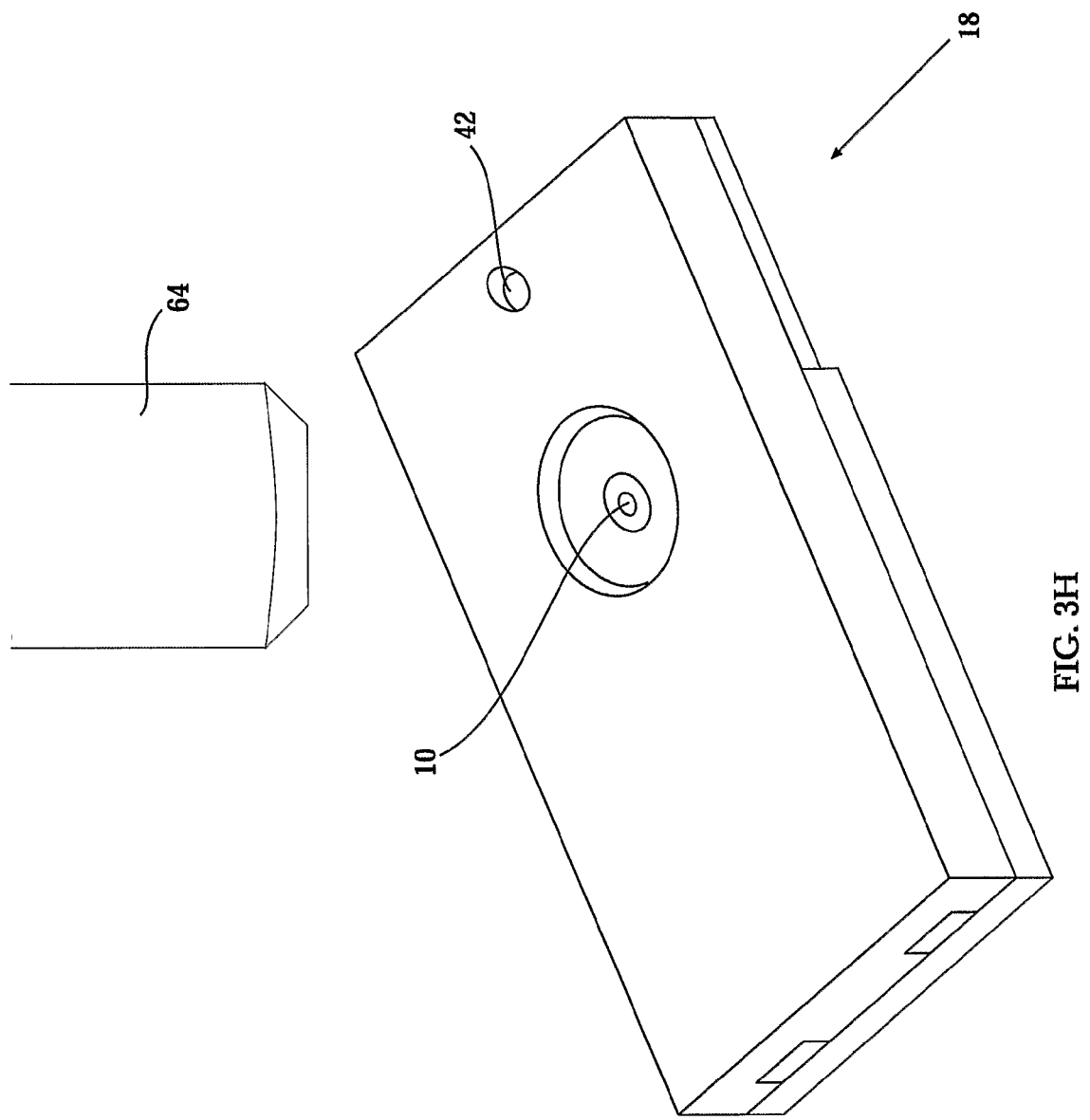

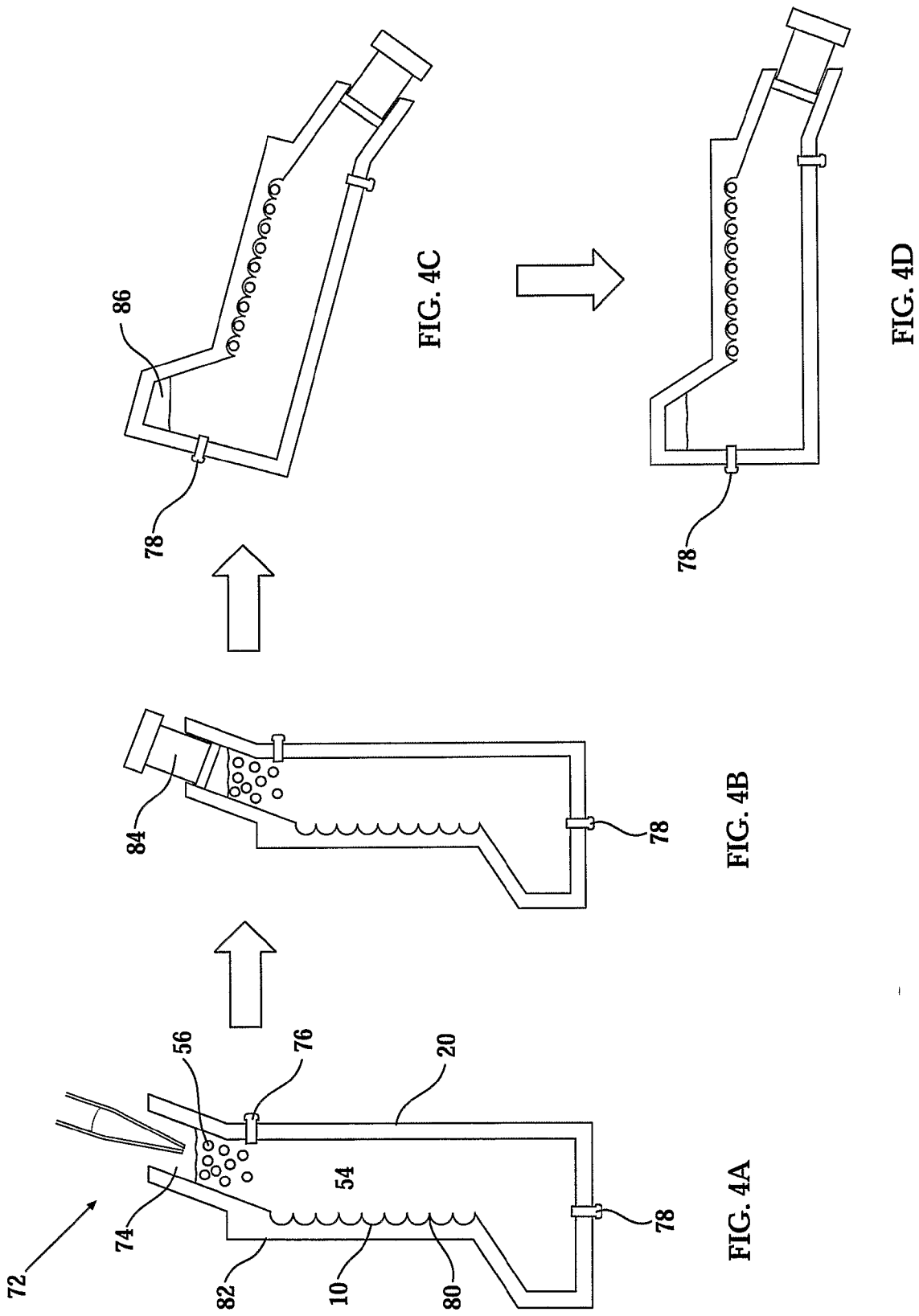

METHOD FOR STUDYING FLOATING, LIVING CELLS

RELATED APPLICATIONS

This Application is a National Phase of PCT Patent Application No. PCT/IL2006/000483 having International filing date of Apr. 20, 2006, which claims the benefit of U.S. Provisional Patent Application Nos. 60/734,287 filed on Nov. 8, 2005; 60/734,286 filed on Nov. 8, 2005 and 60/732,827 filed on Nov. 3, 2005. The contents of the above Applications are all incorporated herein by reference.

FIELD AND BACKGROUND OF THE INVENTION

The present invention relates to the field of cellular biology and more particularly, to a device and method for the study of cells. Specifically, the present invention is of a device including a picowell array for the study of cells as well as of a device configured for the study of cells that float in aqueous media.

Combinatorial methods in chemistry, cellular biology and biochemistry are essential for the near simultaneous preparation of multitudes of active entities such as molecules. Once such a multitude of molecules is prepared, it is necessary to study the effect of each one of the active entities on a living organism.

The study of the effects of stimuli such as exposure to active entities on living organisms is preferably initially performed on living cells. Since cell-functions include many interrelated pathways, cycles and chemical reactions, the study of an aggregate of cells, whether a homogenous or a heterogeneous aggregate, does not provide sufficiently detailed or interpretable results: rather a comprehensive study of the biological activity of an active entity may be advantageously performed by examining the effect of the active entity on a single isolated living cell. Thus, the use of single-cell assays is one of the most important tools for understanding biological systems and the influence thereupon of various stimuli such as exposure to active entities.

The combinatorial preparation of a multitudes of active entities coupled with the necessity of studying the effect of each one of the active entities on living organisms using single-cell assays, requires the development of high-throughput single live cell assays. There is a need for the study of real-time responses to stimuli in large and heterogeneous cell populations at an individual cell level. In such studies it is essential to have the ability to define multiple characteristics of each individual cell, as well as the individual cell response to the experimental stimulus of interest.

In the art, various methods and devices for studying living cells are known.

One method of studying cells involves placing cells on a bottom surface of a vessel and observing the behavior of the cell in response to stimuli. Typically used vessels include slides with recesses and Petri dishes. To allow for simultaneous study of distinct groups of cells exposed to similar or different stimuli, multiwell plates are most commonly used. A multiwell plates is substantially a group of standard sized individual vessels physically associated in a standard way allowing for simplified simultaneous or sequential studies of separated groups of cells. Multiwell plates having 6, 12, 24, 48, 96, 384 or even 1536 wells on a standard ca. 8.5 cm by ca. 12.5 cm footprint are well known in the art. Such multiwell plates are provided with an 2n by 3n array of rectangular packed wells. The diameter of the wells of a plate depends on the number of wells and is generally greater than about 250 microns (for a 1536 well plate). The volume of the wells depends on the number of wells and the depth thereof but generally is greater than $5 \times 10^{-6}$ liter (for a 1536 well plate). The standardization of the multiwell plate format is a great advantage for researchers, allowing the use of standardized products including robotic handling devices, automated sample handlers, sample dispensers, plate readers, observation components, plate washers, software and such accessories as multifilters.

When a vessel having a planar bottom surface is used to study cells, the cells are most often studied as a group having an aggregate of properties of the individual cells. Since the cells are studied as a group, in such studies the identity of individual cells is not important. Such studies are of limited utility due to the fact that naturally occurring cell populations are rarely homogenous and often it is the heterogenity and the differences of behavior of cells that is of interest.

Efforts have been made to use vessels having a planar bottom surface to study cells as individuals but such efforts are plagued with many difficulties. A first difficulty is that cells have a tendency to clump together in variably sized groups at random locations, and often stack one on top of the other. The clumping and stacking of cells together makes it virtually impossible to delineate the borders of one cell from another, see discussion in unpublished PCT Patent Application No. IL2005/000719 of the inventor, rendering it virtually impossible to identify which cell has a given behavior. Further, the fact that cells are randomly distributed over a featureless surface coupled to the fact that cells often move due to currents makes it virtually impossible to definitely identify a specific cell without continuous observation of the cell. These factors further render high-throughput imaging (for example for morphological studies) challenging as acquiring an individual cell and focusing thereon is extremely difficult. Such variability in location also makes high-throughput signal processing (for example, detection of light emitted by a single cell through fluorescent processes) challenging as light must be gathered from the entire area of the well, decreasing the signal to noise ratio. Further, a cell held in a well of a multiwell plate well can be physically or chemically manipulated (for example, isolation or movement of a single selected cell or single type of cell, changing media or introducing active entities) only with difficulty. Further, addition of a reagent to a well or even the slightest incidental jostling of the vessel causes cells held therein to move randomly leading to the loss of identity of individual cells and rendering experiments difficult to perform, limited in scope and slow. Further, cell behavior is influenced by contact with other cells. If, to avoid the above difficulties, a multiwell plate holds only one cell per well, loading of the plate is very low (about 1536 cells in 65 $cm^2$, or 24 cells $cm^{-2}$). Thus, flat-bottomed vessels are in general only suitable for the study of homogenous or heterogenous aggregates of cells as a group.

Flat-bottomed vessels are also unsuitable for the study of cells undergoing apoptosis. It is known to study biological processes by exposing a monolayer of cells adhering to the bottom of a flat-bottomed vessel to a stimulus that initiates apoptosis. Once a cell begins apoptosis, the adhesion of the cell to the bottom of the vessel is no longer sufficient: the cell detaches from the bottom and is carried away by incidental fluid currents in the vessel. The cell is no longer observable and its identity lost.

Flat-bottomed vessels are also unsuitable for the study of non-adhering cells. Just as cells undergoing apoptosis, in flat-bottomed vessels non-adhering cells can be studied as individuals only with difficulty. This is a major disadvantage as non-adhering cells are crucial for research in drug discovery, stem cell therapy, cancer and immunological diseases detection, diagnosis and therapy. For example, blood contains seven heterogeneous types of non-adherent cells, all which perform essential functions, from carrying oxygen to providing immunity against disease.

It is known to study cells in a vessel having a planar bottom surface provided with an array of cell-localizing features. In such vessels, each cell is held in a specific location that is individually addressable allowing the identity of a given cell to be retained even without continuous observation, see for example Mrksich and Whitesides, *Ann. Rev. Biophys. Biomol. Struct.* 1996, 25, 55-78; Craighead et al., *J. Vac. Sci. Technol.* 1982, 20, 316; Singhvi et al., *Science* 1994, 264, 696-698; Aplin and Hughes, *Analyt. Biochem.* 1981, 113, 144-148, U.S. Pat. No. 4,729,949, U.S. Pat. No. 5,324,591, U.S. Pat. No. 6,103,479 and PCT Patent Application No. US99/04473 published as WO 99/45357. Many such devices deform the shape of the cells or require cell binding or adhesion to a vessel surface, adversely effecting the results of performed studies In PCT patent applications IL2001/00992 published as WO2003/035824 ("Interactive transparent individual cells biochip processor"), IL2004/000571 published as WO2004/113492 ("Improved materials for constructing cell-chips, cell-chip covers, cell-chip coats, processed cell-chips and uses thereof"), IL2004/000194 published as WO2004/077009 ("A method and device for manipulating individual small objects"), IL2004/000661 published as WO2005/007796 ("Improved multiwell plate"), and unpublished IL2005/000801 ("Device for the study of cells") all of the inventor or applicant, are provided picowell-bearing devices. A picowell-bearing device is a device for the study of cells that has at least one picowell-bearing component. A picowell-bearing component is a component having at least one, but generally a plurality of picowells, each picowell configured to hold at least one cell. In such devices, individual cells are generally held in a substantially natural state, preferably unadhered, in individual adressable picowells, preferably each cell alone in an individual picowell. In the art, a picowell-bearing component of a picowell-bearing device is often a chip, a plate or other substantially planar component. Such a component is termed a "carrier".

A picowell, as the name suggests, is small well-shaped feature (including cavities, dimples, depressions, tubes and enclosures) configured to localize cells in well-defined locations on the bottom surface of a vessel. Since cells range in size from about 1 microns to about 100 (or even more) microns diameter there is no single picowell size that is appropriate for holding a single cell of any type. That said, the dimensions of the typical individual picowell in the picowell-bearing components known in the art have dimensions of between about 1 microns up to about 200 microns or even up to about 250 microns, depending on the exact implementation. For example, a device designed for the study of single isolated 20 micron cells typically has picowells of dimensions of about 20 microns. In other cases, larger picowells are used to study the interactions of a few cells held together in one picowell. For example, a 200 or even 250 micron picowell is recognized as being useful for the study of the interactions of two or three cells, see PCT Patent Application No. IL01/00992 published as WO 03/035824.

A feature that increases the utility of picowell-bearing devices is that each individual picowell is individually addressable. By individual addressability is meant that each picowell is identifiable from amongst the other picowells of a picowell array allowing each picowell to be registered, found, observed or studied as desired. For example, while cells are held in picowells of a picowell-bearing component, each cell is characterized and the respective picowell wherein that cell is held is noted. When desired, the observation component of the picowell-bearing device is directed to observe the picowell where a specific cell is held. One method of implementing individual addressability is by the use of fiducial points or other features (such as signs or labels), generally on the picowell-bearing component. Another method of implementing individual addressability is by arranging the picowells in a picowell-array and finding a specific picowell by counting. Another method of implementing individual addressability is by providing a dedicated observation component for each picowell. Another method is by observing a whole picowell array substantially in its entirety.

An additional feature that increases the utility of picowell-bearing devices is that the picowells of the picowell array are close together, preferably being juxtaposed, that is, the area occupied by a picowell-array is substantially entirely made up of picowells with little or no inter picowell area, see FIG. 1, a reproduction of a photograph of a picowell-array from above, such as described in PCT Patent Application No. IL01/00992. In FIG. 1 is seen a part of a hexagonally packed picowell array 10 including a plurality of hexagonal picowells 12, some holding living cells 14. It is seen that the inter picowell areas 16 make up only a minor percentage of the total area of picowell-array 10. Preferably the wells are knife-edged, that is the interwell surfaces are substantially non-existent. Such a feature allows simple loading of cells by sedimentation, allows very high-loading (expressed in units of cells per unit area), avoids stacking of cells, and clearly separates and prevents physical contact between cells held in adjacent picowells 12.

An additional feature that increases the utility of embodiments of picowell-bearing devices is the use of optical properties of the picowell array such as of the picowell bottom surface or picowell walls for automatic delineation of picowell borders in an image of the picowell array, allowing high throughput image acquisition, image processing and experimental analysis as described in PCT patent application IL2005/000719 published as WO2006/003664 of the inventor.

The use of the picowell-bearing devices described above allows large number of cells to be studied as individuals. In embodiments of picowell-bearing devices such as described in PCT patent applications IL2001/00992 published as WO2003/035824, complex experiments involving serial addition of reagents and the like are performed with dedicated microfluidics systems including flow generators such as pumps or syringes. In embodiments described therein, a picowell array is located in a substantially sealed chamber, the chamber in fluid communication with at least one fluid inlet and at least one fluid outlet. In embodiments, cells are loaded onto the picowell array by sedimentation: a moveable wall of the chamber in which the picowell array is located is moved, a solution of cells is introduced through the consequent opening, the cells allowed to settle in the picowells, and the moveable wall replaced so as to reseal the chamber.

Despite the unparalleled utility of such picowell-bearing devices, such devices have a number of limitations. A first limitation is that the devices are generally difficult to use by an unskilled person and are not completely suitable for integration with a robotics system for automatised use. A second limitation is that the devices are relatively complex to assemble. A third limitation is that the flow rate of liquids through picowell-array holding chamber is relatively limited. If a flow rate is too high, pressure in the chamber increases to the point where the lid is lifted upwards, allowing leakage of liquid from under the lid, or even detached. In embodiments this limitation is overcome by permanently securing all chamber walls, for example by using an adhesive so that no wall is moveable. In such embodiments, cells are loaded onto the picowell array through a fluid inlet, a time consuming step that is less efficient than loading of the picowell array by cell sedimentation.

Many of the above limitations are overcome by the teachings of unpublished PCT patent application IL2005/000801 of the inventor. In embodiments of the device taught therein, a picowell array is located inside a depression on a plateau, the plateau provided with a moveable wall that is substantially a lid, the space between the lid and the plateau defining a capillary channel. For use, cells are loaded by sedimentation when the lid is open and the lid subsequently shut. Liquid added at one end of the lid is transported past the picowell array through the capillary channel defined between the lid and the plateau. Embodiments of the device are remarkably simple to manufacture and simple for use, even by unskilled practitioners. A disadvantage of embodiments of such devices is that the flow rate and total volume of liquid that can be added is limited.

An additional disadvantage of the devices known in the art including the discussed above is that the devices are not exceptionally suited for the studies of cells, such as adipocytes, that have a density lower than the aqueous medium in which the cells are found and therefore float.

It would be highly advantageous to have a device for the study of cells not having at least some of the disadvantages of the prior art.

SUMMARY OF THE INVENTION

Embodiments of the present invention successfully addresses at least some of the shortcomings of the prior art by providing a picowell-bearing device for the study of cells.

Aspects of the present invention provide a picowell-bearing device for the study of floating cells and methods of using the device, including downwardly facing picowells inside a chamber (generally on the bottom surface of a top wall of the chamber e.g., the ceiling of the chamber). Cells that are less dense than a medium found in the chamber float upwards to contact the bottom surface and to enter the picowells, in a manner analogous to non-floating cells that settle into picowells disposed on a top surface of a bottom wall constituting a floor of a chamber of a picowell-bearing device as known in the art.

Aspects of the present invention provide device for the study of cells including at least one picowell in a chamber, the chamber having at least one moveable wall and a force applicator configured to removeably apply a substantially uniformly distributed force around the periphery of the moveable wall in a direction to retain the moveable wall secured to the chamber. In embodiments, such a device allows introduction of a continuous flow of liquids and active entities such as nutrients and reagents at relatively high pressures with a reduced chance of leakage. Embodiments of a device implementing this aspect of the present invention include microincubators where a plurality of living cells are held in individual picowells.

Thus, according to the teachings of the present invention there is provided a method of studying floating living cells, comprising: a) confining living cells floating in an aqueous medium to picowells located on a bottom surface of a top wall of a chamber; and b) observing the living cells. In embodiments of the present invention, the picowells are arrayed in a picowell array. In embodiments of the present invention, the top wall is fashioned from a substantially transparent material in the vicinity of the picowells and the observing is through the top wall. In embodiments of the present invention, during the observing, an active entity is introduced into the chamber.

According to the teachings of the present invention there is also provided a picowell-bearing device for the study of living cells, comprising: a) a chamber; b) a picowell-bearing component constituting a top wall of the chamber; and c) at least one picowell (preferably a plurality of picowells, preferably or a picowell array) inside the chamber on a bottom surface of the top wall. In embodiments of the present invention the bottom surface is substantially planar. In embodiments of the present invention, the at least one picowell is located in a hollow on the bottom surface of the top wall. In embodiments of the present invention, the at least one picowell is a feature on the bottom surface of the top wall.

In embodiments, a device of the present invention comprises a second picowell-bearing component constituting a bottom wall of the chamber having at least one picowell (preferably a plurality of picowells, preferably or a picowell array) inside the chamber on the top surface of the bottom wall. In embodiments of the present invention the top surface is substantially planar. In embodiments of the present invention, the at least one picowell is located in a hollow on the top surface of the bottom wall. In embodiments of the present invention, the at least one picowell is a feature on the top surface of the bottom wall.

In embodiments of the present invention, the device further comprises at least one fluid inlet in fluid communication with the chamber, preferably configured for introduction of a liquid into the chamber. In embodiments of the present invention, a fluid inlet is a capillary channel.

In embodiments of the present invention, the device further comprises at least one fluid outlet in fluid communication with the chamber. In embodiments of the present invention, a fluid outlet is configured for removal of a liquid from the chamber. In embodiments of the present invention, a fluid outlet is a capillary channel. In embodiments of the present invention, a fluid outlet is configured for removal of a gas from the chamber, for example, air trapped in the chamber, especially in the at least one picowell, when liquid is introduced into the chamber.

In embodiments, the chamber of a device of the present invention is defined, in part, by a device body. In embodiments, the device body is a picowell-bearing component. In embodiments, the picowell-bearing component and the device body are distinct components.

In embodiments of the present invention, the device further comprises a base constituting a bottom wall of the chamber. In embodiments of the present invention, the base is configured to contact a bottom surface of the device body substantially in parallel to the bottom surface of the device body and wherein the at least one picowell is located in a hollow on the bottom surface of the device body. In embodiments of the present invention, a contact region between the bottom surface of the device body and the base constitutes at least one capillary channel in fluid communication with the chamber. In embodiments of the present invention, a contact region between the bottom surface of the device body and the base constitutes at least two capillary channels in fluid communication with the chamber. In embodiments of the present invention, the bottom surface of the device body comprises a plateau in which the hollow is located, wherein at least part of the plateau constitutes at least part of the capillary channel.

In embodiments, a device of the present invention includes a hole through the bottom surface of the device body in fluid communication with the base. In embodiments of the present invention, the hole constitutes a liquid reservoir in fluid communication with the capillary channel. In embodiments of the present invention, in at least one position of the bottom surface, the base protrudes relative to the device body constituting a liquid reservoir in capillary communication with a capillary channel.

In embodiments of the present invention, the base is removable, that is, is separable from the device body. In embodiments of the present invention, the base is moveable relative to the device body. In embodiments of the present invention, the base is moveable substantially in parallel to the bottom surface of the device body.

In embodiments of the present invention, the base is slidingly associated with the device body. In embodiments of the present invention, the device body comprises two rails, the at least one picowell is located between the two rails and the base is slidingly associated with the two rails. In embodiments of the present invention, the at least one picowell is located in a hollow between the two rails. In embodiments of the present invention, the base and an area of the device body between the two rails substantially define a capillary channel. In embodiments of the present invention, the rails are substantially grooves in walls protruding from the bottom surface.

In embodiments of the present invention, at least one picowell is porous so as to allow fluid flow therethrough. In embodiments of the present invention, the device comprises an upper chamber in fluid communication with the chamber through the pores of the picowells.

In embodiments of the present invention, the device body is fashioned from a substantially transparent material in the vicinity of the at least one picowell allowing observation of cells held in the picowell therethrough.

According to the teachings of the present invention there is also provided a method of studying floating living cells, comprising: a) providing a chamber including at least one opening, a top wall with a bottom surface and at least one picowell (preferably a plurality of picowells, preferably or a picowell array) on the bottom surface; b) introducing an medium into the chamber through an opening; c) introducing a living cell (preferably a plurality of living cells) of a first type into the chamber through the opening; and d) orienting the chamber so that the bottom surface faces substantially downwards, whereby the at least one living cell floats upwards in the medium to be held in a picowell.

Generally, the living cell or cells of the first type are introduced into the chamber together with the medium. In embodiments of the present invention, the cells and the medium are introduced separately.

In embodiments of the present invention, the medium is introduced when the chamber is already oriented so that the bottom surface faces substantially downwards.

In embodiments of the present invention, the medium is first introduced and subsequently the chamber oriented so that the bottom surface faces substantially downwards. In embodiments of the present invention, subsequent to introduction of the medium into the chamber, the opening through which the medium is introduced is substantially closed with a closing component. In embodiments, the closing component constitutes a part of a fluid inlet in fluid communication with the chamber.

In embodiments of the present invention, the chamber includes a bottom wall with a top surface and at least one picowell (preferably a plurality of picowells, preferably or a picowell array) on the top surface and the method further comprises: e) introducing a living cell of a second type into the chamber through a the opening, the living cell of the second type being denser than the medium whereby the at least one living cell of the second type settles into a the picowell on the top surface for study.

Generally, the living cell or cells of the second type are introduced into the chamber together with the medium. In embodiments of the present invention, the cells of the second type and the medium are introduced separately.

In embodiments of the present invention, the living cells that are held in the picowells are observed, for example, to study cell development or reaction to stimuli such as contact with an active entity. To this end, in embodiments of the present invention, the top wall is fashioned from a substantially transparent material in the vicinity of the at least one picowell and the observing is through the top wall, through the bottom wall, or through both the top and bottom wall.

According to the teachings of the present invention there is also provided a picowell-bearing device for the study of living cells, comprising: a) a chamber having at least one picowell (preferably a plurality of picowells, preferably or a picowell array) on an internal surface and at least one moveable wall; b) a liquid inlet into the chamber; c) a liquid outlet from the chamber; d) a force applicator configured to removeably apply a substantially uniformly distributed force around the periphery of the moveable wall in a direction to retain the moveable wall secured to the chamber.

In embodiments of the present invention, the at least one picowell is located in a hollow on the internal surface. In embodiments of the present invention, the at least one picowell is a feature on the internal surface.

In embodiments of the present invention, the internal surface is an upper surface of a wall (e.g., the bottom wall) of the chamber. In embodiments of the present invention, the internal surface is a bottom surface of a wall (e.g., the top wall) of the chamber, substantially as described hereinabove.

In embodiments of the present invention, the moveable wall includes the at least one picowell. In embodiments of the present invention, the at least one picowell is disposed on a non-moveable, wall.

In embodiments the force applied is a magnetic force. In such embodiments, the force applicator generally includes a magnet, preferably a magnet at least part of which is located in proximity of the periphery of the moveable wall.

In embodiments of the present invention, the force applicator includes threads on the moveable wall. For example, in embodiments threads are located on the edge of a disk-shaped moveable wall and matching threads provided on the sides of an opening into the chamber so that the moveable wall can be screwed in and out of the opening.

In embodiments of the present invention, the force applicator includes a rigid force distributor contacting the periphery of the moveable wall.

In embodiments of the present invention, the device further comprises a flow generator, e.g., a syringe, a pump, a peristaltic pump) functionally associated with the liquid inlet. Preferably, such a flow generator is a variable flow generator configured to vary the rate of flow of liquids through the liquid inlet.

In embodiments of the present invention, the device further comprises a liquid temperature controller, to cool, to heat or both, medium in the chamber. In embodiments of the present invention, such a liquid temperature controller is functionally associated with the flow generator and/or the chamber and/or the liquid inlet and/or the liquid outlet.

In embodiments of the present invention, a device is functionally associated with a pH-determining component for determining the pH of liquid entering the device through a liquid inlet, in the chamber or exiting the device from the liquid outlet. In embodiments of the present invention, a device is functionally associated with a gas content determining component for determining the content of a gas, such as carbon dioxide or oxygen, in a liquid entering the device through a liquid inlet, in the chamber or exiting the device from the liquid outlet.

In embodiments of the present invention, a device is functionally associated with a component for varying the content of a gas, such as carbon dioxide or oxygen, in a liquid entering the device through a liquid inlet.

In embodiments of the present invention, the device body is fashioned from a substantially transparent material in the vicinity of the at least one picowell allowing observation of cells held in the picowell therethrough.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 (prior art) is a reproduction of a photograph of a cell-populated well-array of a device body of a picowell-bearing device of PCT Patent Application No. IL01/00992;

FIGS. 3A-3H depict the use of the device of FIG. 2A-2E;

FIGS. 4A-4D depict an embodiment of a device of the present invention including a picowell array on a bottom surface of a fixed top wall of a chamber;

EMBODIMENTS OF THE INVENTION

Figure 2A:
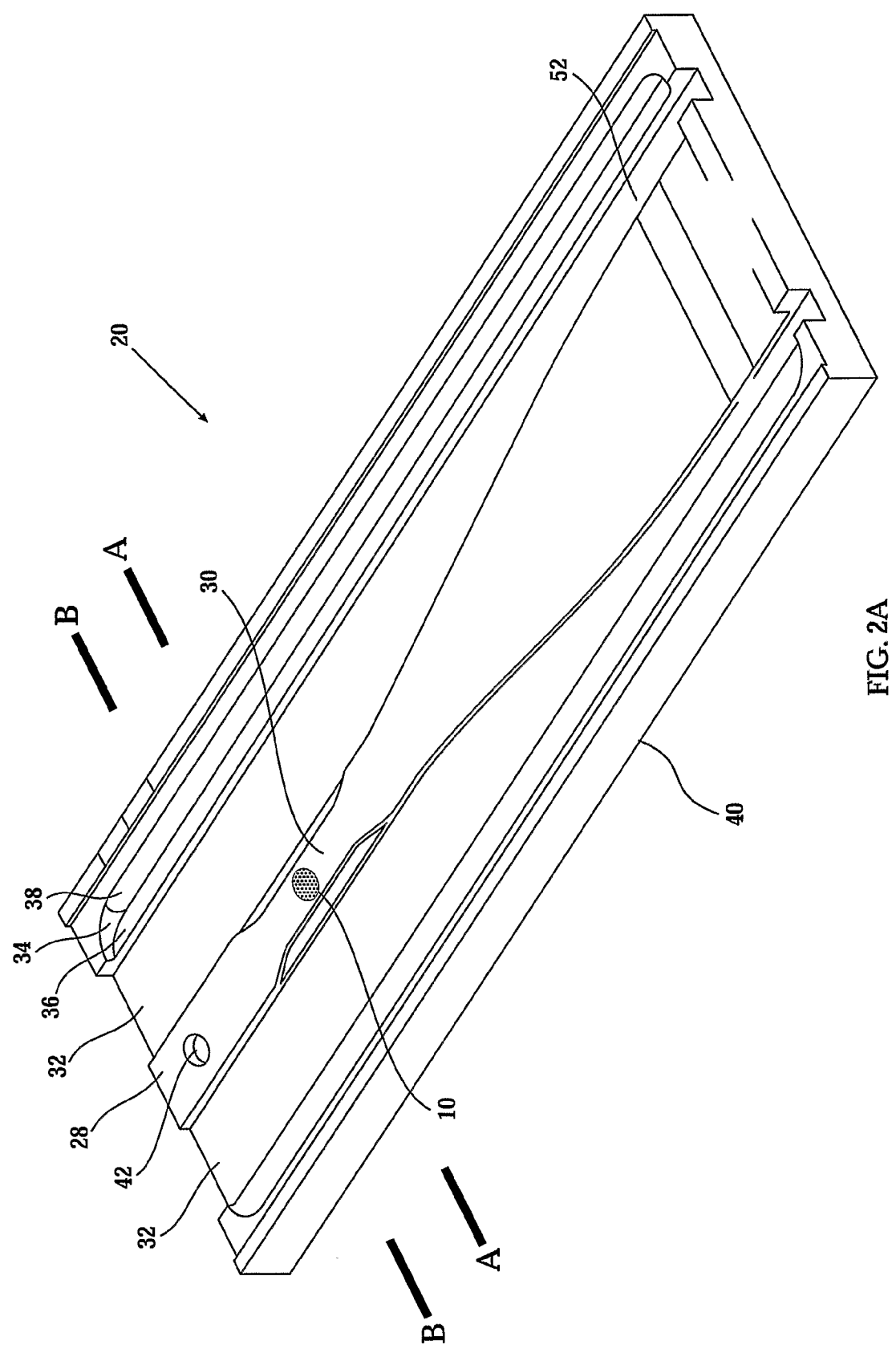
FIGS. 2A-2E depict an embodiment of a device of the present invention including a picowell array on a bottom surface of an upper wall of a chamber, and capillary channels and a liquid inlet hole in fluid communication with the picowell array.
Figure 2B:
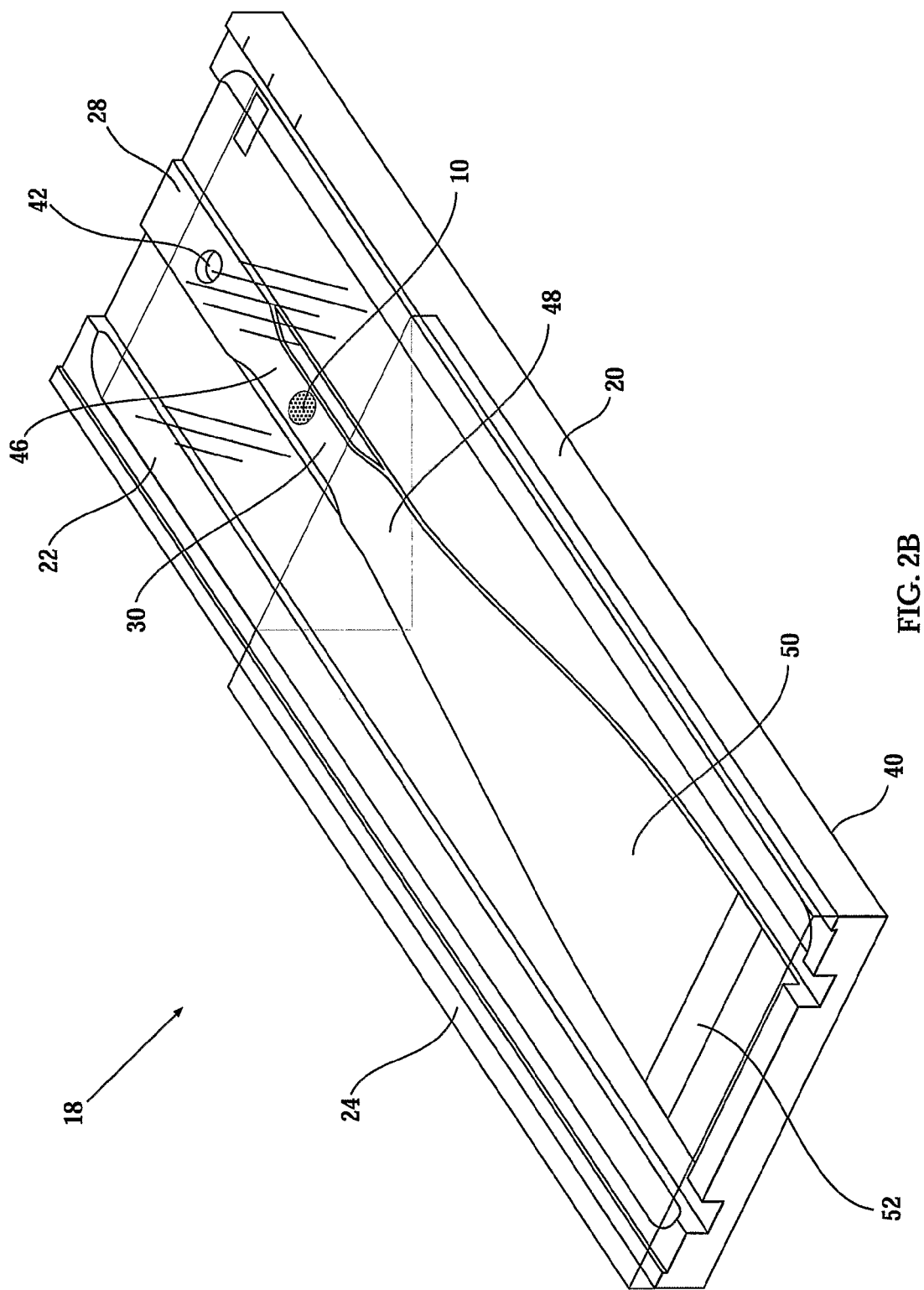

The present invention is of a method of studying floating living cells by confining the cells in picowells. The present invention is also of picowell-bearing devices for the study of cells that are less dense than the medium in which the cells are found, generally including at least one downward facing picowell on a bottom surface of a top wall of a chamber of the picowell-bearing device.

The long duration (days) study of cells using picowell-bearing devices is often desired. Such long duration study requires replenishment, preferably continuous replenishment, of medium to avoid that the changes in the medium (e.g., gas, nutrient, waste matter content) effect the experiment. Prior art devices provided with capillary channels for inlet and outlet of liquids have the disadvantages of limited total liquid that can be added and limited flow rates making performance of long duration studies difficult. Prior art devices having a picowell-containing chamber with a moveable wall allow introduction of cells directly into the chamber enabling the use of extremely small quantities of cells and uniform distribution by sedimentation. However, in such prior art devices, liquid introduced into the chamber often leaks through the moveable wall/chamber joints. In such prior art devices, if the liquid pressure applied by a flow generator (such as a pump) is too high or if capillary forces are sufficient, the moveable wall may disengage from the chamber. As both joint leakage and moveable wall disengagement can occur at any time during an experiment, the maximal duration of an experiment is limited.

On the other hand, prior art devices having picowell-containing chambers with permanently secured walls do not allow introduction of cells directly into the chamber, a fact that makes experiments more complex and difficult to perform.

Thus, an aspect of the present invention is also of picowell-bearing devices with at least one moveable wall and a force applicator configured to apply a substantially uniformly distributed force around the periphery of the moveable wall to retain the moveable wall secured to and sealing the chamber the chamber. Embodiments of such devices of the present invention allow introduction of a continuous flow of liquids into and out of the chamber without leaks at the joints of the moveable wall simplifying the performance of long duration studies.

The principles and uses of the teachings of the present invention may be better understood with reference to the accompanying description, figures and examples. In the figures, like reference numerals refer to like parts throughout.

Before explaining at least one embodiment of the invention in detail, it is to be understood that the invention is not limited in its application to the details set forth herein. The invention can be implemented with other embodiments and can be practiced or carried out in various ways. It is also understood that the phraseology and terminology employed herein is for descriptive purpose and should not be regarded as limiting.

Generally, the nomenclature used herein and the laboratory procedures utilized in the present invention include techniques from the fields of biology, chemistry, engineering, material sciences and physics. Such techniques are thoroughly explained in the literature.

Unless otherwise defined, all technical and scientific terms used herein have the same meaning as commonly understood by one of ordinary skill in the art to which the invention belongs. In addition, the descriptions, materials, methods, and examples are illustrative only and not intended to be limiting. Methods and materials similar or equivalent to those described herein can be used in the practice or testing of the present invention.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

As used herein, "a" or "an" mean "at least one" or "one or more". The use of the phrase "one or more" herein does not alter this intended meaning of "a" or "an".

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Implementation of the methods of the present invention involves performing or completing selected tasks or steps manually, automatically, or a combination thereof.

Herein, the term "active entity" is understood to include chemical, biological or pharmaceutical entities including any natural or synthetic chemical or biological substance that influences a cell with which the entity is in contact. Typical active entities include but are not limited to active pharmaceutical ingredients, antibodies, antigens, biological materials, chemical materials, chromatogenic compounds, drugs, enzymes, fluorescent probes, immunogenes, indicators, ligands, nucleic acids, nutrients, peptides, physiological media, proteins, receptors, selective toxins and toxins.

Herein, by "indicator" is meant any active entity that upon interaction with some stimulus produces an observable effect. In the context of the present invention, by stimulus is meant, for example, a specific compound, (such as a molecule) released by a cell and by observable effect is meant, for example, a visible effect or a signal, for example a change in color or emission of light.

Herein, by "picowell array" is meant a group of two or more picowells, preferably a plurality of picowells, preferably a plurality of picowells arranged in an orderly fashion. Typical arrangements include hexagonal arrays (picowells arrayed in staggered rows so that each picowell has six equidistant neighboring picowells such as depicted in FIG. 1) or rectangular arrays (picowells arrayed in rows so that each picowell has four equidistant neighboring picowells in a cross shape).

Some embodiments of the present invention include components that are transparent or are made of a transparent material. By "transparent" is meant that the component or material is substantially transparent to at least one wavelength of light (preferably a range of wavelengths) in at least part of the visible light spectrum, the ultraviolet light spectrum and/or of infrared radiation, preferably the visible light spectrum.

It is important to note that some aspects of embodiments of the present invention are related to embodiments of picowell bearing devices known in the art, especially picowell-bearing devices described by the inventor in PCT patent applications IL2001/00992 published as WO2003/035824 ("Interactive transparent individual cells biochip processor"), IL2004/000571 published as WO2004/113492 ("Improved materials for constructing cell-chips, cell-chip covers, cell-chip coats, processed cell-chips and uses thereof"), IL2004/000194 published as WO2004/077009 ("A method and device for manipulating individual small objects"), IL2004/000661 published as WO2005/007796 ("Improved multiwell plate"), and unpublished IL2005/000801 ("Device for the study of cells") which are all included by reference as if fully set forth herein.

According to a method of the present invention, living cells floating in an aqueous medium are confined in picowells, preferably in a picowell array, located on a bottom surface of a top wall of a chamber. Once confined, the living cells are observed. Preferably, the top wall of the chamber is fashioned from a substantially transparent material in the vicinity of the picowells allowing observation of the cells through the top wall. Generally, the observed cells are subjected to some stimulus, for example, introduction of an active entity into the chamber, allowing the study of the response of the cells to the active entity or stimulus. As the cells are confined in picowells, it is possible to study the behavior of each individual cell in response to the stimuli.

One device useful in implementing the method is a picowell-bearing device of the present invention.

An embodiment of a picowell-bearing device of the present invention is picowell-bearing device 18 depicted in FIGS. 2A-2E. Device 18 consists essentially of three physically separate components: a device body 20 (including an attached picowell-bearing component, carrier 44), a sliding base 22 and a base holder 24, depicted, inter alia, in FIGS. 2A (from below without sliding base 22 and base holder 24), 2B (from below, assembled), 2C (in cross section across A-A), 2D (in cross section across B-B) and 2E (from above, assembled). Suitable materials from which to fashion the components of device 18 are known in the art, are preferably transparent, and include for example, polycarbonate or glass. A picowell-array 10 is found in a hollow 26 found on plateau 28 on bottom surface 30 of device body 20, see FIG. 2A. Flanking plateau 26 are gaps 32. At each of the two sides of device body 20 are rails 34, each rail including a rail ledge 36 and a rail wall 38. Passing through plateau 26 from bottom surface 30 to upper surface 40 of device body 20 and upstream of picowell array 10 is a liquid inlet hole 42. Picowell array 10 is a feature on a picowell bearing component, carrier 44, see FIG. 2C. Carrier 44 is attached to device body 20 (for example by welding or adhesive) to the rim of hollow 26 so that picowell array 10 faces downwards. Carrier 44 is preferably made of substantially transparent material, e.g., polycarbonate or glass, allowing observation of cells therethrough.

Sliding base 22 is configured to fit device body 20 substantially parallel to bottom surface 30. Base holder 24 is configured to fit up against sliding base 22 and to engage device body 20 (e.g., by "snapping into place") so as to press sliding base 22 up against plateau 28 and rail ledges 36 of device body 20, see FIG. 2B. When held in place by base holder 24, sliding base 22 is laterally confined by rail walls 38, vertically confined between device body 20 and base holder 24 but is axially slidable relative to device body 20 in parallel to bottom surface 30. The interface between the bottom surface of plateau 28 and the top surface of sliding base 22 defines a space of capillary thickness flanked by gaps 32, see FIG. 2D. The space of capillary thickness between liquid inlet hole 42 and hollow 26 constitutes a capillary channel 46 and the space of capillary thickness between downstream of hollow 26 constitutes a waste capillary channel 48 and a waste reservoir 50. In device 18, the border between waste capillary channel 48 and waste reservoir 50 is not clearly delineated: waste capillary channel 48 is the downstream region of plateau 28 proximate to picowell array 10 while waste reservoir 50 is substantially a broader and longer section of plateau 28 downstream from waste capillary channel 48.

When sliding base 22 is held in place substantially in parallel with upper surface 28 and covering the opening of hollow 26 (FIG. 2C), a chamber is defined in which carrier 44 is substantially a top wall, sliding base 22 is a bottom wall and the wall of hollow 26 is a side wall.

When sliding base 22 is held in place substantially in parallel with upper surface 28 and covering the bottom opening of liquid inlet hole 42 (see FIG. 2B), liquid inlet hole 42 together with sliding base 22 constitutes a liquid reservoir in fluid communication with capillary channel 46. A drop of liquid placed in liquid inlet hole 42 from upper surface 40 (see FIG. 2E) contacts the top surface of sliding base 22 and is drawn by capillary action through capillary channel 46, into hollow 26, under and past picowell-array 10, out through waste capillary channel 48 and out to waste reservoir 50. Thus, in device 18, picowell-array 10 is in fluid communication with liquid inlet hole 42, that constitutes a liquid reservoir, through capillary channel 46. Picowell array 10 is in fluid communication with waste reservoir 50 through waste capillary channel 48.

A device such as device 18 is useful in the study of cells that are less dense than the medium in which the cells are found and therefore float, in accordance with the teachings of the present invention, as depicted in FIG. 3 and discussed hereinbelow.

Figure 3A:
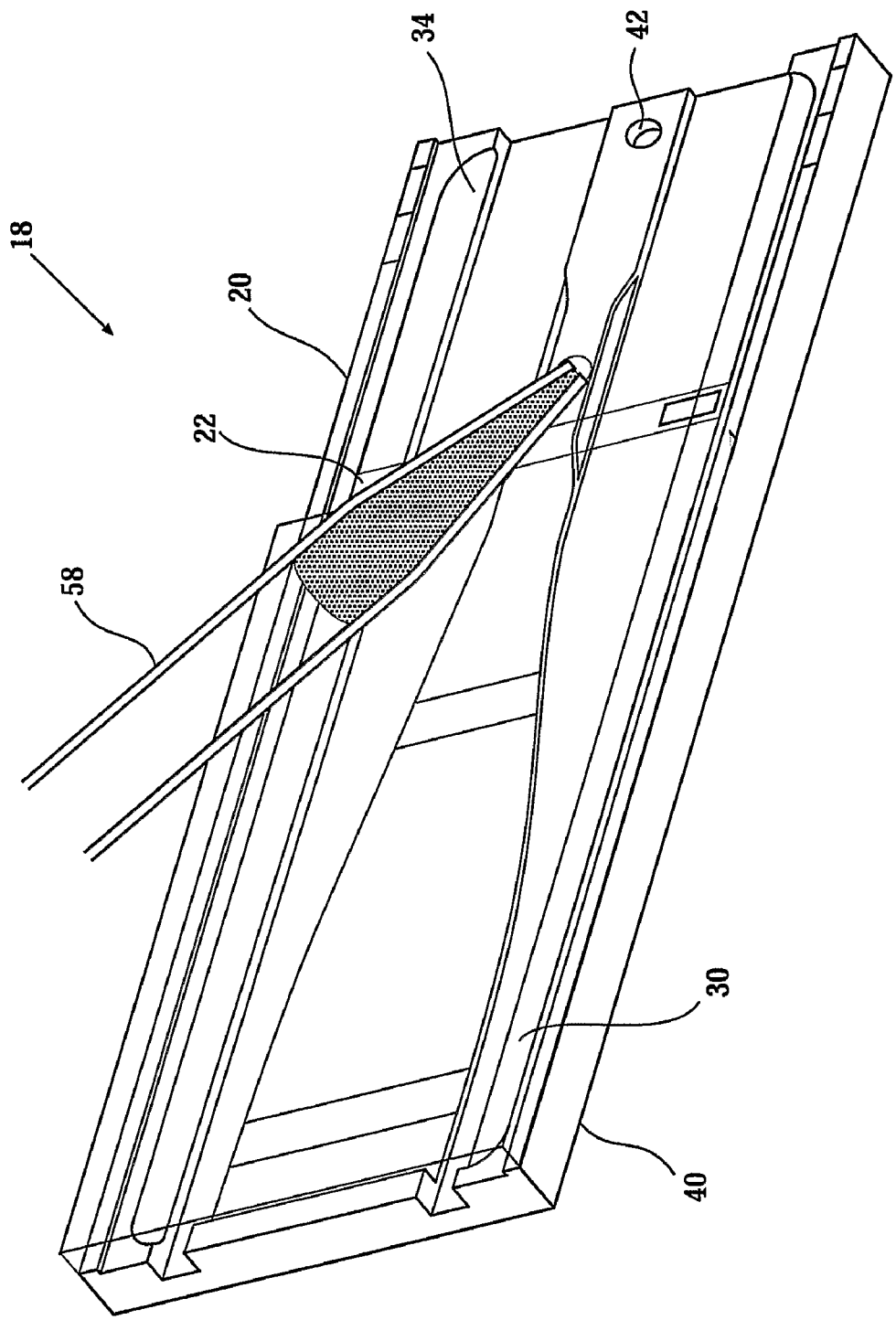
Figure 3B:
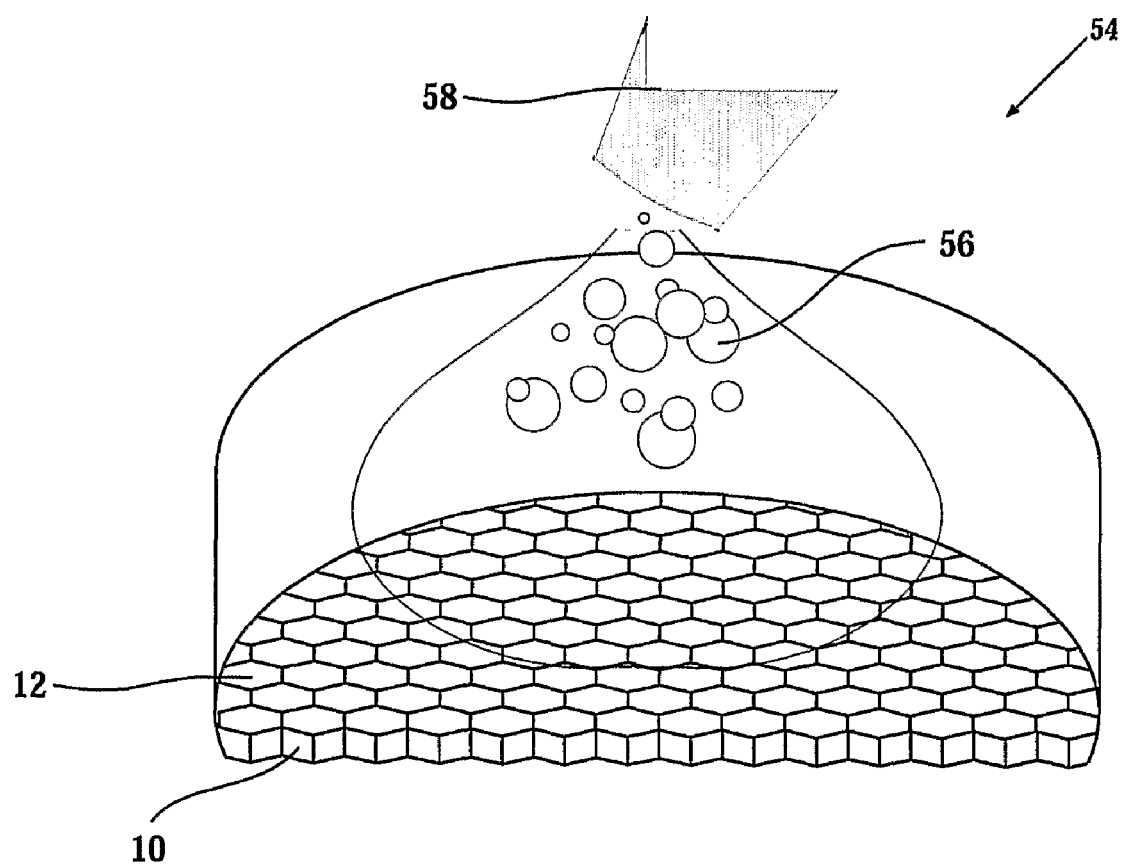
Figure 3C:
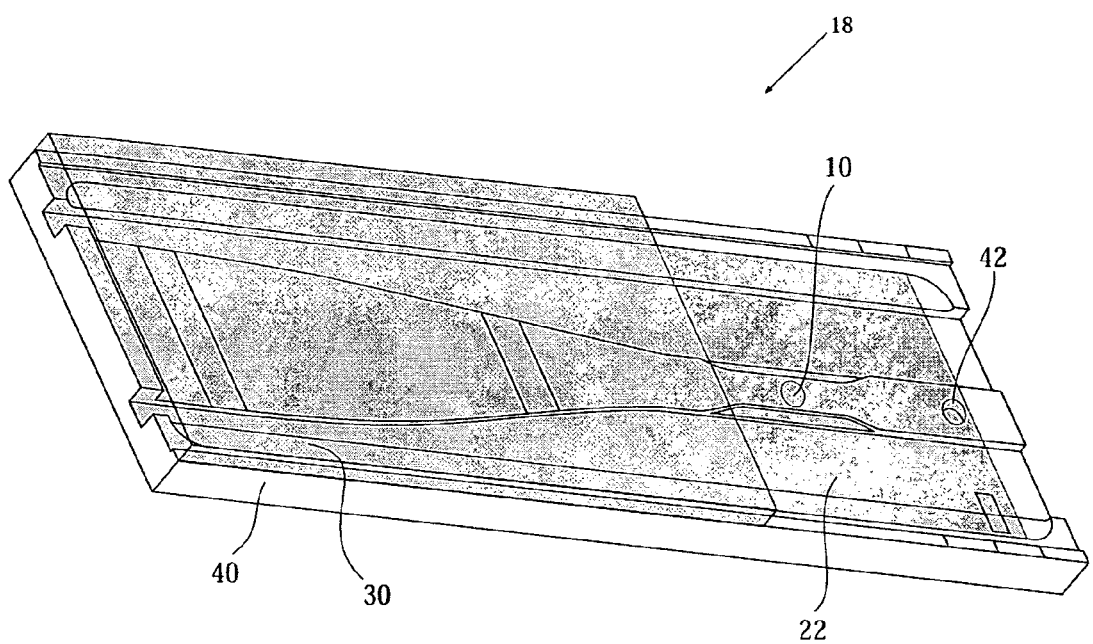
Figure 3D:
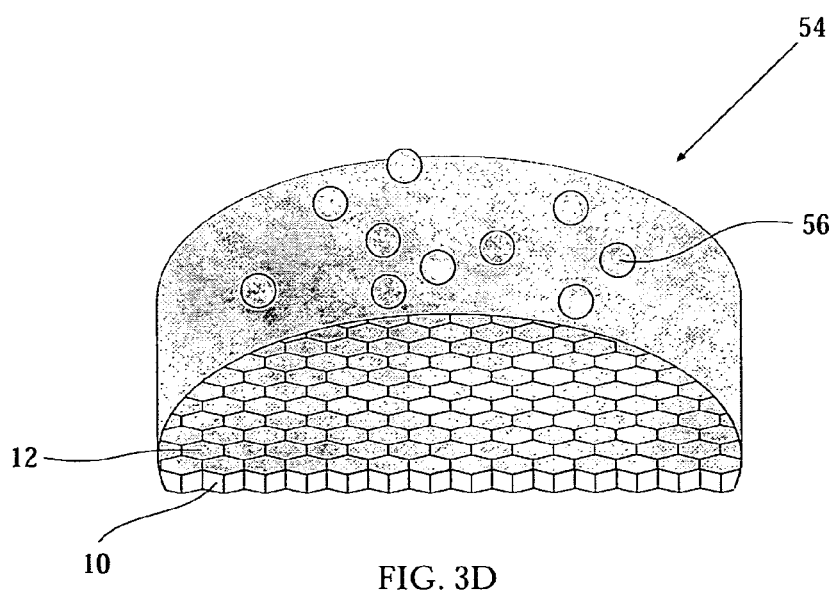

For use, sliding base 22 of picowell-bearing device 18 is positioned at a location wherein a chamber 54 defined by carrier 44, the walls of hollow 26 and sliding base 22 is accessible, that is the bottom side of chamber 54 is uncovered and constitutes an opening into chamber 54, see FIG. 3A.

In this state, device 18 is held so that upper surface 40 of device body 20 faces substantially downwards and lower surface 30 of device body 20 faces substantially upwards. A medium and cells 56 that are less dense than the medium (e.g., adipocytes) are loaded into chamber 54 for example using a pipette 58, see FIGS. 3A and 3B. Subsequently sliding base 22 is slid along rails 34 so as to cover both hollow 26 and liquid inlet hole 42, substantially closing the opening into chamber 54, see FIG. 3C. Cells 56 float upwards in chamber 54, see FIG. 3D.

Figure 3E:
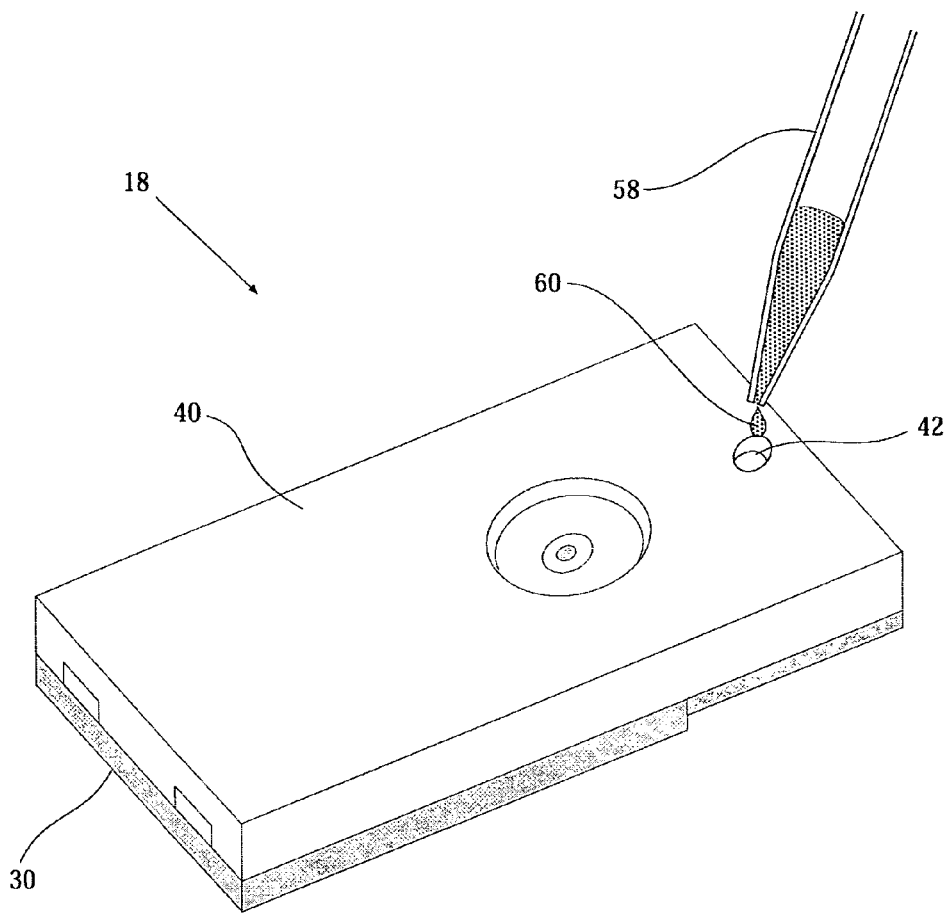
Figure 3F:
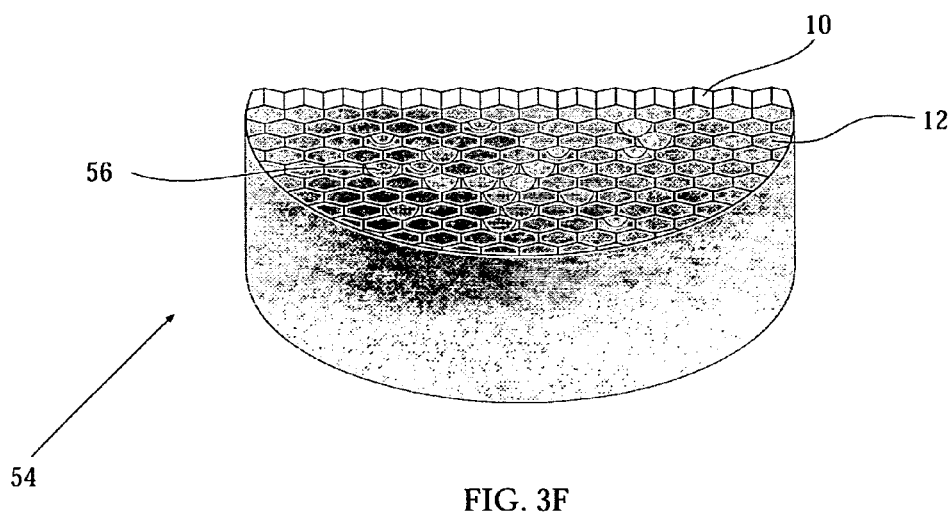

Device 18 is turned over and oriented so that upper surface 40 of device body 20 faces substantially upwards and lower surface 30 of device body 20 faces substantially downwards, as depicted in FIG. 3E. Cells 56 float upwards to enter picowells 12 of picowell array 10 made up of a hexagonal array of tightly packed knife-edged picowells 12. Each cell 56 enters an individual hexagonal picowell 36, as depicted in FIG. 3F.

Subsequently, as depicted in FIG. 3E, a pipette 58 may be used to add a cell washing solution 60 (e.g., PBS, DMEM or RPMI) to liquid inlet hole 42. From liquid inlet hole 42, cell washing solution 60 is transported by capillary action through capillary channel 46, into chamber 54 and out through waste capillary channel 48 to waste reservoir 50, thus washing living cells 56 held in picowells 12.

Subsequently, a pipette 58 is used to add a cell staining solution (e.g., fluorescein diacetate (1 micromolar), acridine orange (5 micromolar), rhodamine 123 (1 micromolar), FDA, PI, Annexin V, anti-GlycophorinA antibody labeled with allophycocanin for the study of GFP expression) to liquid inlet hole 42. Cell staining solution is transported from liquid inlet hole 42, into chamber 54 and out through waste capillary channel 48 to waste reservoir 50, thus washing living cells 56 held in picowells 12, thereby staining living cells 56 held in picowells 12. During transport of the cell staining solution, cell-staining solution 62 displaces cell-washing solution 60, as depicted in FIG. 3G.

When sufficient time has passed for cell staining, living cells 56 held in picowells 12 of picowell array 10 of picowell-bearing device 18 are examined using an observation device 64, in FIG. 3H an Olympus BX61 motorized research microscope (Olympus America Inc., Melville, N.Y., USA). As carrier 44 is substantially transparent, observation is performed from above, through carrier 44 which constitutes the top wall of chamber 54.

In embodiments, picowell-bearing device 18 of the present invention is transferred to an incubator for a period of time, before, during or after living cells 56 are examined using observation device 64.

As described above, medium and living cells 56 are introduced together into chamber 54. In embodiments of the present invention, medium and cells are not introduced together, for example living cells 56 are introduced first and subsequently medium, or first medium is introduced and subsequently living cells 56.

As described above and depicted in FIG. 3H, in embodiments of the present invention living cells 56 held in picowells 12 of picowell array 10 are observed from above. In embodiments of the present invention (not depicted), cells 56 are observed from below by an observation device positioned below picowell-bearing device 18. In such embodiments, sliding base 22 is made of substantially transparent material, e.g., polycarbonate or glass.

Described hereinabove is an experiment where cells 56 held in a picowell array 10 of a device 18 of the present invention undergo only two treatment steps: a first washing step with cell washing solution 60 and a second staining step with cell staining solution 62. Using a device of the present invention such as 18, a greater number of steps are performed if desired. In the embodiment of the present invention described hereinabove, the volume of waste reservoir 50 (and, if present, the volume of absorbent element 52 functionally-associated therewith) ultimately determines the maximal number of such steps that can be performed.

Described hereinabove is an experiment where cells 56 held in a picowell array 10 of a device 18 of the present invention undergo only two types of treatment: washing and staining. In embodiments of the present invention, cells held in picowells of a picowell array of a device of the present invention undergo other types of treatments including washing steps and/or staining steps and/or exposure to solutions containing active entities such as drug candidates, selective toxins, active pharmaceutical ingredients and the like.

In a picowell-bearing device 18 including a device body 20, the area of plateau 28 that constitutes a part of waste reservoir 50 and waste capillary channel 48 is relatively large compared to the area of plateau 28 that constitutes a part of and capillary channel 54. Thus when sliding base 22 is in place, the volume of waste reservoir 50 and waste capillary channel 48 is significantly larger than the volume of capillary channel 46. Liquid placed in liquid inlet hole 42 is therefore efficiently drawn through capillary channel 46 past hollow 26 and picowell array 10 to waste reservoir 50. When waste reservoir 50 is filled to capacity, capillary flow past picowell array 10 effectively ceases. Thus, in FIGS. 2A and 2B, device 18 is depicted having an absorbent element 52 (such as a piece of absorbent filter paper) in fluid communication with waste reservoir 50. Fluid that passes to waste capillary channel 48 is drawn into absorbent element 52.

In picowell-bearing device 10, waste capillary channel 48 is a single capillary channel that is substantially defined by the interface of sliding base 22 and plateau 28: sliding base 22 is a component of waste capillary channel 48. In embodiments of the present invention, there is more than one waste capillary channel 48. In embodiments of the present invention (not depicted), one or more waste capillary channels 48 are channels inside device body 20 and are not defined in part by a base 22.

In picowell-bearing device 18, capillary channel 46 is a single capillary channel through which a liquid reservoir (liquid inlet hole 42) and picowell array 10 are in fluid communication that is substantially defined by the interface of sliding base 22 and plateau 28: sliding base 22 is a component of capillary channel 46. In embodiments of the present invention, a device comprises more than one capillary channel 46. In embodiments of the present invention (not depicted), one or more capillary channels 46 are channels inside a device body 20 and are not defined in part by a base 22.

In picowell-bearing device 18, sliding base 22 covers the bottom of liquid inlet hole 42 and also forms capillary channel 46 that provides fluid communication between liquid inlet hole 42 and picowell array 10 contained within chamber 54. Liquid placed inside liquid inlet hole 42 is drawn by capillary action through capillary channel 46 into chamber 54 and out through waste capillary channel 48. In embodiments of the present invention, such as device 66 depicted in FIG. 2F, sliding base 22 is configured to slide outwards so as to protrude relative to the end of device body 20. The space between upper surface 68 of sliding base 22 and bottom surface 30 of plateau 28 of device body 20 defines, as described above for device 18, a capillary channel 46 providing capillary communication between upper surface 68 of protruding end 70 of sliding base 22 (constituting a liquid reservoir) and chamber 54 including picowell array 10.

In picowell-bearing device 18, sliding base 22 is configured to rest against and substantially in parallel with bottom surface 30 of device body 20, substantially contacting plateau 28 and rail ledges 36. When in place, sliding base 22 is laterally confined by rail walls 38, vertically confined by base holder 24 but is axially slidable in parallel to bottom surface 30. In embodiments of the present invention, see FIG. 2G, a sliding base 22 is configured to slidingly engage grooves 69 in rails so that when in place, sliding base 22 is laterally and vertically confined by the grooves but is axially slidable in parallel to bottom surface 30. Such an embodiment is analogous to a picowell-bearing device provided with a sliding lid fitting in grooves taught in unpublished PCT patent application IL2005/000801 of the inventor.

An additional embodiment of a device of the present invention, 72, is depicted in FIGS. 4A-4D. Device 72 comprises a device body 20 including a chamber 54 provided with a medium loading opening 74, a liquid inlet 76 and a liquid outlet 78. On bottom surface 80 of top wall 82 of chamber 54 is a picowell array 10. Device 72 further comprises a plug 84, configured to sealingly engage medium loading opening 74. Preferably, all walls of device 72 are substantially entirely of a transparent material.

Device 18 of the present invention described above is provided with sliding base 22 as a moveable wall configured to substantially define and seal chamber 54. In contrast, device 72 is provided with a removable component, plug 84, to substantially seal medium loading opening 74 subsequent to introduction of medium into chamber 54.

Device 18 of the present invention described above is provided with a picowell-array bearing carrier 44 that is fixedly attached to device body 20. In contrast picowell array 10 of device 72 is an integral feature of bottom surface 80 of top wall 82 of chamber 54.

For use, a medium and living cells 56 that are less dense than the medium are introduced (together or separately) into chamber 54 through medium loading opening 74, FIG. 4A. Opening 74 is sealed using plug 84, FIG. 4B. Generally, a certain amount of air remains trapped between the inner surface of plug 84 and the surface of medium added. Device 72 is oriented by tilting at an angle so that picowell array 10 slopes upwards from medium loading opening 74 towards an excess gas storage section 86 of chamber 54, FIG. 4C. Trapped air rolls upwards past picowell array 10 to be trapped in excess gas storage section 86. Cells 56 float slowly upwards along picowell array 10. When a cell 56 encounters an empty picowell, the cell enters the picowell and is held therein. When a cell 56 encounters an occupied picowell, the cell floats upwards further. In such away, dense packing of picowell array 10 with cells 56 is achieved. When sufficient cells 56 introduced into device 72 are trapped in picowell array 10, device 72 is oriented so that picowell array 10 is substantially facing downwards, FIG. 4D. Cells 56 held in picowell array 10 are then observed as described above. Generally, for the performance of experiments and the study of cells, a flow generator, such as a pump or syringe, is attached to liquid inlet 76.

Figure 5A:
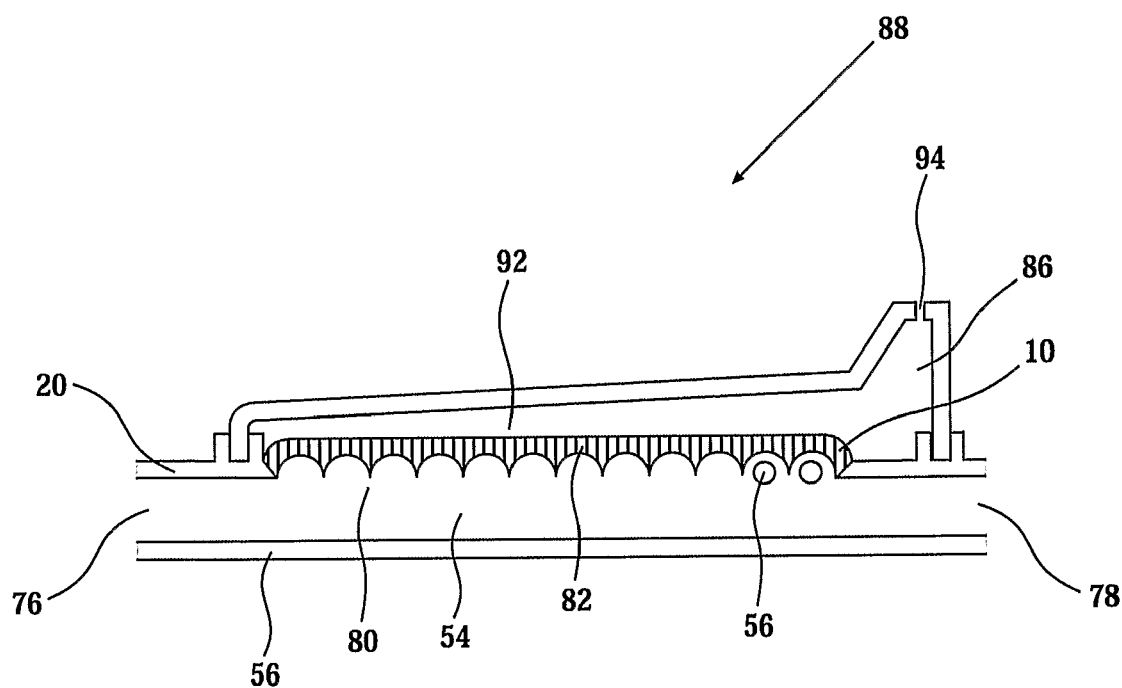
FIGS. 5A and 5B depict embodiments of devices of the present invention including a porous picowell array on a bottom surface of a top wall of a first chamber and a second chamber above the first chamber.
Figure 5B:
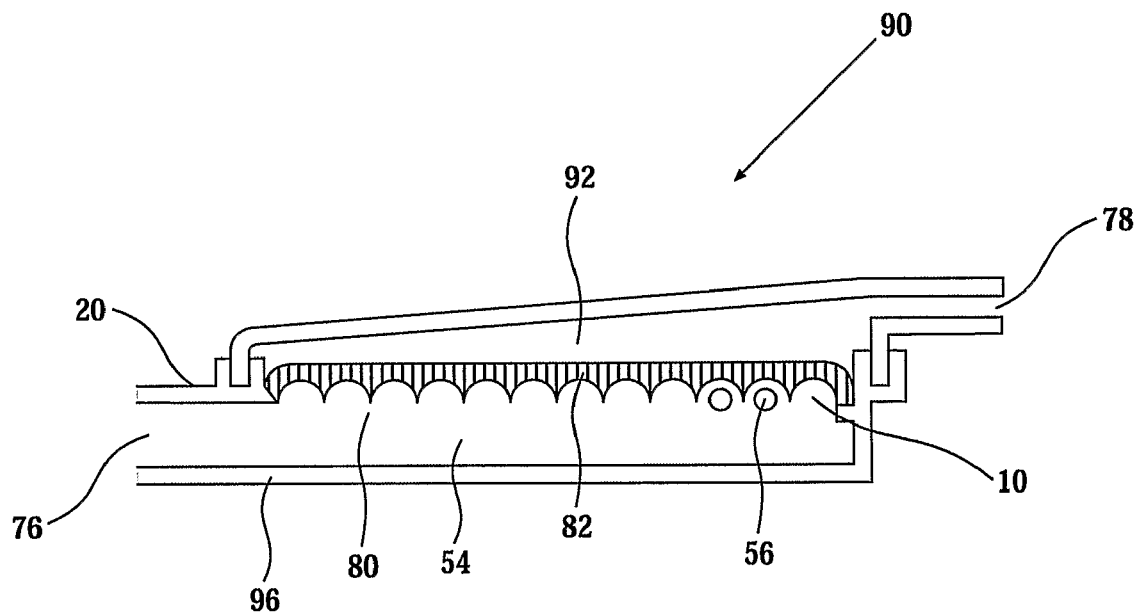

Two additional embodiments of a device of the present invention, 88 and 90, are depicted in cross-section in FIGS. 5A and 5B, respectively. Amongst other features, devices 88 and 90 are provided with a porous picowell array 10 configured to allow the escape of trapped gases. Devices 88 and 90 comprise a chamber 54 provided with a liquid inlet 76 and a liquid outlet 78. On bottom surface 80 of top wall 82 of chamber 54 is a picowell array 10. In both devices 88 and 90, top wall 82 separates chamber 54 from upper chamber 92. Top wall 82 and consequently picowell array 10 are porous, allowing the flow of fluids (both gases and liquids) between chamber 54 and upper chamber 92 therethrough. Typically the pores through top wall 82 are relatively large, e.g., up to about 15 microns as floating cells such as adipocytes are generally of between 25 to 75 microns in diameter.

In both device 88 and device 90, the picowells of picowell array 10 are porous so as to allow fluid flow therethrough, so that there is fluid communication between chamber 54 and upper chamber 92, allowing air caught in picowells 12 to pass into upper chamber 92. In device 88 both liquid inlet 76 and liquid outlet 78 are in direct fluid communication with chamber 54. In device 88, upper chamber 92 has an upwardly sloping top wall that terminates in excess gas storage section 86 provided with a vent 94 as a fluid outlet for trapped gases.

In device 90, liquid inlet 76 is in direct fluid communication with chamber 54 but liquid outlet 78 is in fluid communication with chamber 54 through top wall 82 and upper chamber 92.

For the performance of experiments and the study of cells, a flow generator such as a pump or syringe is attached to liquid inlet 76 of a device 88 or 90 as taught in embodiments of PCT patent application IL2001/00992 published as WO2003/035824 of the inventor. The device is oriented so that bottom surface 80 of top wall 82 of chamber 54 faces downwards. Medium and living cells 56 that are less dense than the medium are introduced (together or separately) into chamber 54 through liquid inlet 76. Cells 56 entering chamber 54 through liquid inlet 76 float upwards in the medium to be held in picowells of picowell array 10. Air in chamber 54 may be evacuated in any of a number of ways including being forced out through liquid outlet 78 and being passed through pores in top wall 82 into upper chamber 92.

In device 88, air in upper chamber 92 follows the slope of the upper wall of upper chamber 92 to excess gas storage section 86 and out through vent 94. As a result there are substantially no air bubbles trapped in picowells 12 that may potentially interfere with observation of cells 56 held therein. Cells 56 held in picowell array 10 may then observed and/or manipulated as described above.

In device 90, air and medium are forced into upper chamber 92 through pores of top wall 82, follow the slope of the upper wall of upper chamber 92 and may be removed from upper chamber 92 through liquid outlet 78. As a result there are no air bubbles trapped in picowells that potentially interfere with observation of cells 56 held therein. Cells 56 held in picowell array 10 are then observed as described above.

In a preferred embodiment, device 88 and device 90 both include at least three components. A first component is substantially top wall 82 which constitutes a carrier, preferably of transparent material such as polycarbonate or glass, having picowell array 10 as a feature molded on bottom surface 80. An exceptionally suitable material from which to fashion porous top wall 82 is porous polytetrafluoroethylene available from Porex Corporation (Fairburn, Ga., USA) especially a polytetrafluoroethylene having an index of refraction close to that of water. A second component is a device body 20, preferably of transparent material such as polycarbonate or glass, including a base 96, an inlet 76, side walls (not depicted), in the case of device 88 outlet 78, and having an opening with a rim configured to receive porous top wall 82. Preferably, top wall 82 and device body 20 are attached with the use of adhesive (e.g., light-cured adhesive) or welding. A third component, preferably of a transparent material such as glass or polycarbonate is substantially the walls that define upper chamber 92, and in the case of device 90 also outlet 78, that is configured to attach, for example by "snap-fit", to the first and second components.

Figure 6:
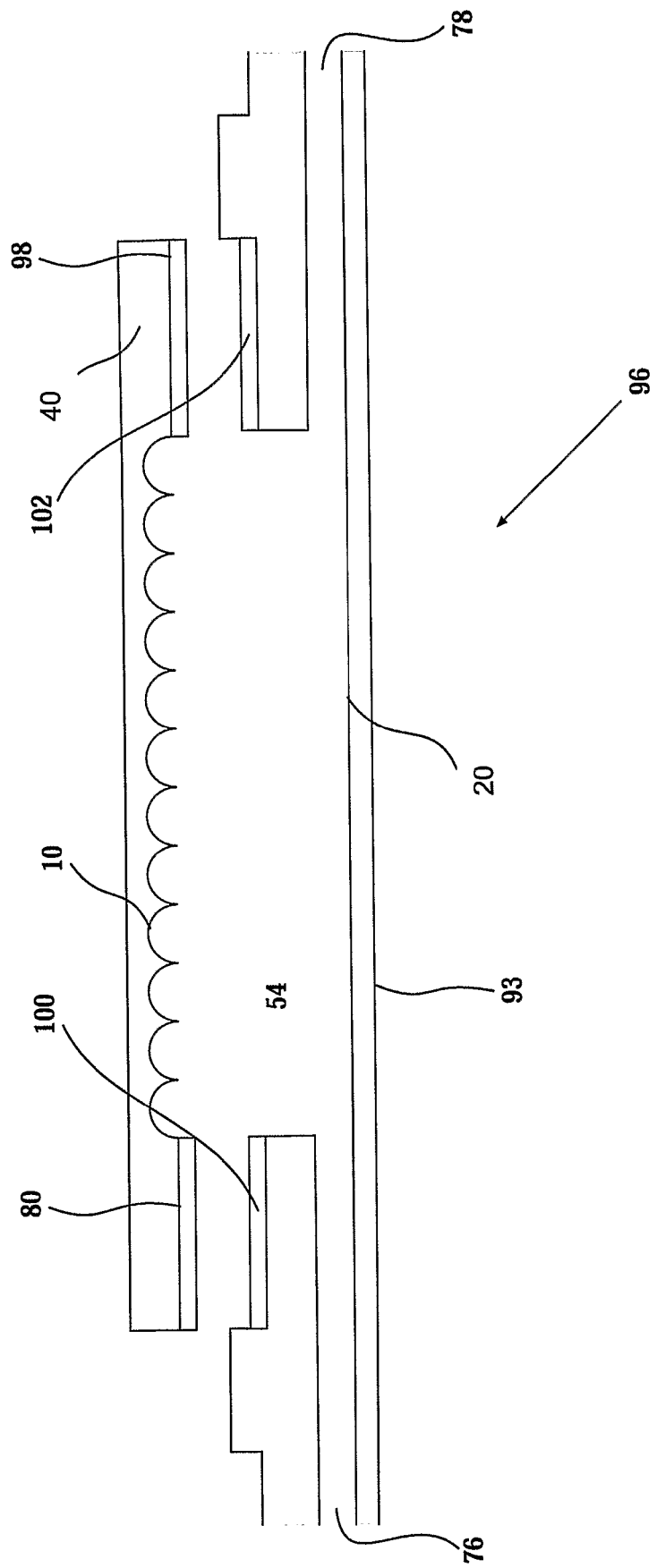
FIG. 6 depicts an embodiment of a device of the present invention including a picowell array on a bottom surface of a removeable top wall of a chamber.

An additional embodiment of a device of the present invention, 96, is depicted in an exploded view of a side cross-section in FIG. 6. In FIG. 6 are depicted two individual components of device 96, a carrier 44 and a device body 20.

Carrier 44 is made of transparent material, is substantially planar and has a bottom surface 80. To bottom surface 80 is attached (for example using adhesive) a ring-shaped upper retaining magnet 98 around the periphery of carrier 20 surrounding a picowell array 10 which is a feature on bottom surface 80 of carrier 20.

Device body 20, preferably of transparent material, is seen in cross section in FIG. 6, substantially includes a base 96 and side walls (not depicted) that define a chamber 54 with a top opening. In fluid communication with chamber 54 are an inlet 76 and an outlet 78. Around the periphery of rim 100 of the top opening of chamber 54 is attached (for example using adhesive) a ring-shaped lower retaining magnet 102 having similar dimensions but a polarity opposite that of upper retaining magnet 98.

Similarly to devices 18, 66, 72, 88 and 90, device 96 is provided with a picowell array 10 on a bottom surface 80 of a carrier 44 and bottom surface 80 constitutes an upper wall of chamber 54. Similarly to devices 72, 88 and 90, device 96 is provided with non-capillary liquid inlet 76 and liquid outlet 78 in fluid communication with chamber 54 and for use generally requires attachment of a flow generator to liquid inlet 76. Similarly to devices 18 and 66, chamber 54 of device 96 includes a moveable wall. However, unlike devices 18 and 66 where the moveable wall is a sliding base component, in device 96 the moveable wall is removable carrier 44 that constitutes the upper wall of chamber 54.

Magnets 98 and 102 are configured to secure carrier 44 to device body 20 so as to substantially seal chamber 54. Magnets 98 and 102 together constitute a force applicator that, when contacted, together apply a substantially uniformly distributed force around the periphery of carrier 44 in a perpendicular direction so as to retain carrier 44 secured to device body 20 and thus to chamber 54.

For the performance of experiments and the study of cells using a device 96, a flow generator such as a pump or syringe is attached to liquid inlet 76 of a device 96 as taught in embodiments of PCT patent application IL2001/00992 published as WO2003/035824 of the inventor. Carrier 44 is removed, allowing access to chamber 54 through the top opening. Medium and living cells 56 that are less dense than the medium are introduced (together or separately) into chamber 54 through the top opening. Carrier 44 is placed in proximity of the top opening so that magnets 98 and 102 are mutually attracted, holding carrier 44 firmly in place. Device 96 is oriented so that bottom surface 80 of carrier 44 faces downwards. Cells 56 in chamber 54 floating in the medium in chamber 54 enter picowells of picowell array 10 and are held therein.

Cells 56 held in picowell array 10 are then observed as described above and in the art, including during and subsequent to introduction of active entities through inlet 76. As noted above, device 96 is configured to allow simple loading of cells 56 into picowells and to allow performance of long-duration experiments free of leaks even with relatively high pressure and continuous inflow of liquids through inlet 76 due to the use of a force applicator that applies a substantially uniformly distributed force around the periphery of carrier 44 to retain carrier 44 secured to device body 20 and sealing chamber 54.

Figure 7A:
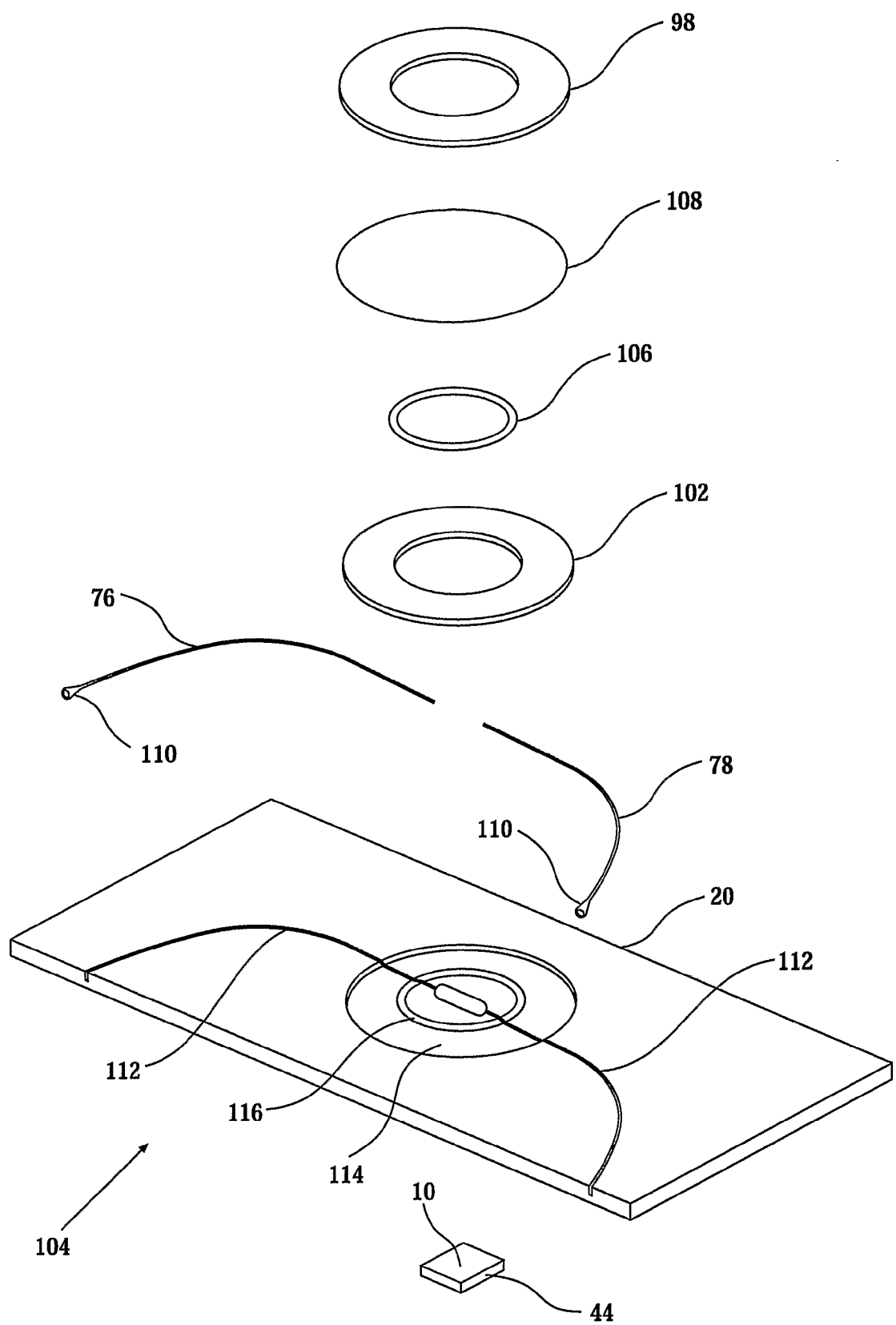
FIGS. 7A-7D depict an embodiment of a device of the present invention including a chamber with a removeable top wall and a picowell array on the top surface of the bottom wall of the chamber.
Figure 7B:
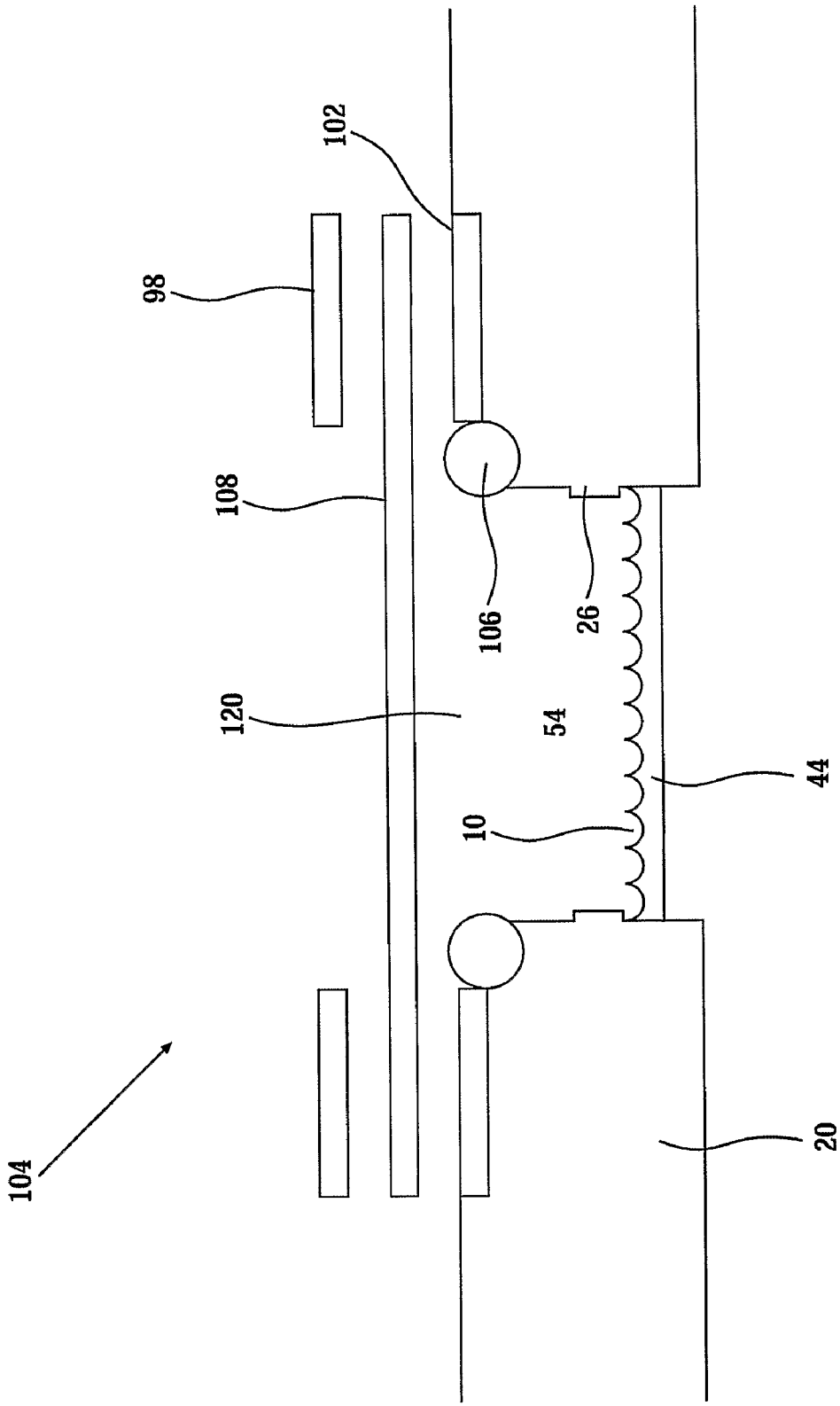
Figure 7C:
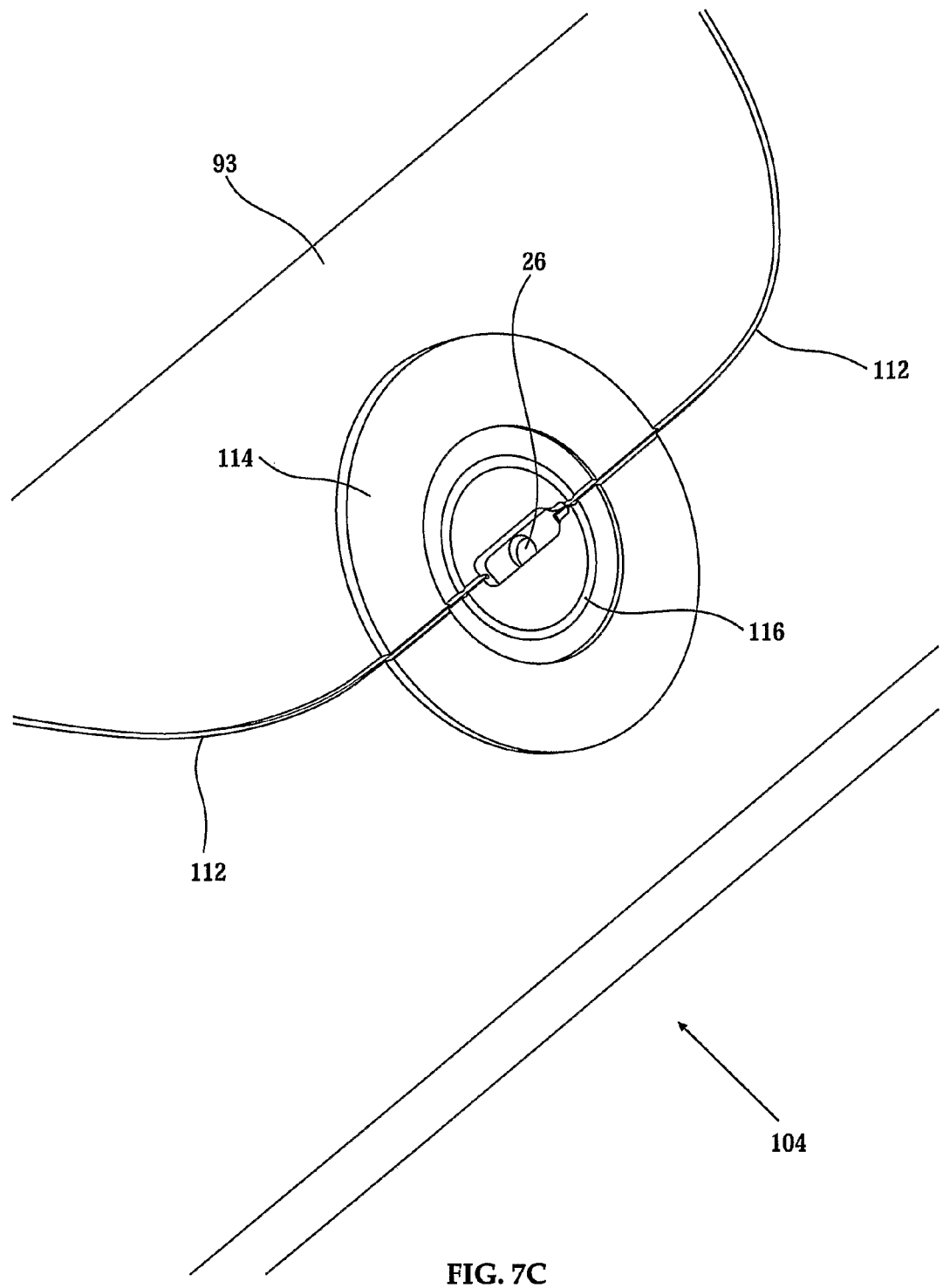
Figure 7D:
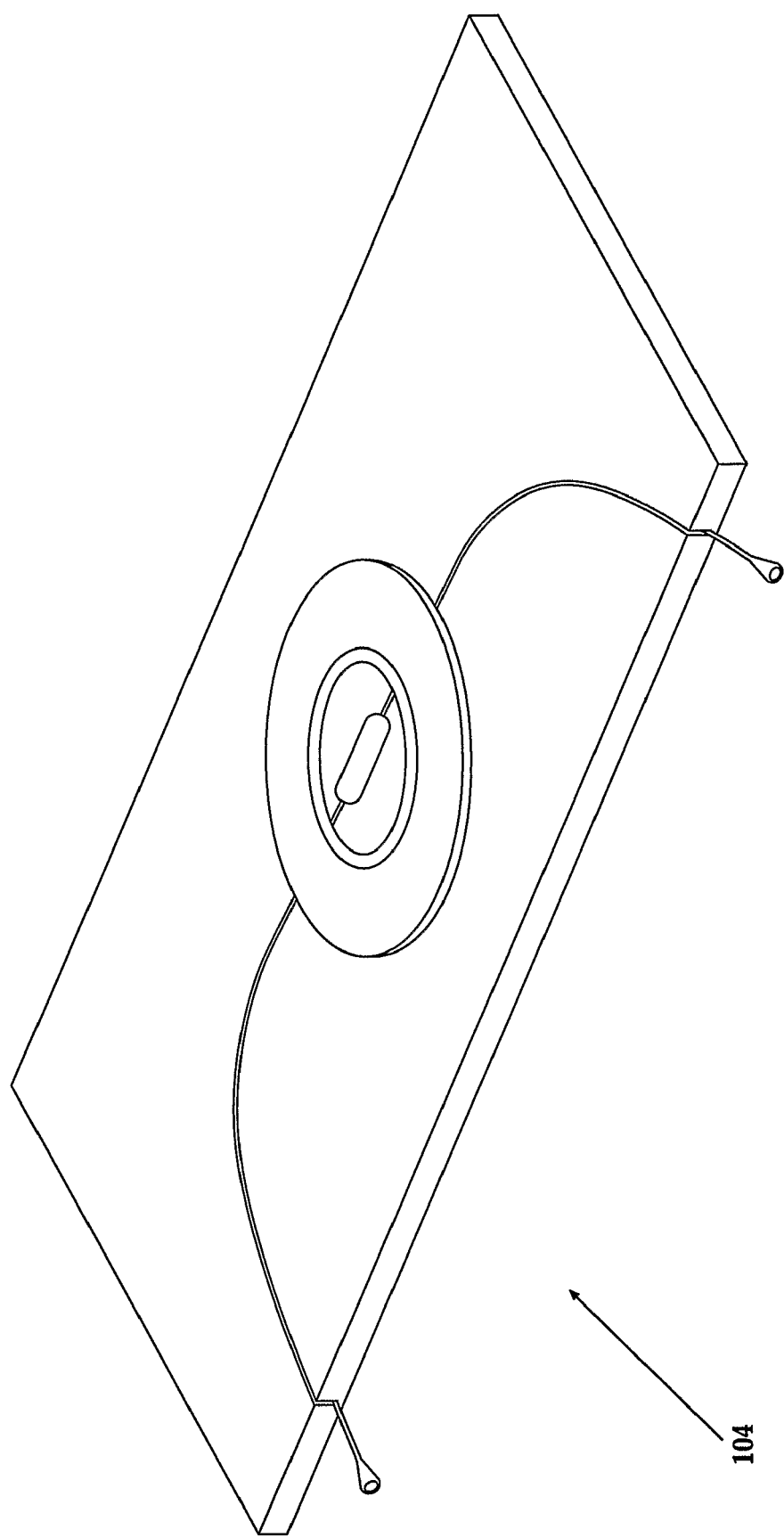

An additional embodiment of a device of the present invention, 104, is depicted in an exploded view in perspective in FIG. 7A (to scale), an exploded view of a side cross-section in FIG. 7B (not to scale), a close-up showing details of device body 20 from the top in FIG. 7C (to scale) and an assembled view in perspective in FIG. 7D (to scale). Unlike previously discussed devices 18, 66, 72, 88, 90 and 96, device 104 may not be exclusively configured for the study of floating cells in accordance with the teachings of the present invention.

Device 104 essentially consists of eight components: a carrier 44 as a picowell bearing component, a device body 20, a liquid inlet 76, a liquid outlet 78, a lower retaining magnet 102, a gasket 106, a chamber cover 108 and an upper retaining magnet 98.

Figure 2C:
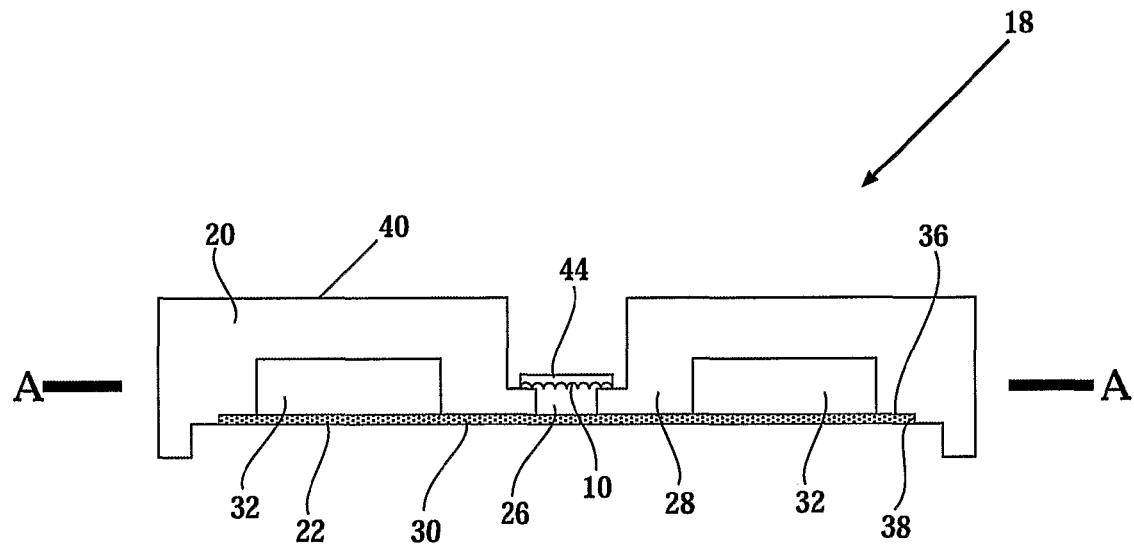
Figure 2D:
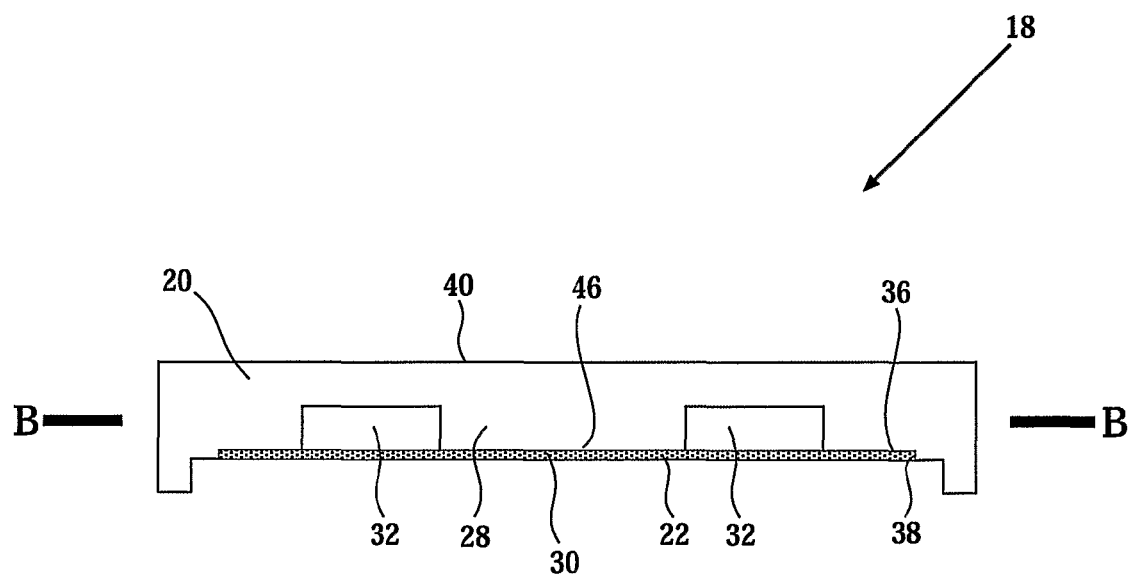
Figure 2E:
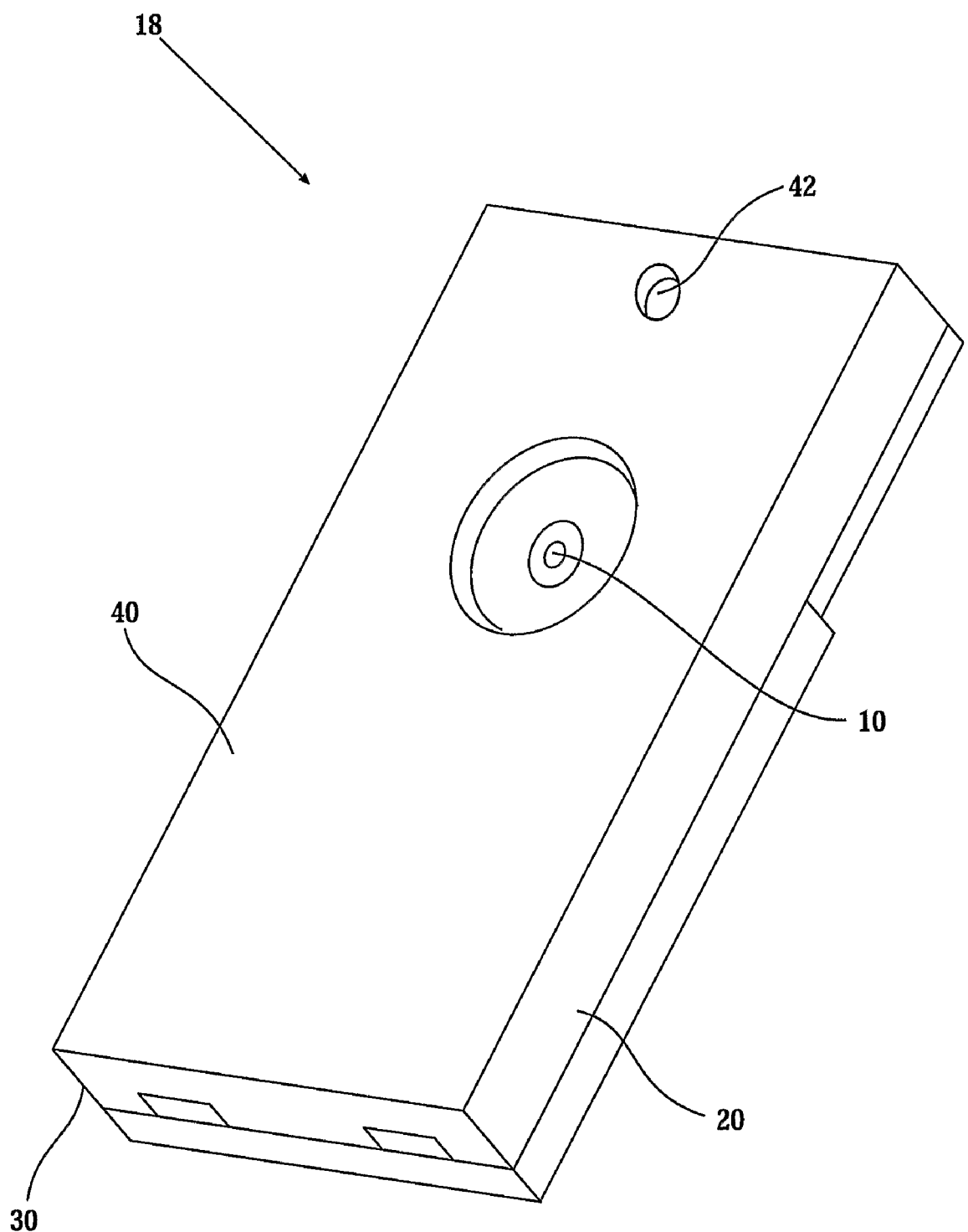
Figure 2F:
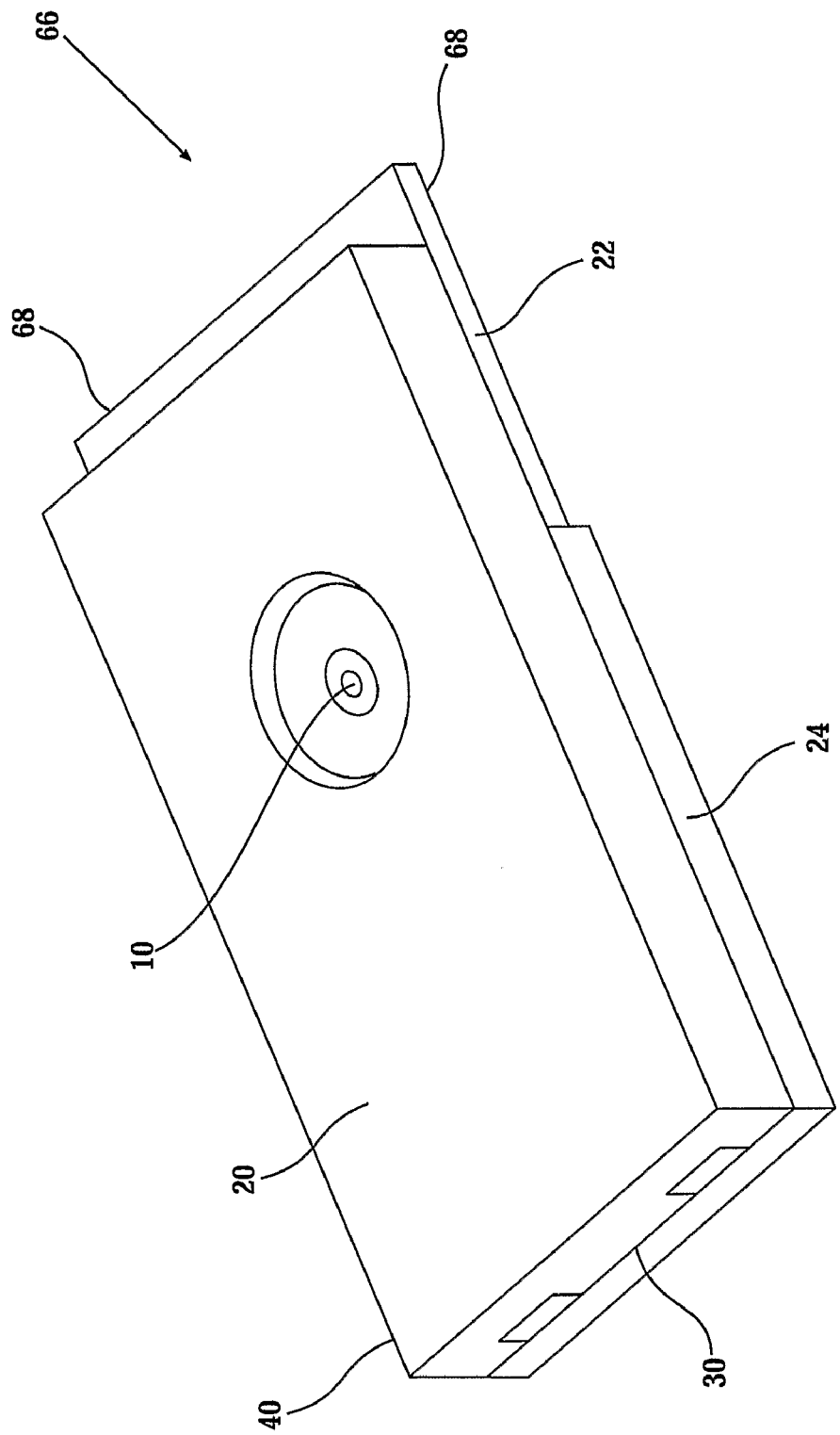
FIG. 2F depicts an embodiment of a device of the present invention including a picowell array on a bottom surface of an upper wall of a chamber and capillary channels in fluid communication with the picowell array.
Figure 2G:
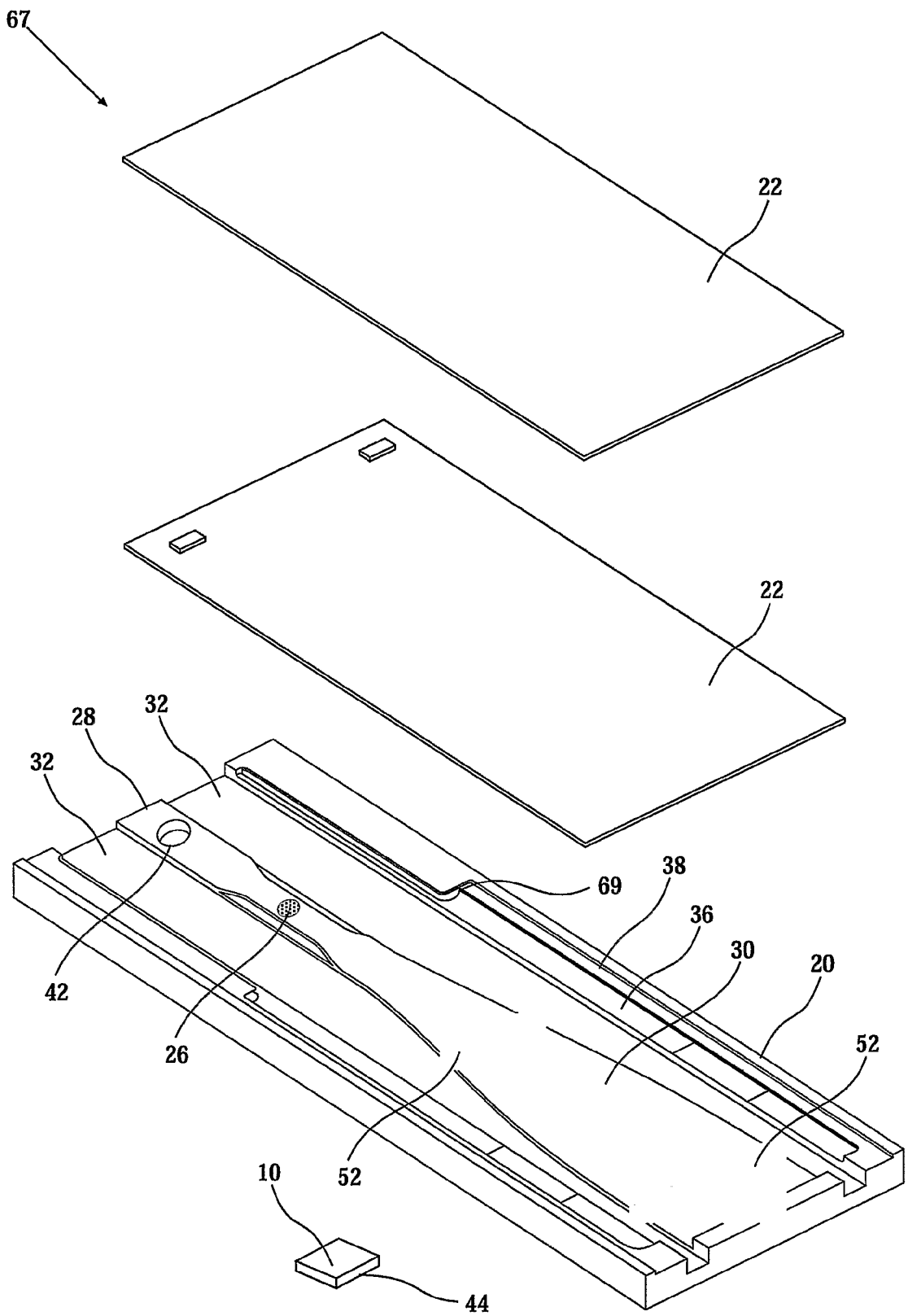
FIG. 2G depicts an embodiment of a device of the present invention including a picowell array on a bottom surface of an upper wall of a chamber and capillary channels in fluid communication with the picowell array.

Carrier 44, is a substantially planar component including a picowell array 10 as a feature on an upper surface, similar to carrier 44 of device 18 depicted in FIG. 2C. Carrier 44 is preferably made of substantially transparent material, e.g., polycarbonate or glass, allowing observation of cells therethrough.

Carrier 44 is attached to the periphery of the bottom rim of a hollow 26 (for example by welding or adhesive) to device body 20 so that picowell array 10 faces upwards defining a chamber 54 with an opening 120 at the top, the walls of hollow 26 as sides and carrier 44 as a bottom surface. Preferably, device body 20 is fashioned from a transparent material.

Liquid inlet 76 and liquid outlet 78 are essentially tubes that may be fashioned from for example of PEEK polymer attached, for example using adhesive, inside grooves 112 located on the top surface of device body 20. A first end of inlet 76 and outlet 78 emerges into chamber 54 while a second end is provided with connector 110 allowing simple, quick and leak-free attachment to a liquid flow generator.

Lower retaining magnet 102 is substantially a flat thin ring attached, for example using adhesive, to device body 20 in a broad circular groove 114 located on the top surface of device body 20 around the periphery of hollow 26.

Gasket 106 is configured to rest in a circular groove 116 located on the top surface of device body 20 surrounding hollow 26 and surrounded by broad circular groove 114.

Chamber cover 108 is substantially planar disk made of substantially transparent material. Chamber cover 108 constitutes a removable top wall of chamber 54.

Upper retaining magnet 98 is substantially a flat thin ring of substantially the same size and shape of lower retaining magnet 102.

Device 104 is substantially similar to device 96 depicted in FIG. 6. For example, both device 96 and device 104 are provided with a carrier 44 as a picowell-bearing component. However, whereas in device 96 carrier 44 constitutes a moveable top wall of a chamber 54 for the study of floating cells, in device 104 carrier 44 constitutes a fixed bottom wall of a chamber 54 for the study of cells that settle in a medium.

Further, in both device 96 and device 104, magnets 98 and 102 are configured to secure a respective removable top wall of chamber 54 (carrier 20 in device 96 and chamber cover 108 in device 104). In both devices magnets 98 and 102 together constitute a force applicator that, when contacted, together apply a substantially uniformly distributed force around the periphery of the respective moveable wall in a direction to retain the moveable wall secured to chamber 54. However, whereas in device 96 upper retaining magnet 98 is attached to the bottom surface of carrier 44 (which constitutes a removable top wall of chamber 54) and makes direct contact with lower retaining magnet 102, in device 104 chamber cover 108 (which constitutes a removable top wall of chamber 54) is sandwiched between upper retaining magnet 98 and lower retaining magnet 102.

Performance of experiments using device 104 is substantially analogous to performance of experiments using device 96. A flow generator such as a pump or syringe is attached to connector 110 of liquid inlet 76 of device 104 as taught in embodiments of PCT patent application IL2001/00992 published as WO2003/035824 of the inventor. Upper retaining magnet 98 and chamber cover 108 are removed, allowing access to chamber 54 through top opening 120. Medium and living cells 56 that are denser than the medium are introduced (together or separately) into chamber 54 through top opening 120. Cells 56 settle by sedimentation into picowells of picowell array 10. Gasket 106 is placed in groove 116. Chamber cover 108 is placed on top of gasket 106 and lower retaining magnet 102. Upper retaining magnet 98 is placed on top of chamber cover 108 so that magnet 98 and 102 are mutually attracted, holding chamber cover 108 firmly in place. The force applied on chamber cover 108 by magnets 98 and 102 compresses gasket 106 ensuring a tight seal.

Cells 56 held in picowell array 10 may then be observed and/or manipulated as described above and in the art, including during and subsequent to introduction of active entities through inlet 76. As discussed above, device 104 is configured to allow simple loading of cells 56 into picowells of picowell array 10 and to allow performance of long-duration experiments free of leaks even with relatively high pressure and continuous inflow of liquids through inlet 76 due to the use of a force applicator that applies a substantially uniformly distributed force around the periphery of chamber cover 108 to retain chamber cover 108 secured to chamber 54.

Both device 96 and device 104 use two mutually attracting magnets as components of a force applicator to retain a chamber 54 substantially sealed. In embodiments of devices of the present invention that resemble devices 96 and 104, one of the two magnets is replaced with an appropriately shaped component of ferromagnetic material.

Figure 7E:
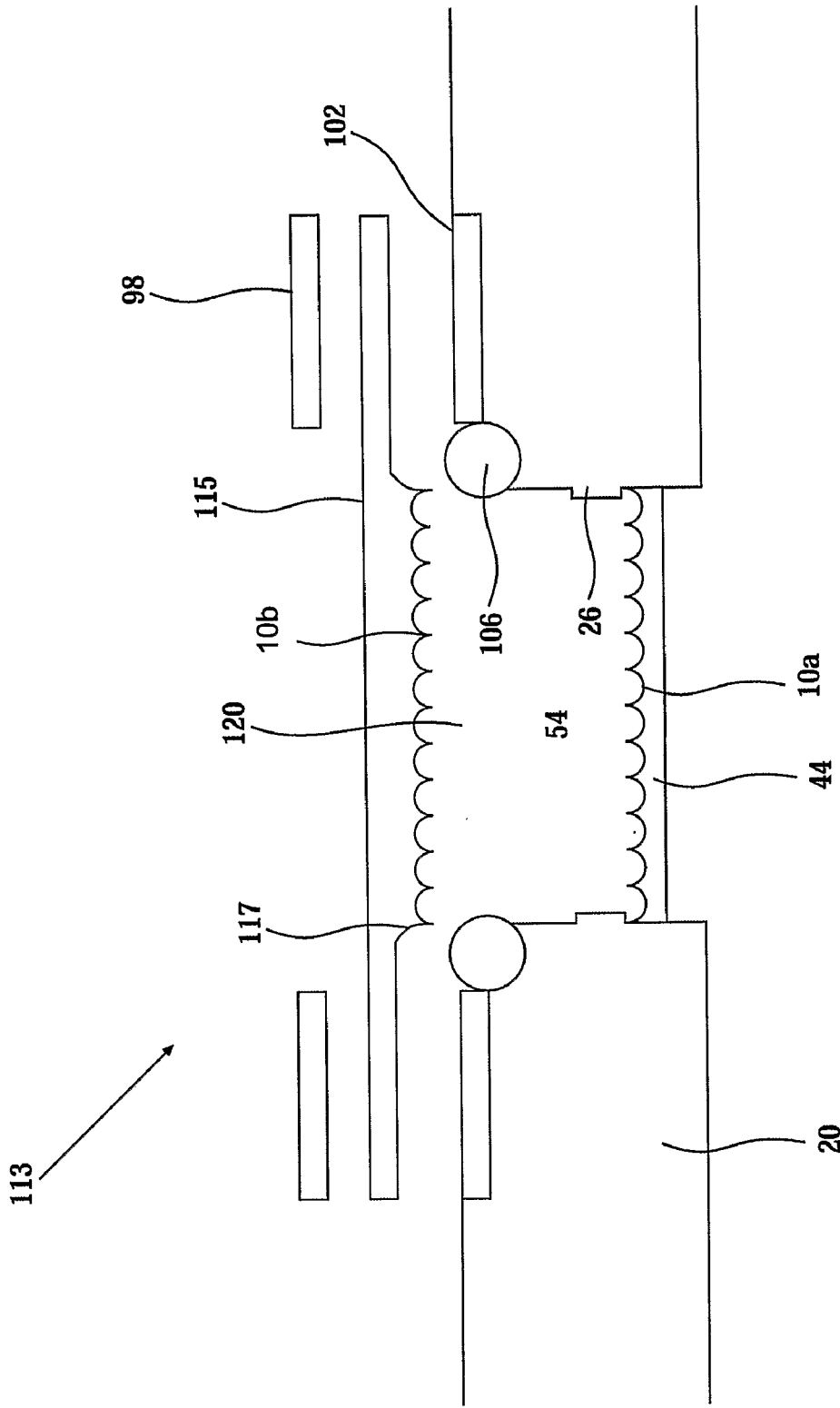
FIG. 7E depicts an embodiment of a device of the present invention having two picowell arrays in a chamber, one on the top surface of a bottom wall and one on the bottom surface of a top wall of a chamber.

An additional embodiment of a device of the present invention, 113, is depicted in side cross-section in FIG. 7E. In FIG. 7E are depicted six individual components of device 113: a carrier 44, a device body 20, a gasket 106, a lower retaining magnet 102, a picowell-bearing chamber cover 115 and an upper retaining magnet 98.

Carrier 44, is a substantially planar component including a first picowell array 10a as a feature on an upper surface, similar to carrier 44 of device 18 depicted in FIG. 2C. Carrier 44 is preferably made of substantially transparent material, e.g., polycarbonate or glass, allowing observation of cells therethrough.

Carrier 44 is attached to the periphery of the bottom rim of a hollow 26 (for example by welding or adhesive) to device body 20 so that first picowell array 10a faces upwards defining a chamber 54 with an opening 120 at the top, the walls of hollow 26 as sides and carrier 44 as a bottom surface. Preferably, device body 20 is fashioned from a transparent material. Passing through device body 20 and emerging out into chamber 54 are a liquid inlet and a liquid outlet such as depicted for device 104 in FIGS. 7A, 7B, 7C and 7D. Lower retaining magnet 102, gasket 106 and upper retaining magnet 98 are substantially identical to the equivalent components of device 104 in FIGS. 7A, 7B, 7C and 7D.

Picowell-bearing chamber cover 115 is substantially planar disk made of transparent material and like chamber cover 108 of device 104 constitutes a removable top wall of chamber 54. However, as a feature integrally formed to the bottom surface of picowell-bearing chamber cover 115 is a second picowell array 10b.

The fact that device 113 is provided with two picowell arrays 15a and 15b allows device 113 to be used for the simultaneous study of floating cells and cells that settle in a medium, as well as the interaction therebetween.

Performance of experiments using device 115 is substantially analogous to performance of experiments using device 96 and device 104. A flow generator such as a pump or syringe is attached to a liquid inlet of device 115 as taught in embodiments of PCT patent application IL2001/00992 published as WO2003/035824 of the inventor. Upper retaining magnet 98 and picowell-bearing chamber cover 115 are removed, allowing access to chamber 54 through top opening 120. Medium and living cells 56 are introduced into chamber 54 (together or separately) through top opening 120. Gasket 106 is placed in a groove 116. Picowell-bearing chamber cover 115 is placed on top of gasket 106 and lower retaining magnet 102 so that guide lips 117 contact gasket 106, thus centering picowell-bearing chamber cover 115 in chamber 54. Cells of a first type that float in the medium float upwards to be held in picowells of second picowell array 10b. Cells denser than the medium settle by sedimentation into picowells of first picowell array 10a. Upper retaining magnet 98 is placed on top of picowell-bearing chamber cover 115 so that magnets 98 and 102 are mutually attracted, holding picowell-bearing chamber cover 115 firmly in place. The force applied on picowell-bearing chamber cover 115 by magnets 98 and 102 compresses gasket 106 ensuring a tight seal.

Cells held in picowell arrays 10a and 10b are then observed as described above and in the art, including during and subsequent to introduction of active entities through the liquid inlet. As discussed above, device 104 is configured to allow simple loading of cells into picowells of picowell arrays 10a and 10b and to allow performance of long-duration experiments free of leaks even with relatively high pressure and continuous inflow of liquids through a liquid inlet due to the use of a force applicator that applies a substantially uniformly distributed force around the periphery of picowell-bearing chamber cover 115 to retain picowell-bearing chamber cover 115 secured to chamber 54.

Figure 8:
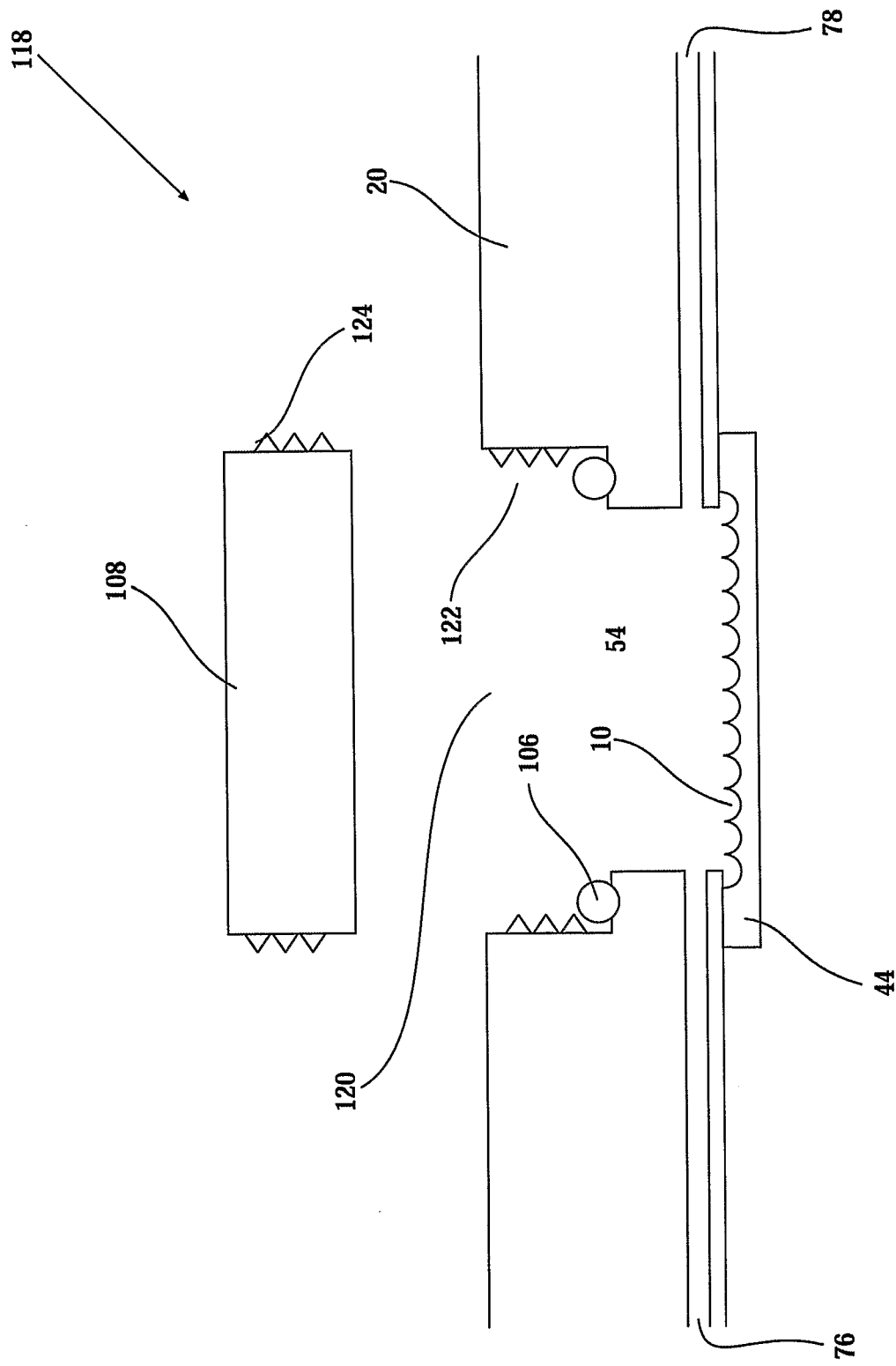
FIG. 8 depicts an embodiment of a device of the present invention including a chamber with a removeable top wall and a picowell array on the top surface of the bottom wall of the chamber.

An additional embodiment of a device of the present invention, 118, is depicted in side cross-section in FIG. 8. In FIG. 8 are depicted four individual components of device 118: a carrier 44, a device body 20, a gasket 106 and a chamber cover 108.

Carrier 44 is a substantially planar component including a picowell array 10 as a feature on an upper surface, similar to carrier 44 of device 18 depicted in FIG. 2C. Carrier 44 is preferably made of substantially transparent material, e.g., polycarbonate or glass, allowing observation of cells therethrough.

Carrier 44 is attached to the periphery of the bottom rim of a hollow 26 (for example by welding or adhesive) to device body 20 so that picowell array 10 faces upwards defining a chamber 54 with a circular opening 120 at the top, the walls of hollow 26 as sides and carrier 44 as a bottom surface. Preferably, device body 20 is fashioned from a transparent material. Passing through device body 20 and emerging out into chamber 54 are liquid inlet 76 and liquid outlet 78. The walls of opening 120 are provided with threads 122.

Gasket 106 is configured to rest inside hollow 26 on a ledge located at the bottom of opening 120.

Chamber cover 108 is a substantially planar disk made of transparent material. Chamber cover 108 constitutes a removable top wall of chamber 54. On the sides of chamber cover 108 are threads 124 configured to mate with threads 122 of the walls of opening 120.

Device 118 is substantially similar to device 104 depicted in FIGS. 7A-7D. A significant difference is in the nature of the respective force applicators.

In device 104 magnets 98 and 102 together constitute a force applicator that, when contacted together apply a substantially uniformly distributed force around the periphery of chamber cover 108, the removable top wall of chamber 54, in a direction to retain chamber cover 108 secured to chamber 54. In contrast, in device 118 threads 122 and 124 together constitute a force applicator configured to apply a substantially uniformly distributed force around the periphery of chamber cover 108, the removable wall of chamber 54 in a direction to retain chamber cover 108 secured to chamber 54.

Performance of experiments using device 118 is substantially analogous to performance of experiments using device 104. A flow generator such as a pump or syringe is attached to liquid inlet 76 of device 118. Chamber cover 108 is removed, allowing access to chamber 54 through top opening 120. Medium and living cells 56 that are denser than the medium are introduced (together or separately) into chamber 54 through top opening 120. Cells 56 settle by sedimentation into picowells of picowell array 10. Gasket 106 is placed on the ledge inside hollow 26. Chamber cover 108 is placed over opening 120 and rotated so that threads 122 and threads 124 mate. Chamber cover 108 is screwed into opening 120 until gasket 106 is sufficiently compressed to ensure a substantially leak proof seal.

Cells 56 held in picowell array 10 may be then observed and/or manipulated as described above and in the art, including during and subsequent to introduction of active entities through inlet 76. As discussed above, device 118 is configured to allow simple loading of cells 56 into picowells of picowell array 10 and to allow performance of long-duration experiments free of leaks even with relatively high pressure and continuous inflow of liquids through inlet 76 due to the use of a force applicator that applies a substantially uniformly distributed force around the periphery of chamber cover 108 to retain chamber cover 108 secured to chamber 54.

Figure 9:
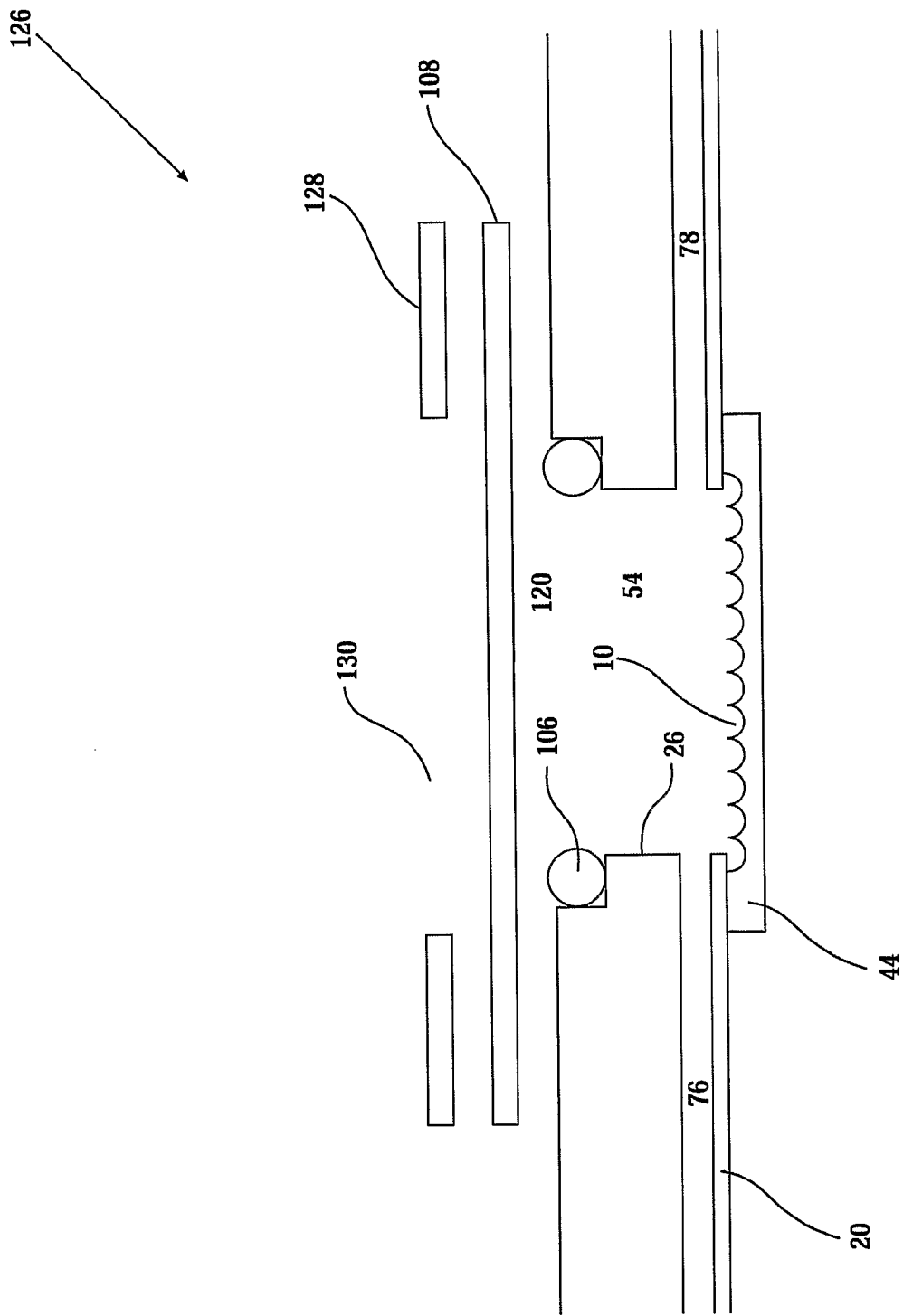
FIG. 9 depicts an embodiment of a device of the present invention including a chamber with a removeable top wall and a picowell array on the top surface of the bottom wall of the chamber.

An additional embodiment of a device of the present invention, 126, is depicted in side cross-section in FIG. 9. In FIG. 9 are depicted five individual components of device 126: a carrier 44, a device body 20, a gasket 106, a chamber cover 108 and a rigid force distributor 128.

Carrier 44, is a substantially planar component including a picowell array 10 as a feature on an upper surface, similar to carrier 44 of device 18 depicted in FIG. 2C. Carrier 44 is preferably made of substantially transparent material, e.g., polycarbonate or glass, allowing observation of cells therethrough.

Carrier 44 is attached to the periphery of the bottom rim of a hollow 26 (for example by welding or adhesive) to device body 20 so that picowell array 10 faces upwards defining a chamber 54 with an opening 120 at the top, the walls of hollow 26 as sides and carrier 44 as a bottom surface. Preferably, device body 20 is fashioned from a transparent material. Passing through device body 20 and emerging out into chamber 54 are liquid inlet 76 and liquid outlet 78.

Gasket 106 is placed on a ledge located near the rim of opening 120 so that the top edge of gasket 106 is somewhat higher than the top surface of device body 20.

Chamber cover 108 is substantially planar component made of transparent material. Chamber cover 108 constitutes a removable top wall of chamber 54.

Rigid force distributor 128 is a substantially planar rigid component with a gap 130 through the middle, e.g., a polytetrafluoroethylene-coated steel washer. Gap 130 through rigid force distributor 128 is of a size and shape to allow an unimpeded view therethrough of cells held in picowell array 10 when rigid force distributor 128 is placed over chamber cover 108, as described below.

Device 126 is substantially similar to device 104 depicted in FIGS. 7A-7D. A significant difference is in the nature of the respective force applicators. In device 104, magnets 98 and 102 together constitute a force applicator configured to secure a respective removable top wall of chamber 54 (chamber cover 108), by applying a substantially uniformly distributed force around the periphery of the respective moveable wall in a direction to retain the moveable wall secured to chamber 54. In contrast, in device 126 rigid force distributor 128, together with a force applying component such as a clamp, tack, press or clip (not depicted), constitute components of a force applicator configured to apply a substantially uniformly distributed force around the periphery of the respective moveable wall (chamber cover 108) in a direction to retain the moveable wall secured to chamber 54.

Performance of experiments using device 126 is substantially analogous to performance of experiments using device 104 depicted in FIGS. 7A-7D. A flow generator such as a pump or syringe is attached to liquid inlet 76 of device 126. Chamber cover 108 is removed, allowing access to chamber 54 through top opening 120. Medium and living cells 56 that are denser than the medium are introduced (together or separately) into chamber 54 through top opening 120. Cells 56 settle by sedimentation into picowells of picowell array 10. Gasket 106 is placed on the ledge inside hollow 26. Chamber cover 108 is placed over opening 120 and rigid force distributor 128 is placed over chamber cover 108 so that gap 130 allows an unimpeded view of picowell array 10 through chamber cover 108. A force-applying component such as a clamp, tack, press or clip (not depicted) is used to apply a force at least two points around the perimeter of rigid force distributor 128. The magnitude of the force applied is sufficient to compress gasket 106 enough to ensure a substantially leak proof seal. Since rigid force distributor 128 is rigid, the force applied by force-applying component is substantially uniformly distributed around the periphery of chamber cover 108 to retain chamber cover 108 secured to chamber 54.

Cells 56 held in picowell array 10 may then be observed and/or manipulated as described above and in the art, including during and subsequent to introduction of active entities through inlet 76. As discussed above, device 126 is configured to allow simple loading of cells 56 into picowells 12 and to allow performance of long-duration experiments free of leaks even with relatively high pressure and continuous inflow of liquids through inlet 76 due to the use of a force applicator that applies a substantially uniformly distributed force around the periphery of chamber cover 108 to retain chamber cover 108 secured to chamber 54.

Figure 10A:
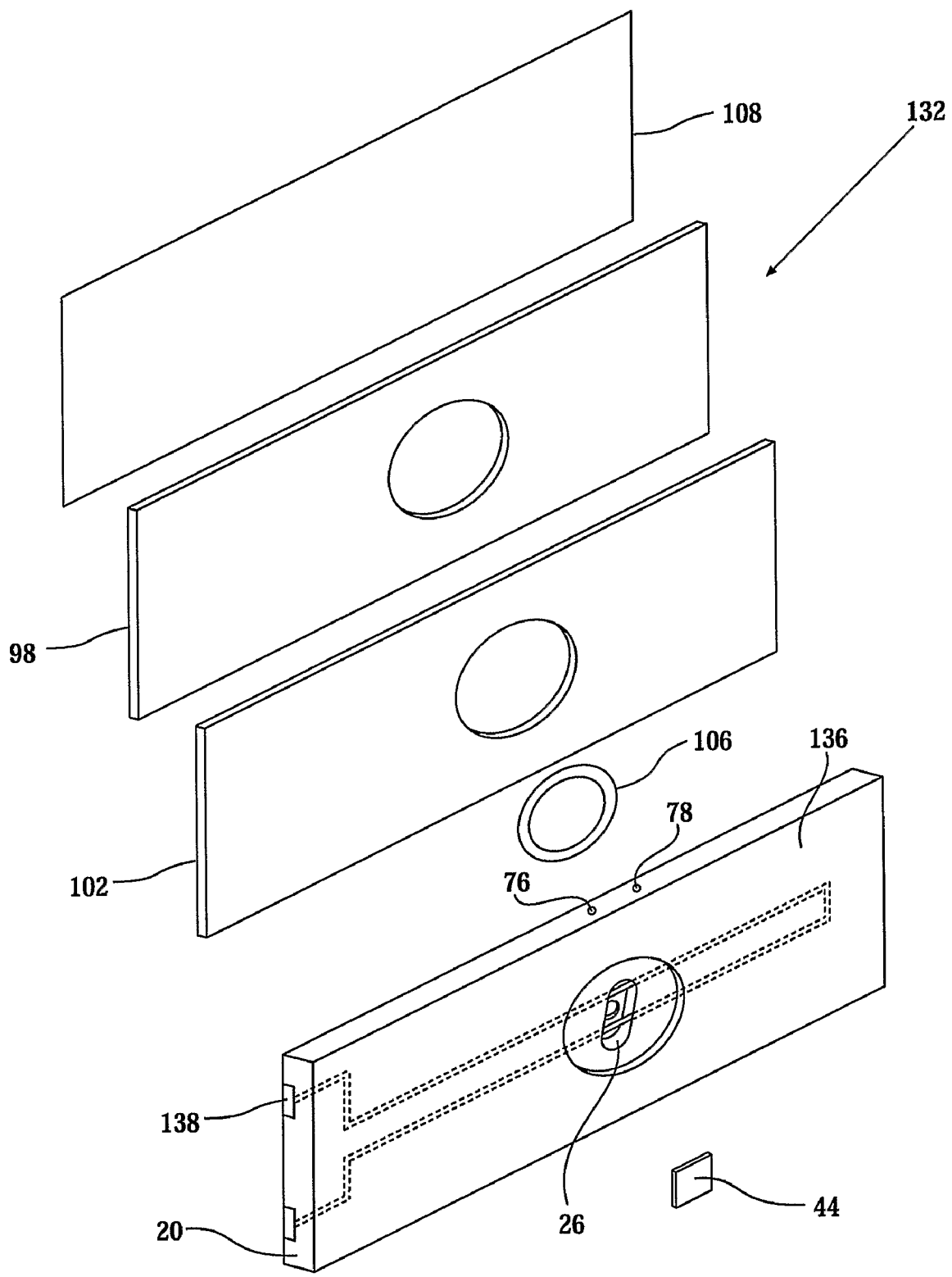
FIGS. 10A-10C depict an embodiment of a device of the present invention including a chamber with a removeable top wall and a picowell array on the top surface of the bottom wall of the chamber.
Figure 10B:
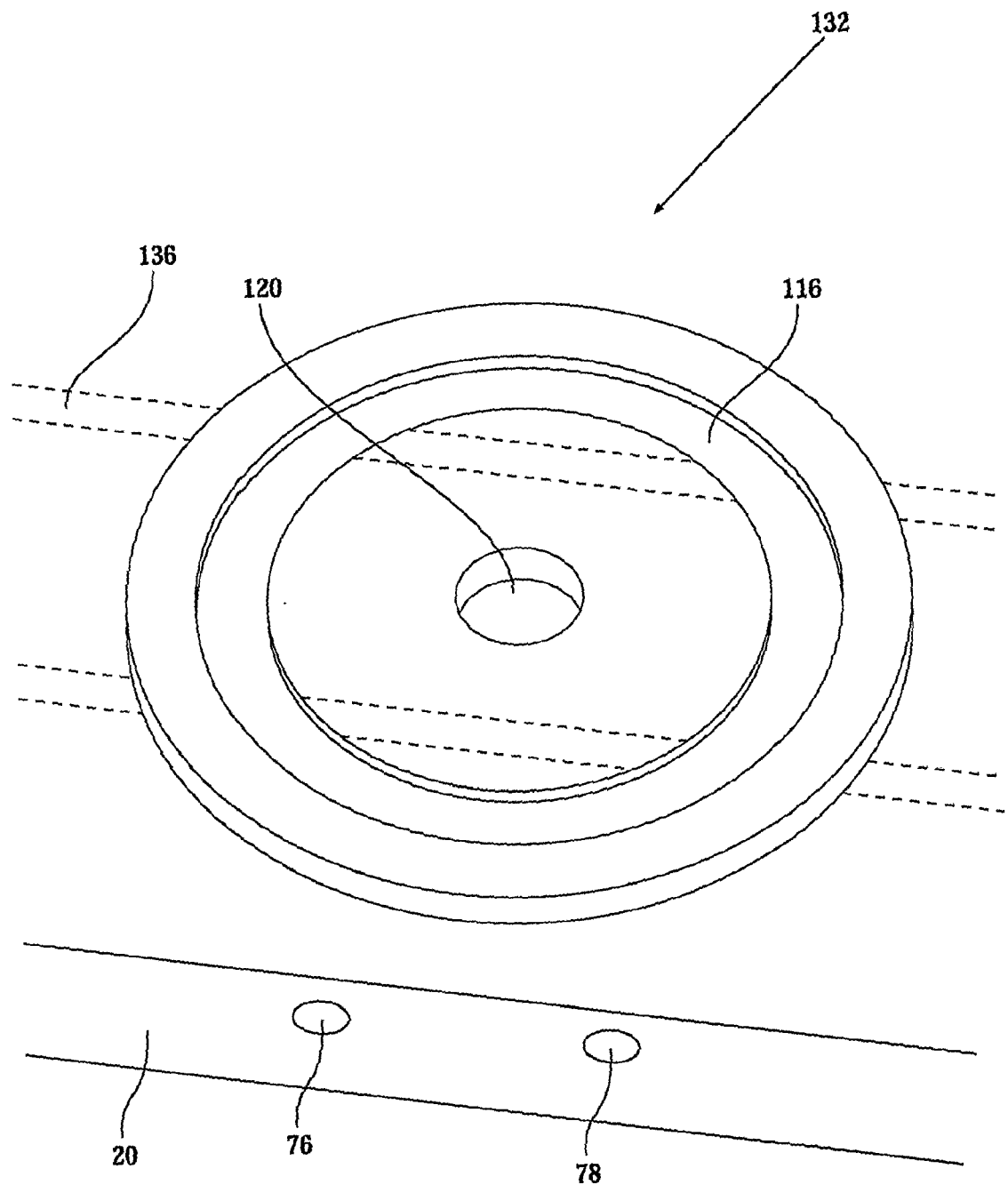
Figure 10C:
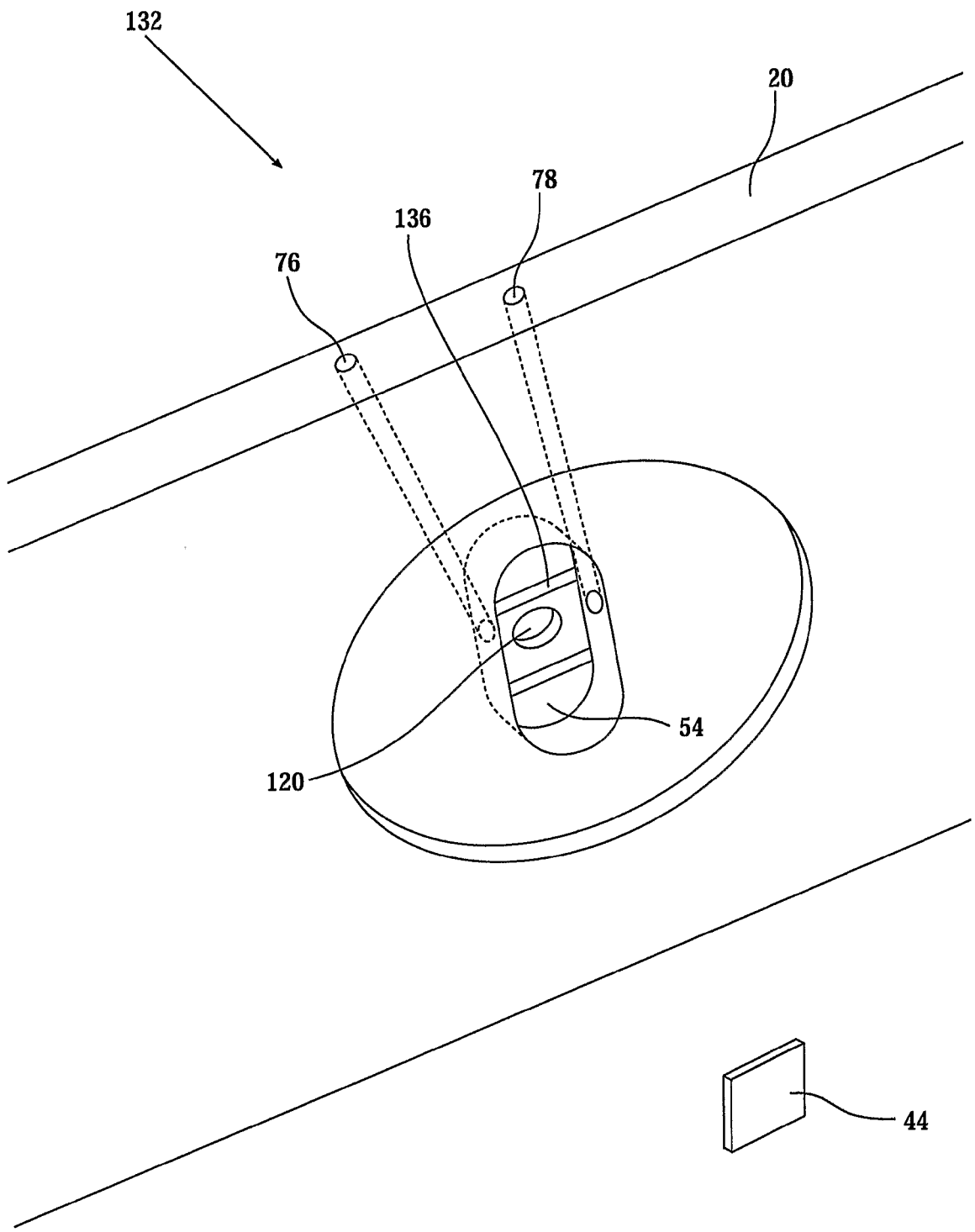
Figure 10D:
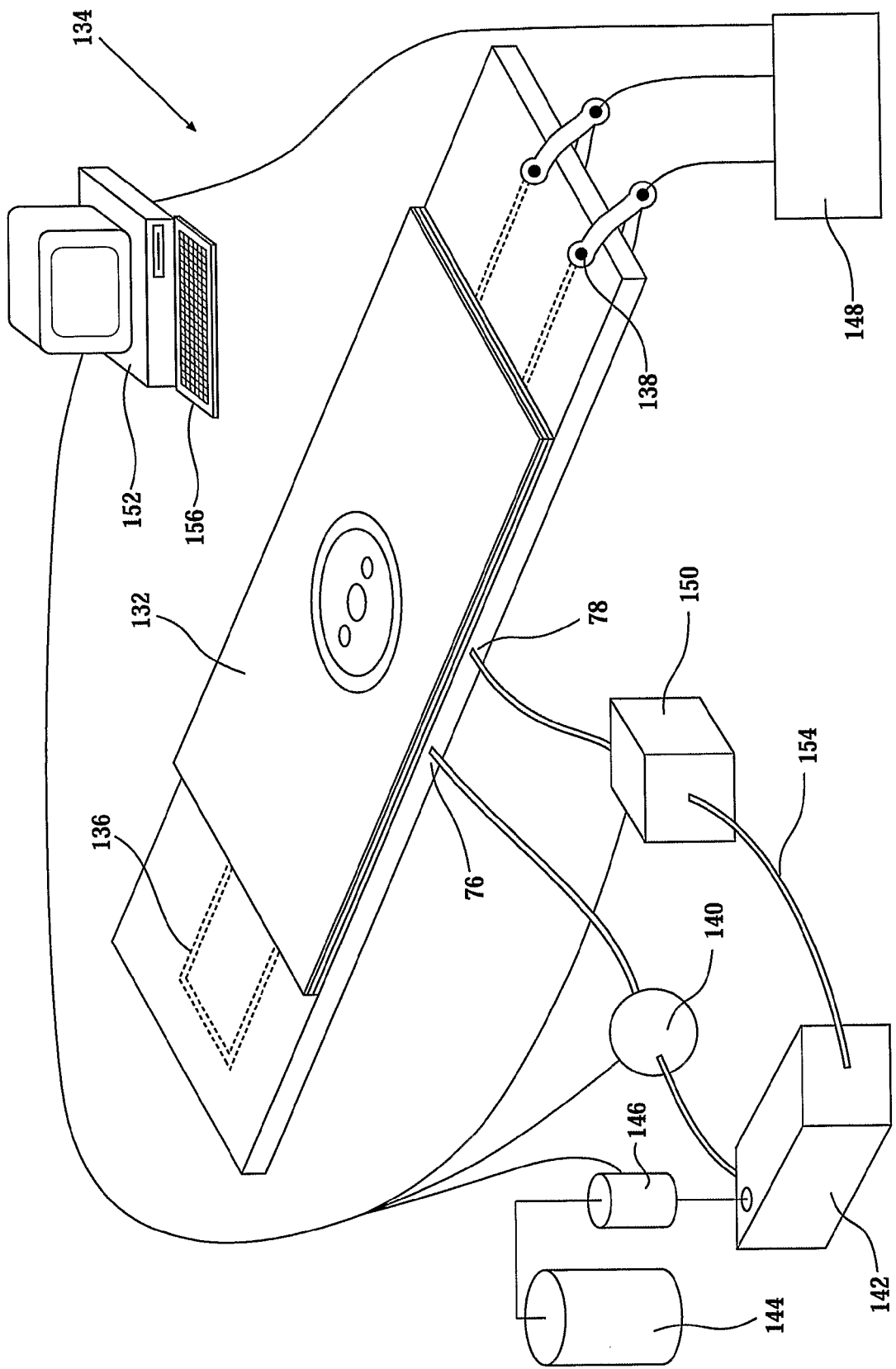
FIG. 10D depicts an embodiment of a device of the present invention integrated with other components to constitute a microincubator.

An additional embodiment of a device of the present invention, 132, is depicted in an exploded view in perspective in FIG. 10A (to scale), a close-up showing details of device body 20 from the top in FIG. 10B (to scale), and a close-up showing details of device body 20 from the bottom in FIG. 10C. A fully assembled device 132 integrated in a system 134 is depicted in FIG. 10D.

Device 134 essentially consists of six components: a carrier 44, a device body 20, a lower retaining magnet 102, a gasket 106, an upper retaining magnet 98 and a chamber cover 108.

Carrier 44, is a substantially planar component including a picowell array 10 as a feature on an upper surface, similar to carrier 44 of device 18 depicted in FIG. 2C. Carrier 44 is preferably made of substantially transparent material, e.g., polycarbonate or glass, allowing observation of cells therethrough.

Carrier 44 is attached to the periphery of the bottom rim of a hollow 26 (for example by welding or adhesive) to device body 20 so that picowell array 10 faces upwards defining a chamber 54 with a circular opening 120 at the top, the walls of hollow 26 as sides and carrier 44 as a bottom surface. Preferably, device body 20 is fashioned from a transparent material.

Passing through device body 20 and emerging out into chamber 54 are liquid inlet 76 and liquid outlet 78, see especially FIG. 10C. Embedded inside device body 20 is heating wire 136 and electrical contacts 138 (see especially FIG. 10A), where heating wire 136 passes in the proximity of chamber 54. Heating wire 136 acts as a temperature controller, so when electrical current is passed through heating wire 136, heating wire 136 generates heat, raising the temperature of medium held in chamber 54.

Similarly to gasket 106 of device 104 depicted in FIGS. 7A-7D, gasket 106 of device 134 is configured to fit in a circular groove 116 located on the top surface of device body 20 surrounding opening 120.

Similarly to lower retaining magnet 102 of device 96 depicted in FIG. 6, lower retaining magnet 102 of device 134 is planar and is attached (for example using adhesive) to the upper surface of device body 20. Lower retaining magnet 102 is provided with an opening that fits about gasket 106.

Chamber cover 108 is a substantially planar component made of a transparent material having substantially the same outer dimensions of device body 20.

Similarly to upper retaining magnet 98 of device 96 depicted in FIG. 6, upper retaining magnet 98 of device 134 is planar and is attached (for example using adhesive) to the lower surface of chamber cover 108. Upper retaining magnet 98 is provided with an opening that fits about gasket 106.

Similarly to devices 104, 118 and 126, device 134 is provided with a picowell array 10 on a top surface of a carrier 44 and constitutes a bottom wall of chamber 54. Similarly to devices 96, 104, 118 and 126 is provided with a non-capillary liquid inlet 76 and liquid outlet 78 in fluid communication with chamber 54 and for use generally requires attachment of a flow generator to liquid inlet 76. Analogously to device 104 depicted in FIGS. 7A-7D, chamber cover 108 of device 134 constitutes a removable upper wall of chamber 54. Analogously to device 96 depicted in FIG. 6, in device 134 magnets 98 and 102 are configured to secure chamber cover 108 to device body 20 so as to substantially seal chamber 54. Magnets 98 and 102 together constitute a force applicator that, when contacted, together apply a substantially uniformly distributed force around the periphery of opening 120 of chamber 54 in a perpendicular direction so as to retain chamber cover 108 secured to device body 20 and thus to chamber 54.

In embodiments, a device 134 is used substantially similarly as a device 104 described above.

As discussed above, device 96 (depicted in FIG. 6), device 104 (depicted in FIGS. 7A-7D), device 118 (depicted in FIG. 8), device 126 (depicted in FIG. 9) and device 132 (depicted in FIGS. 10A-10C) include at least one picowell inside a chamber with at least one moveable wall that allows performance of long-duration experiments substantially free of leaks around the respective moveable wall/chamber interface due to the use of a force applicator configured to removeably apply a substantially uniformly distributed force around the periphery of the moveable wall in a direction to retain the moveable wall secured to the chamber. In embodiments of the present invention, such devices are integrated with other components that allow performance of long duration experiments with living cells and can be considered as miniature incubators, or microincubators. One such embodiment, depicted in FIG. 10D, is system 134 including a picowell-bearing device 132 of the present invention.

System 134 includes, in addition to picowell-bearing device 132, a flow-generator 140, a liquid reservoir 142, a gas reservoir 144, a gas inlet valve 146, an electrical power supply 148, a detector array 150 and a controller 152.

Flow-generator 140 (e.g., a pump such as a peristaltic pump) is configured to generate a flow of liquids from liquid reservoir 142 into inlet 76 of picowell-bearing device 132. Flow generator 140 is a variable flow generator and can be set to provide varying flow rates of liquids into inlet 76.

Liquid reservoir 142 is a vessel configured to hold liquids, such as medium.

Gas reservoir 144 is in communication with liquid reservoir 142 through gas inlet valve 146. When gas inlet valve 146 is open, gas from gas reservoir 144 bubbles through liquid held in liquid reservoir 142, increasing the content of the gas in the liquid. Typical gases include oxygen and carbon dioxide.

Electrical power supply 148 is functionally associated with heating wire 136 through electrical contacts 138.

Detector array 150 includes sensors for measuring various properties of a liquid passing through tube 154 such as oxygen and carbon dioxide content (e.g., by infrared absorption), temperature, pH, osomolarity and/or conductivity.

Controller 152, a computer, is functionally associated with flow generator 140, gas-inlet valve 146, electrical power supply 148, detector array 150 and user interface 156. Based on stored data, instructions received through user interface 156 and measurements received from detector array 150, controller 152 controls the rate of liquid flow from fluid reservoir 142 through chamber 54 of device 132 by controlling flow generator 140, the gas content of such a liquid by controlling gas-inlet valve 146 and the temperature of liquid in chamber 54 by controlling electrical power supply 148.

For example, a system such as 134 is assembled. Chamber cover 108 and associated upper retaining magnet 98 are separated from device body 20, allowing access to chamber 54 through top opening 120. Medium and living cells 56 are introduced (together or separately) into chamber 54 through top opening 120. Cells 56 settle by sedimentation into picowells 12 of picowell array 10. Gasket 106 is placed in groove 116. Chamber cover 108 and associated upper retaining magnet 98 are placed in proximity of device body 20 so that magnets 98 and 102 are mutually attracted, holding chamber cover 108 firmly in place in accordance with the present invention. Medium is placed in liquid reservoir 142. A desired gas, typically carbon dioxide to encourage cell development, is placed in gas reservoir 144.

Controller 152 is activated to perform a desired experiment. Flow generator 140 is activated, producing a flow of medium from liquid reservoir 142 through chamber 54 that supplies nutrients and removes waste products from the vicinity of cells 56 held in picowells of picowell array 10. Controller 152 receives a reading of the temperature of medium flowing through tube 154 and adjusts power to heating wire 126 supplied by electrical power supply 148 to ensure that medium in chamber 54 is at a desired temperature. Controller 152 receives a reading of the carbon dioxide content of medium flowing through tube 154 and if necessary activates gas inlet valve 146 to increase the carbon dioxide content of medium in liquid reservoir 142.

Cells 56 held in picowell array 10 are then observed as described above and in the art, including during and subsequent to introduction of active entities through inlet 76.

In system 134, medium held in chamber 56 is heated using heating wires 136 embedded in device body 20. In embodiments, heating is performed by an external heating element, for example using a Peltier heating device as a liquid temperature controller on which a picowell-bearing device rests. In embodiments liquid is heated, for example using a liquid temperature controller that heats the liquid in a liquid reservoir 142, in a flow-generator 140, or in tubing 154 connected to a liquid inlet 76 or liquid outlet 78.

System 134 is a closed system, that is, liquid exiting chamber 54 of picowell-bearing device 132 reenters liquid reservoir 142, processed (e.g., by the addition of gas from gas reservoir 144) and then pumped back into chamber 54. Such a configuration allows for the construction of a compact system. In embodiments of the present invention, a system is an open system, that is, liquid exiting a chamber 54 of a picowell-bearing device is not recycled back into chamber 54, similarly to systems taught in embodiments of PCT patent applications IL2001/00992 published as WO2003/035824 of the inventor.

The picowell-bearing devices of the present invention described above, 18, 66, 72, 88, 90, 96, 104, 126 and 132 include one picowell array 10. In embodiments, a device of the present invention, such as device 118, includes more than one picowell array. For use, cells are loaded in each one of the more than one picowell arrays, preferably a different type in each one of picowell arrays, allowing performance of experiments on more than one type of cell using one device body.

The devices of the present invention are picowell-bearing devices, that is, the devices include at least one picowell, preferably an array of picowells. Preferably, individual picowells of a picowell array are individually addressable. For ease of optical study and observation, it is preferred that the bottoms of all picowells be substantially coplanar: coplanarity allows for optical observation of many cells (whether by scanning or simultaneously using a wide-angle observation component) without the need for time consuming and technically difficult to implement refocusing.

As noted above, components of a device of the present invention are preferably fashioned of transparent material, especially in the vicinity of the picowells allowing illumination and/or observation of cells held in the picowells. In embodiments of the present invention, the transparent material has an index of refraction similar to that of water, for example an index of refraction less than about 1.4, less than about 1.38, less than about 1.36, less than about 1.35 and even less than about 1.34. When such a material is used, the material is substantially invisible.

Preferably, picowells of a picowell array are juxtaposed. By juxtaposed is meant that in an area where picowells are found, the picowells are nearby and side by side so that most of the area is picowell area and little of the area is inter picowell area. According to a feature of the present invention, by juxtaposed is meant that the inter picowell area between two picowells is less than or equal to 0.35, 0.25, 0.15, 0.10 or even 0.06 of the sum of the areas of the two picowells. In embodiments of the present invention it is preferred that the inter picowell area be substantially zero, that is that the rims of picowells are substantially knife-edged.

As the teachings of the present invention are directed to cellular biology, it is generally preferred that the picowells be small so as to avoid having a large number of cells held in any one picowell. Thus, generally, the dimensions of the picowells are generally up to about 250, 200, 150, 100, 50, 25, 20, 15 or even 10 microns. By dimensions is meant the usual meaning of the word and is dependent on the shape of the picowell. For example, for hexagonal or circular picowells, the term dimension refers to diameter. For square or triangular picowells is meant the longest dimension of the square or triangle, respectively. The exact dimensions of individual picowells depends on the type (and consequently size) of cells to be studied and the types of experiments and studies that are to be performed. Since different types of cells have different sizes, generally a picowell array of the present invention has picowells of a size to accommodate one or more cells of the type to be studied. In embodiments it is preferred that an individual picowell be of a size so as to hold no more than one living cell of a certain size. In embodiments it is preferred that the picowell be of a size so as to held no more than a predetermined number of cells of a certain size (e.g., two or three cells simultaneously).

In some embodiments of the present invention, picowells are dimples or depressions on the bottom surface of the picowell array. In other embodiments the picowells are substantially enclosures of dimensions so that at least one cell of a certain size is containable, preferably but not necessarily substantially entirely, within the enclosure, each enclosure having an opening at the surface, the opening defined by a first cross section of a size allowing passage of cell of the certain size The exact dimensions of the individual enclosures depends on the type (and consequently size) of cells to be studied and the types of experiments and studies that are to be performed. The volume of such enclosure picowells is typically less than $1.56 \times 10^{-11}$ liter (corresponding to the volume of a 250 micron cube), less than $1 \times 10^{-11}$ liter (corresponding to the volume of a 200 micron cube), less than $1 \times 10^{-12}$ liter (corresponding to the volume of a 100 micron cube), less than $1 \times 10^{-13}$ liter (corresponding to the volume of a 50 micron cube), less than $1 \times 10^{-14}$ liter (corresponding to the volume of a 25 micron cube) and even less than $1 \times 10^{-15}$ liter (corresponding to the volume of a 10 micron cube). The area of the first cross section, corresponding to the size of the opening of a respective enclosure is typically less than about 62500 micron$^2$ (corresponding to the area of a 250 micron square), about 40000 micron$^2$ (corresponding to the area of a 200 micron square), 10000 micron$^2$ (corresponding to the area of a 100 micron square), 2500 micron$^2$ (corresponding to the area of a 50 micron square), 625 micron$^2$ (corresponding to the area of a 25 micron square) or even less than about 100 micron$^2$ (corresponding to the area of a 10 micron square).

Embodiments of a device of the present invention have dimensions near those of a standard microscope slide, i.e., 28.4 mm wide by 76.2 mm long, e.g., devices 18, 66, 104 and 132. For example, in an embodiment of device 18 the center of picowell array 10 is 18.1 mm from the edge of device body 20. The width between the two rail walls 38 is 24.5 mm, between the distal edges of gaps 32 19.5 mm, of plateau 28 in the vicinity of capillary channel 46 and of plateau 28 at the end of the waste reservoir region 50 15.2 mm. The thickness of device body 20 is 2.3 mm. The radius of hollow 26 is 1 mm and has a volume of $5 \times 10^{-6}$ liter. When sliding base 22 is in place, the volume between sliding base 22 and plateau 28 upstream of hollow 26 is about 10 microliter while the volume between sliding base 22 and plateau 28 downstream of hollow 26 is about 150 microliter.

Methods of Manufacture of a Device of the Present Invention

In general, manufacture and assembly of a device of the present invention is well within the ability of one skilled in the art upon perusal of the description and figures herein using any suitable method with which one skilled in the art is well acquainted. Many such methods are described in relation to the manufacture of picowell-bearing devices in PCT patent applications IL2001/00992 published as WO2003/035824, IL2004/000571 published as WO2004/113492, IL2004/000194 published as WO2004/077009, IL2004/000661 published as WO2005/007796, and unpublished IL2005/000801. Suitable methods include methods that employ one or more techniques including but not limited to casting, embossing, etching, free-form manufacture, injection-molding, microetching, micromachining, microplating, molding, spin coating, lithography or photo-lithography.

In embodiments of the present invention, an entire device of the present invention and all components thereof are made of one material. In other embodiments, a device of the present invention is made up of a number of different materials. In embodiments of the present invention, individual components, for example a device body, are made of a number of different materials as a plurality of layers or as a coated structure.

In an embodiment of the present invention, the walls of picowells are integrally formed with a surface of a device body (e.g., as in device 72). In embodiments including a separate picowell-bearing component (e.g., a carrier 44) the picowell-bearing component is made of any suitable material, the same as or different than the material from which the respective device body is made. Suitable materials from which to make components of a device of the present invention such as a carrier, a device body, a sliding base and the like include but are not limited to ceramics, elastomers, epoxies, glasses, glass-ceramics, metals, plastics, polycarbonates, polydimethylsiloxane, polyethylenterephtalate glycol, polymers, polyurethane, polymethyl methacrylate, polystyrene, polytetrafluoroethylene, polyvinyl chloride, rubber, silicon, silicon oxide, silicone rubber and sol-gels.

Manufacture of a device body 20 or carrier 44 with integrally formed picowells that are a feature of the component, of a device body without integrally formed picowells or another picowell-bearing component is clear to one skilled in the art upon perusal of the description herein. A preferred method is analogous to the methods disclosed by the inventor in PCT Patent Application No. IL01/00992, in PCT Patent Application No. IL04/00571 and in PCT Patent Application No. IL04/00661. Such a method includes a) contacting a precursor material with a template including a negative of features of the device body or picowell-bearing component so as to create the desired features in the precursor material, the features including the picowell array; b) fixing the features in the precursor material so as to fashion an incipient device body or picowell-bearing component; and c) processing the incipient device body or picowell-bearing component so as to fashion the device body or picowell-bearing component of the present invention.

In an embodiment of the present invention, a picowell-bearing component is fashioned inside a device body by contacting an appropriate template with a moldable precursor material when the precursor material is inside a depression. Such an embodiment is discussed in detail hereinbelow.

Components of a device of the present invention such as a device body with integrally formed picowells, a device body without integrally formed picowells or a picowell-bearing component of the present invention are preferably made according to the methods discussed hereinbelow.

A first method of the present invention for making a component of the present invention is substantially by contacting a precursor material with a template, the template having a negative of some of the features of the component (especially the picowells) thus creating the features in the precursor material. The features are subsequently fixed in the precursor material making an incipient component. After any further required processing of the incipient component (which may be limited to simply separating the template from the incipient component), the device is assembled from the individual components.

Depending on the precursor material, fixing includes, but is not limited to, methods such as heating the precursor material, cooling the precursor material, curing the precursor material, polymerizing the precursor material, cross-linking the precursor material, irradiating the precursor material, illuminating the precursor material, gelling the precursor material, exposing the precursor material to a fixative and waiting a period of time. By fixative is meant an agent that causes the precursor material to change to the fixed state and is used herein as a general term for such materials as fixatives, hardeners, polymerization/crosslinking/curing initiators, catalysts and agents. It is important to note that in some cases a precursor material is produced by mixing two or more components which thereafter change to a fixed state, for example, by simply waiting a period of time.

In one preferred embodiment of the present invention, the precursor material is a irreversibly deformable precursor material. Herein by irreversibly deformable precursor material is meant a material that does not recover a shape after deformation and so there is usually no need for a separate action to fix the features in the precursor material beyond separating the produced component from the template. In such cases, the precursor material does not substantially chemically change subsequent to contact with the template. Examples of suitable irreversibly deformable precursor materials include waxes, paraffins, plastics, polymers and the like. In such an embodiment, a preferred template is a stamp, and the contacting of the template with the precursor material is substantially stamping the features of the component into the precursor material, preferably under controlled thermal conditions.

In another preferred embodiment of the present invention, the precursor material is a reversibly deformable precursor material. Herein by reversibly deformable precursor material is meant a material that is capable of recovering shape after deformation and includes gellable fluids, polymerizable materials, powders, fluids and thermoplastic materials.

In a preferred embodiment, the reversibly deformable precursor material is a thermoplastic material at a pliable temperature. Subsequent to the contacting of the template but before the contact is finished, the thermoplastic material is cooled, thus fixing the desired features in the incipient component.

In another preferred embodiment, the reversibly deformable precursor material is a polymerizable material (e.g., a monomer solution, a crosslinkable polymer, a vulcanizable polymers, a polymerizable fluids or a thermosetting resin). Subsequent to the contacting of the template but before the contact is finished, the polymerizable material is polymerized, thus fixing the desired features in the incipient component. In such cases, the precursor material and the material from which the component is made are chemically dissimilar (for example, have the relationship of monomer to polymer).

One preferred polymerizable precursor material is a non-cured polydimethylsiloxane precursor mixture. A mixture of two polydimethylsiloxane components (the prepolymer and curing agent) are mixed together in the desired ratio (preferably about 10:1, but ratios between about 5:1 and about 20:1 are generally suitable) to give a polydimethylsiloxane precursor mixture, the mixture degassed and contacted with the template. The features are fixed by the curing of the mixture. Curing of polydimethylsiloxane precursor generally takes place at room temperature for about 24 hours and, when desired, is accelerated by heating. For example it has been found that components of the device of the present invention made of polydimethylsiloxane are ready for further processing within 2 hours when cured at 60° C. or within 15 minutes when cured at 150° C. A detailed review of methods for the production of micronic features such as picowells from polydimethylsiloxane suitable for implementing the teachings of the present invention are known in the art and discussed, for example, in Ng et al., *Electrophoresis* 2002, 23, 3461-3473 and Duffy et al., *Anal. Chem.* 1998, 70, 4974-4984.

Another preferred polymerizable precursor material is urethane that is polymerized to yield polyurethane.

Another preferred reversibly deformable precursor material is a gellable fluid. After the gellable fluid is brought in contact with the template, the features are fixed by gelling the gellable fluid to yield a gel. Most preferred are gellable fluids that produce a hydrogel.

Gellable fluids known in the art include fluids that gel upon heating, fluids that gel upon cooling, fluids that gel upon irradiation or illumination, fluids that gel as a result of contact with a gelling reagent and fluids that gel after a period of time. Preferred gellable fluids for implementing the teachings of the present invention include solutions of agars, agaroses, low melting temperature agaroses, alginates, proteins, protein polysaccharides, $Ca^{2+}$-inducable alginates (especially those that gel at room temperature) and polysaccharides.

One preferred gellable fluid is a low-melting temperature agarose solution. Such a solution is fluid at temperatures that do not harm living cells (e.g., 20° C.) and gel at low temperatures that do not harm living cells (e.g., 4° C.). An exceptionally suitable agarose for implementing the teachings of the present invention that may be purchased, for example, from Cambrex Bio Science Rockland Inc. (Rockland, Me., USA) is HGS-LMP Agarose 0.5% in PBS (Catalogue Nr. 50221).

Another preferred gellable fluid is an alginate solution which gels upon contact with a gelling reagent, the preferred gelling reagent being a solution having a $Ca^{2+}$ ion concentration of greater than about $1 \times 10^{-6}$ M. An exceptionally useful gelling agent is a $20 \times 10^{-3}$ M calcium gluconate solution. Suitable alginate solutions can be purchased from Pronova Biopolymers (Drammen, Norway) and include, for example, Protanal LF120 1% in water and Protanal LF200 1% in water.

The template having a negative of the features is, for example, a stamp or a mold, and is generally made of any suitable material that is more rigid than a respective precursor material. Suitable materials include but are not limited to reversibly deformable materials, irreversibly deformable materials, ceramics, epoxies, glasses, glass-ceramics, metals, plastics, polycarbonates, polydimethylsiloxane, polyethylenterephtalate glycol, polymers, polymethyl methacrylate, paraffins, polytetrafluoroethylene, polystyrene, polyurethanes, polyvinyl chloride, silicon, silicon oxide, silicone rubbers, sol-gels and wax.

The template is made, for example, using methods with which one skilled in the art is acquainted such as casting, embossing, etching, free-form manufacture, injection-molding, microetching, micromachining, microplating, molding, lithography or photo-lithography.

In an embodiment, a device of the present invention is made by making picowells as described above inside a hollow (such as 26) of a device body (such as 20). Suitable device bodies include but are not limited to device bodies made of reversibly deformable materials, irreversibly deformable materials, ceramics, epoxies, glasses, glass-ceramics, metals, plastics, polycarbonates, polydimethylsiloxane, polyethylenterephtalate glycol, polymers, polymethyl methacrylate, polystyrene, polytetrafluoroethylene, polyurethanes, polyvinyl chloride, silicon, silicon oxide, silicone rubbers and sol-gels. In such a case, a precursor material for making picowells is placed into the depression of the device body. A template is then placed inside the depression so as to make contact with the precursor material and the precursor material is fixed as described above. Such an embodiment has the advantage that a device body devoid of picowells of virtually any material is mass-produced. Subsequently, a template is made and used for fixing picowells of virtually any desired size, number and arrangement in the device body.

In another embodiment noted above, a template including the negative of the desired features excepting picowells is contacted with the precursor material so as to form a device body with a depression devoid of picowells. Subsequently, a grid-like component, constituting substantially the walls of the picowells of the picowell array, is attached using an appropriate method, for example, adhesives (for example, light curable adhesives, such as light curing adhesive 3051 or 3341 manufactured by Henkel Loctite Deutschland GmbH, München, Germany) or surface treatments such as anodic bonding, fusion bonding or plasma treatment such as plasma discharge (exceptionally suitable for attaching polydimethylsiloxane, see Duffy et al., *Anal. Chem.* 1998, 70, 4974-4984).

Another method of making a picowells in a device body includes photolithography of a photoresist material placed on a substrate, a commercially available process (for example, from Micro Resist Technology GmbH, Berlin, Germany) with which one skilled in the art is well-acquainted. In brief, a template including the negative of the desired features excepting picowells is contacted with the precursor material so as to form a device body with a depression devoid of picowells. Subsequently, a high aspect ratio photoresist material (e.g., SU-8 thick photoresist fluid, MicroChem Corporation, Newton Mass., USA) is placed in the depression as a uniformly thick film. A preferred method of achieving a uniformly thin film of a photoresist fluid is by spin coating, that is, the photoresist fluid is placed in the depression of the device body and the device body rotated about a perpendicular axis. As a result of the rotation the photoresist fluid forms a uniformly thick film, typically between about 5 microns and about 20 microns thick. Once a film of uniform thickness of photoresist material is achieved, the photoresist material is illuminated through a mask, the mask being substantially a template or master of the desired picowells. Developing of the precursor with the selectively fixed film removes the non-fixed areas of the film. In such a way the picowell array is made up of a fixed photoresist layer resting on a device body where the picowells are carved into the photoresist layer and the bottom of the picowells is the surface of the precursor plate. Using a photolithography method, picowells having a flat-bottom surface are easily produced.

The components of a device of the present invention are made of any suitable material. Suitable materials include but are not limited to ceramics, epoxies, glasses, glass-ceramics, metals, plastics, polycarbonates, polydimethylsiloxane, polymers, polyethylenterephtalate glycol, polymethyl methacrylate, polystyrene, polytetrafluoroethylene, polyurethanes, polyvinyl chloride, silicon, silicon oxide and sol-gels.

Another method of making a device of the present invention comprises attaching one or more picowell-bearing components to a precursor plate using an appropriate method, for example, using an adhesive or a surface treatment such as a plasma treatment, for example as described above. A preferred picowell-bearing component is a device body comprising a plurality of picowells disposed on a surface. Preferred device bodys include those described in PCT Patent Application No. IL 01/00992 or PCT Patent Application No. IL 04/00571.

Some embodiments of the device of the present invention comprise picowells where the inside surface of the picowells (with which held cells potentially make physical contact) is coated with a layer of some desired coating material, for example a coating material that influences the proliferation of living cells as described in PCT Patent Application No. IL04/00571.

One skilled in the art is acquainted with many ways and many coating materials with which to coat an inside surfaces of picowells of a device of the present invention.

One preferred method of coating inside surfaces of picowells of a device of the present invention, applicable to virtually any device produced by virtually any method, comprises contacting a precursor fluid with the inside surface of the picowells and subsequently solidifying the precursor fluid, forming the layer of the coating material. Depending on the nature of the precursor fluid, solidifying is performed by any number of methods including but not limited to heating the precursor fluid, cooling the precursor fluid, polymerizing the precursor fluid, cross-linking the precursor fluid, curing the precursor fluid, irradiating the precursor fluid, illuminating the precursor fluid, gelling the precursor fluid, exposing the precursor fluid to a fixative or waiting a period of time.

One preferred method of coating the inside surfaces of picowells of a device of the present invention, applicable to virtually any device produced by virtually any method, is by vapor deposition. Vapor deposition involves the deposition of materials such as molecules or atoms onto a surface at low pressures and is characterized by the production of evenly thin coatings on a surface, such as the inner surface of a picowell of a device of the present invention.

In one embodiment of vapor deposition to the inside surfaces of picowells of a device of the present invention, the atoms or molecules that make up the coating material are deposited. In another embodiment of vapor deposition, the atoms or molecules that comprise a precursor of the coating material are deposited on the inside surfaces of the picowells, followed by solidifying the coating precursor material thereby forming the layer of coating material. Solidifying of the coating precursor material to form the layer of coating material is performed by any number of methods including but not limited to heating the coating precursor material, cooling the coating precursor material, polymerizing the coating precursor material, cross-linking the coating precursor material, curing the coating precursor material, irradiating the coating precursor material, illuminating the coating precursor material, gelling the coating precursor material, exposing the coating precursor material to a fixative and waiting a period of time.

A preferred coating material for coating the inside surfaces of picowells of a device of the present invention is made of polymerized para-xylylene molecules (or derivatives thereof, specifically where one or more hydrogens, especially aromatic hydrogens of either or both aromatic rings are substituted) deposited by vapor deposition, a coating commercially known as Parylene® (available for example from V&P Scientific, Inc., San Diego, Calif., USA). Parylene® is preferred not only for cell proliferation influencing properties but also for the fact that Parylene® coatings are bacteria resistant, fungus resistant, transparent, have a low permeability, acid and base resistant, uniform, thin (typically 0.1-1 micron) and without voids even when a coated surface includes configurations with sharp edges, points, flat surfaces, crevices or exposed internal surfaces.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. Although the invention has been described in conjunction with specific embodiments thereof, it is evident that many alternatives, modifications and variations will be apparent to those skilled in the art. Accordingly, the present invention is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In case of conflict, the specification herein, including definitions, prevails. Citation or identification of any reference in this application shall not be construed as an admission that such reference is available as prior art to the present invention.

What is claimed is:

1. A method of studying living cells having a density that is lower than that of a medium in which the cells are contained, comprising:
   providing a chamber having a first wall and a second wall, respectively defining top and bottom walls for the chamber, wherein each wall has a first surface inside the chamber and a second surface outside the chamber and wherein the chamber has one or more picowells a bottom of which is on the first surface of the top wall;
   loading a quantity of a cell-containing medium containing cells having a density that is lower than that of the medium into the chamber through an opening therein; and
   allowing the loaded cells to float upwardly toward the first surface of the top wall and thereby to be confined in the picowells; and studying the cells with the chamber positioned so that open ends of the wells face downward.

2. The method of claim 1, wherein said picowells are comprised in a picowell array.

3. The method of claim 1, wherein the cells are confined to the picowells by:
   a) introducing a medium into said chamber; then
   b) introducing a living cell of a first type into said container;
   c) selecting said medium so that said living cells are less dense than said medium; and
   d) orienting said chamber so that said bottom surface of said top wall faces substantially downwards,
   whereby said living cell of said first type floats upwards in said medium to be held in a said picowells for study.

4. The method of claim 3, wherein said medium and said living cell of said first type are introduced through an opening in a bottom wall of said chamber; and, subsequent to said introduction, said opening is substantially closed with a closing component.

5. The method of claim 4, wherein said closing component constitutes a part of a fluid inlet in fluid communication with said chamber.

6. The method of claim 4, further including at least one picowell on said top surface and further comprising:
   e) introducing a living cell of a second type that is denser than said medium into said picowell on said top surface, whereby, when said chamber is oriented so that said bottom surface of said top wall faces substantially downwards, the top surface of said bottom wall faces substantially upward, and said living cell of said second type settles into a said picowell on said top surface for study.

7. The method of claim 6, wherein said picowell on the top surface of the bottom wall of said chamber is comprised in picowell array.

8. The method of claim 4, wherein said chamber is oriented so that said opening in said bottom wall faces substantially upward while said medium and said living cell of said first type are introduced.

9. The method of claim 1, further including positioning said chamber with its top wall at the bottom and a bottom wall at the top when said medium and said living cells are introduced into said chamber, and inverting said chamber when the cells are to be studied.

10. The method of claim 1, further including orienting the chamber in a loading position wherein the top wall is below the bottom wall before cells are loaded; and
    closing the opening after the cells have been loaded; and
    wherein the cells are allowed to float toward the first surface of the top wall by inverting the chamber so that the top wall is above the bottom wall.

11. The method of claim 1, further including introducing at least one active agent into the cavity so that it comes in contact with the contents of the picowells; and
    studying the cells during or after introduction of the active agent.

12. The method of claim 11, wherein the active agent is introduced into the chamber through a fluid inlet separate from the opening through which the cells are loaded.

13. The method of claim 12, wherein said fluid inlet is a capillary channel.

14. The method of claim 13, wherein said fluid outlet is a capillary channel.

15. The method of claim 14, wherein said chamber includes an excess gas storage area, and the method further includes:
    orienting the chamber so that gas trapped in the chamber after the medium has been added enters the excess gas storage area; and
    removing the excess gas from said chamber through the fluid outlet.

16. The method of claim 11, wherein the active agent is introduced to said picowells through a fluid inlet comprised of a capillary channel defined at least in part by walls of made from a silicone material.

17. The method of claim 16, wherein said fluid inlet includes a hole through said bottom surface of said device body in fluid communication with said capillary channel.

18. The method of claim 16, wherein said silicone material is a silicone rubber.

19. The method of claim 16, wherein two opposing walls of said capillary channel are made out of a silicone rubber.

20. The method of claim 1, further comprising removing fluid from said chamber through at least one fluid outlet in fluid communication with said chamber.

21. The method of claim 1, further including:
    coupling a gas reservoir to the interior of the chamber; and
    increasing the content of the gas in the chamber by admitting gas from the gas reservoir.

22. The method of claim 1, wherein, subsequent to loading the cells, the opening through which the cells are introduced is closed by positioning a movable component.

23. The method of claim 22, wherein said movable component constitutes a part of a fluid inlet in fluid communication with the chamber.

24. The method of claim 1, wherein the cells are observed through the top wall of the chamber.

* * * * *